(12) United States Patent
Barrett et al.

(10) Patent No.: US 7,517,643 B2
(45) Date of Patent: Apr. 14, 2009

(54) COMPOUNDS DISPLAYED ON REPLICABLE GENETIC PACKAGES AND METHODS OF USING SAME

(75) Inventors: Ronald W. Barrett, Saratoga, CA (US); William J. Dower, Menlo Park, CA (US); Mark Gallop, Los Altos, CA (US); Thomas F. Woiwode, Menlo Park, CA (US); Steven E. Cwirla, Menlo Park, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

(21) Appl. No.: 11/187,989

(22) Filed: Jul. 22, 2005

(65) Prior Publication Data

US 2005/0255462 A1    Nov. 17, 2005

Related U.S. Application Data

(62) Division of application No. 09/675,525, filed on Sep. 29, 2000, now Pat. No. 7,037,706.

(60) Provisional application No. 60/156,675, filed on Sep. 29, 1999.

(51) Int. Cl.
*C12Q 1/70* (2006.01)
*C12N 7/01* (2006.01)
*C12N 15/00* (2006.01)
*C12N 15/09* (2006.01)
*G01N 33/53* (2006.01)

(52) U.S. Cl. .................. 435/5; 435/235.1; 435/320.1; 435/7.1

(58) Field of Classification Search ............... None
See application file for complete search history.

(56) References Cited

U.S. PATENT DOCUMENTS

| | | | |
|---|---|---|---|
| 5,403,484 A | 4/1995 | Ladner et al. | |
| 5,514,548 A | 5/1996 | Krebber et al. | |
| 5,571,698 A | 11/1996 | Ladner et al. | |
| 5,639,603 A | 6/1997 | Dower et al. | |
| 5,723,598 A | 3/1998 | Lerner et al. | |
| 5,766,905 A | 6/1998 | Studier et al. | |
| 5,837,500 A | 11/1998 | Ladner et al. | |
| 5,958,703 A | 9/1999 | Dower et al. | |
| 6,027,890 A | 2/2000 | Ness et al. | |
| 6,057,098 A | 5/2000 | Buechler et al. | |
| 6,174,687 B1 * | 1/2001 | Rajotte et al. | 435/7.1 |
| 6,309,842 B1 | 10/2001 | Dower et al. | |
| 6,777,239 B2 | 8/2004 | Dower et al. | |

FOREIGN PATENT DOCUMENTS

| WO | WO 93/11236 | 6/1993 |
|---|---|---|
| WO | WO 97/10507 | 3/1997 |
| WO | WO 98/51325 | 11/1998 |
| WO | WO 98/51825 | 11/1998 |
| WO | WO 01/05950 A2 | 1/2001 |
| WO | WO 01/23619 A1 | 4/2001 |
| WO | WO 02/077182 A2 | 10/2002 |

OTHER PUBLICATIONS

Chang et al (Subtiligase: A Tool for Semisynthesis of Proteins. PNAS, 1994. 91:12544-22548).*
Ivanenkov et al (Targeted delivery of multivalent phage display vectors into mammalian cells. Biochimica et Biophysica ACTA, 1999. 1448: 463-472.).*
Mukhija and Erni (Phage display selection of peptides against enzyme I of the phosphoenolpyruvate-sugar phosphotransferase system (PTS). Molecular Microbiology, 1997. 25(6): 1159-1166).*
Jostock, T. et al., "Screening of Molecular Repertoires by Microbial Surface Display", 2005, Combinatorial Chem. & high Throughput Screen., vol. 8: pp. 127-133.*
Levin, A. M., et al., "Optimizing the affinity and specificity of proteins with molecular display", 2006, Mol. Biosyst., vol. 2: pp. 49-57.*
Armstrong, et al., "Orientation of the Virion During Assembly and Disassembly," *IRL Press Limited*, 1641-1646 (1983).
Brenner et al., "Encoded combinatorial chemistry," *PNAS*, 89:5381-5383 (1992).
Bukanov et al., "A Modified Two-Step Phage Display Selection for Isolation of Polycytin-1 Ligands," *Funct. Integr. Genomics*, 1:193-199 (2000).
Chang, et al., "Subtiligase: A Tool for Semisynthesis of Proteins," *PNAS*, 91:12544-12548 (1994).
Crameri et al., "Display of Biologically Active Proteins on the Surface of Filamentous Phages: A cDNA Cloning System for Selection of Functional Gene Products Linked to the Genetic Information Responsible for their Production," *Gene*, 137:69-75 (1993).
Cwirla et al., "Peptides on Phage: A Vast Library of Peptides for Identifying Ligands," *PNAS*, 87:6378-6382 (1990).
Danner et al., "T7 Phage Display: A Novel Genetic Selection System for Cloning RNA-binding Proteins from cDNA Libraries," *PNAS*, 98(23):12954-12959 (2001).
Dente et al., "Modified Phage Peptide Libraries as a Tool to Study Specificity of Phophorylation and Recognition of Tyrosine Containing Peptides," *J. Molecular Biology*, 269(5):694-703 (1997).
Devlin et al., "Random Peptide Libraries: A Source of Specific Protein Binding Molecules," *Science*, 249:404-406 (1990).
Dwyer et al., "Biosynthetic Phage Display: A Novel Protein Engineering Tool Combining Chemical and Genetic Diversity," *Chemistry & Biology*, 7(4):263-274 (2000).
Ellman et al., "Combinatorial chemistry—Editorial overview," *Current Opinion in Chemical Biology*;, 2:317-319 (1998).
Maclean et al., "Encoded combinatorial chemistry: synthesis and screening of a library of highly functionalized pyrolidines," *Proceedings of the National Academy of Sciences of the United States of America*, 94(7):2805-2810 (1997).

(Continued)

*Primary Examiner*—Michael Burkhart
(74) *Attorney, Agent, or Firm*—Townsend and Townsend and Crew LLP

(57) ABSTRACT

Replicable genetic packages and collections thereof that display various compounds are provided. In some instances, the replicable genetic packages include nucleic acid tags that serve to record a characteristic of the compound or compounds that are attached to the replicable genetic package. The invention further provides a number of different methods for using the replicable genetic packages to screen a library of compounds for a desired biological activity.

18 Claims, 21 Drawing Sheets

OTHER PUBLICATIONS

Nakashima et al., "Chemical Modification and Molecular Orientation of the B Protein in the Filamentous Bacterial Virus Pf1," *J. Mol. Biol.*, 138:493-501 (1980).

Sandman et al., "Phage Display of Selenopeptides," *J. Am. Chem. Soc.*, 122:960-961 (2000).

Scott et al., "Searching fo the Peptide Ligands with an Epitope Library," *Science*, 249:386-390 (1990).

Woiwode et al., "Synthetic compound libraries displayed on the surface of encoded bacteriophage." *Chemistry and Biology*, 10(9):847-858 (2003).

Mauriello, E.M.F. et al., "Display of Heterologous Antigens on the *Bacillus subtilis* Spore Coat Using CotC as a Fusion Partner," 2004, Vaccine, 22, 1177-1187.

Isticato, R. et al., "Surface Display of Recombinant Proteins on *Bacillus subtilis* Spores," Nov. 2001, Journal of Bacteriology, vol. 183, No. 21, 6294-6301.

Ausubel, F. M. et al., *Current Protocols in Molecular Biology*, vol. 1-4, John Wiley & Sons, Inc., 2000.

Sambrook, J. et al., *Molecular Cloning: A Laboratory Manual*, 2nd Edition, Cold Spring Harbor Laboratory Press, 1989.

\* cited by examiner

| Functionality | Resin Attachment |
|---|---|
|  | 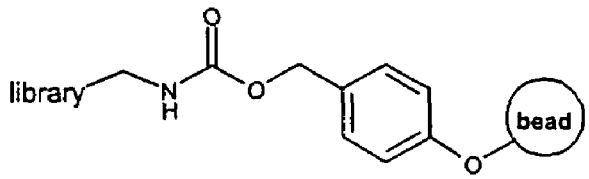 |
|  | 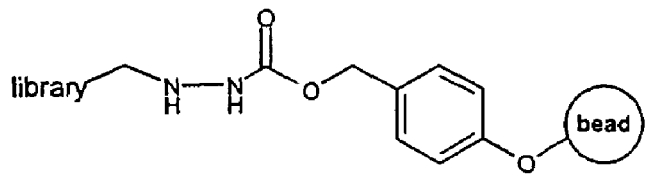 |
| 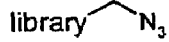 | 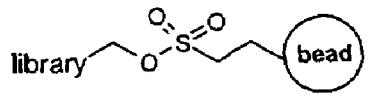 |
| 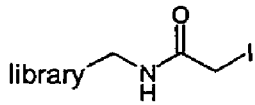 | 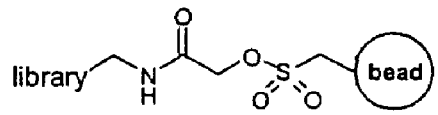 |
| 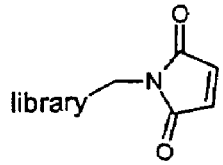 | 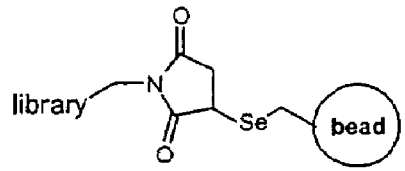 |
| 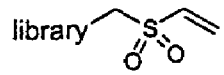 | 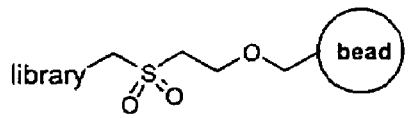 |
| 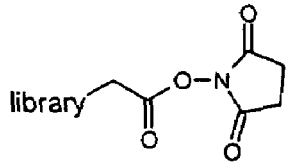 | 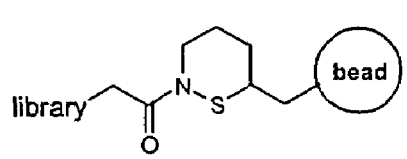 |
FIG. 5

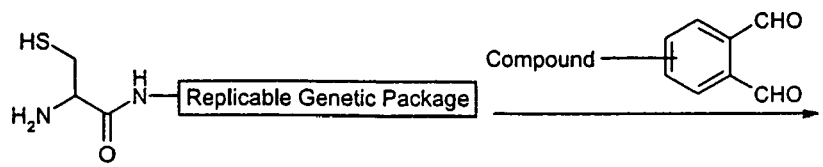
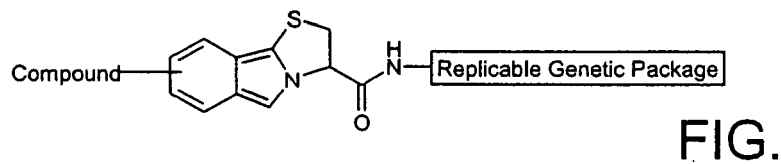
FIG. 7A
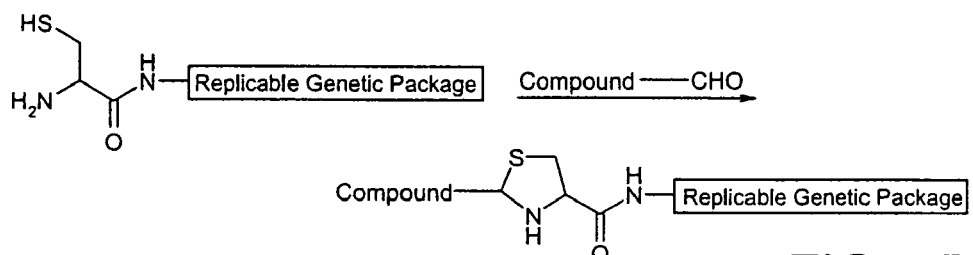
FIG. 7B
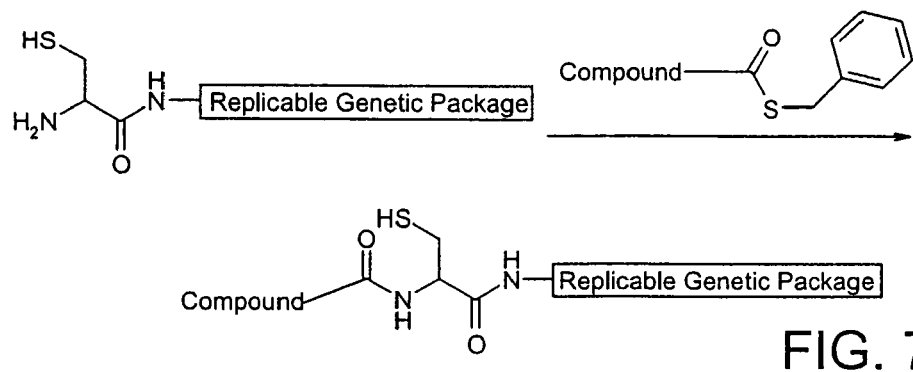
FIG. 7C
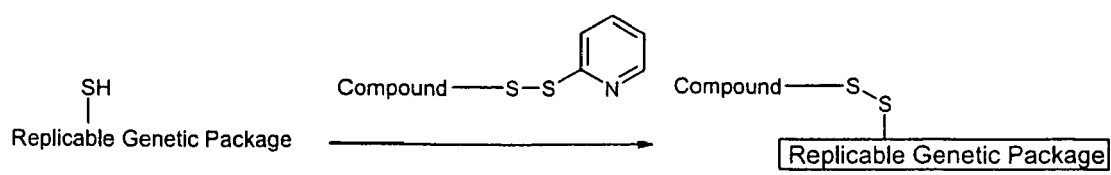
FIG. 7D

Filamentous phagemid display (gene VIII)

```
                              biotin
                                |
    G G L N D I F E A Q K I E W H E     G G G G S
...GGCGGGGCTTAATGATATTTTTGAGGCTCAGAAGATTGAGTGGCATGAGGAGGCGGGGGGTAGC...gene 8
    biotinylation substrate sequence           flexible spacer
```

FIG. 10A

T7 display (gene 10B)

```
                                                   biotin
                                                     |
           N S G G G G   L N D I F E A Q K I E W H E *
gene 10B..AATTCTGGAGGCGGGGGTCTTAATGATATTTTTGAGGCTCAGAAGATTGAGTGGCATGAGTGAGTAAGTAACTAA
           spacer        biotinylation substrate sequence
```

A: all proteins
1 2 3 4 5 6 7 8 9 10 11

B: Flouresceinated proteins
1 2 3 4 5 6 7 8 9 10 11

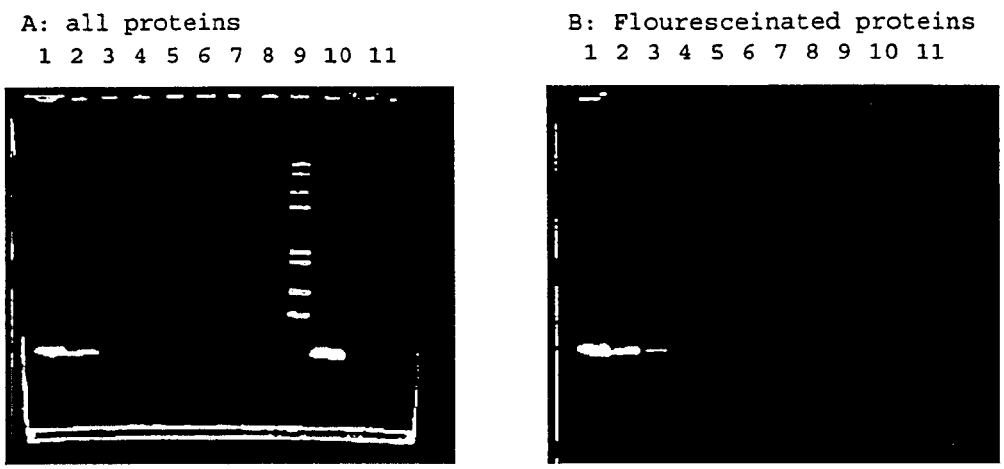

Lanes 1-8: Fd phage treated with fluorescein-NHS ester (2X dilutions)
Lane 9: MW markers
Lanes 10-11: Fd phage treated with fluorescein-$CO_2H$ (10X dilution)

FIG. 19

A: all proteins
1 2 3 4 5 6 7

B: Flouresceinated proteins
1 2 3 4 5 6 7

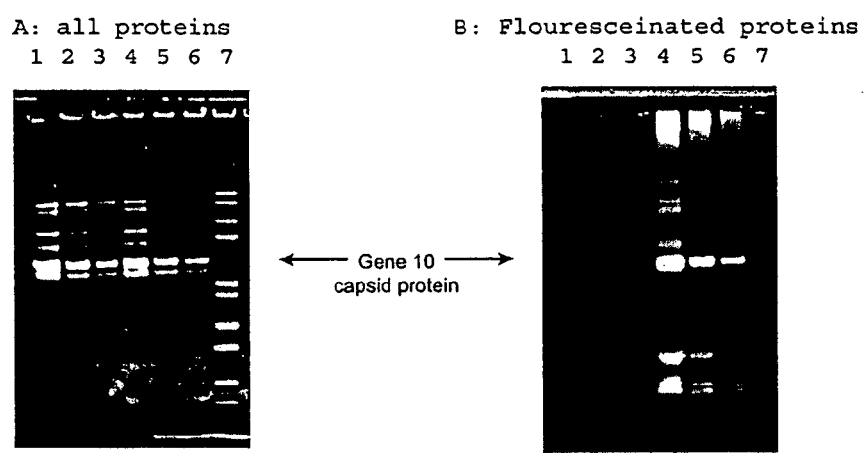

← Gene 10 →
capsid protein

Lanes 1-3: T7 phage treated with fluorescein-$CO_2H$ (2X dilutions)
Lanes 4-6: T7 phage treated with fluorescein-NHS ester (2X dilutions)
Lane 7: MW markers

COMPOUNDS DISPLAYED ON REPLICABLE GENETIC PACKAGES AND METHODS OF USING SAME

CROSS-REFERENCES TO RELATED APPLICATIONS

This application is a division of U.S. application Ser. No. 09/675,525, now U.S. Pat. No. 7,037,706, filed Sep. 29, 2000, which claims the benefit under 35 U.S.C. § 119(e) of U.S. Provisisional Application No. 60/156,675, filed Sep. 29, 1999, both of which are incorporated herein by reference in its entirety.

FIELD OF INVENTION

The present invention resides in the field of combinatorial chemistry and drug discovery.

BACKGROUND OF THE INVENTION

The search for new compounds frequently involves screening large libraries of compounds to identify a small subset of compounds that have a desired activity or characteristic. The use of combinatorial chemistry and high-throughput screening has greatly increased the speed at which lead compounds can be identified. Recombinant peptide libraries displayed on phage or other viral particles have proven especially useful in such screens (see, e.g., Cwirla, et al., Proc. Natl. Acad. Sci. USA 87:6378-6382 (1990); Devlin, et al., Science 249:404-406 (1990), Scott & Smith, Science 249:386-388 (1990); and Ladner, et al., U.S. Pat. No. 5,571,698, each of which is incorporated herein by reference in its entirety).

Phage display methods typically involve the insertion of random oligonucleotides into a phage genome such that they direct a bacterial host to express peptide libraries fused to phage coat proteins (e.g., filamentous phage pIII, pVI or pVIII). Libraries of up to $10^{10}$ individual members can be routinely prepared in this way. Incorporation of the fusion proteins into the mature phage coat results in the peptide encoded by the exogenous sequence being displayed on the exterior surface of the phage, while the exogenous sequence encoding the peptide resides within the phage particle.

This establishment of a physical association between the displayed peptide and the genetic material encoding it allows simultaneous mass screening of very large numbers of phage bearing different peptides. Phage displaying peptides having binding specificity for a particular target can be enriched by affinity screening against the target. The identity of such peptides can be determined from the exogenous sequence contained in the phage displaying the peptide. Peptides so identified can subsequently be synthesized in bulk using conventional synthetic chemistry methods. This technology is further empowered by its very high sensitivity. The ability to amplify hits by culturing phage particles selected in a screen allows a single positive event to be identified.

Phage display also allows screening of peptides in a format in which multiple copies of the same protein are displayed from a single phage. The presence of multiple peptide on the surface allows detection of peptide/target interactions of low affinity. For example, phage display systems in which the peptide is fused to either pIII or pVIII allow the detection of peptides with dissociation constants as high as 100 μM, provided the target is immobilized in active form at high density to permit multivalent bonding of a phage to target molecules.

The basic phage display technology has been expanded to include peptide libraries that are displayed from replicable genetic packages other than phage, such as eukaryotic viruses and bacteria. The principles and strategy are closely analogous to those employed for phage, namely, that nucleic acids encoding peptides to be displayed are inserted into the genome of the package to create a fusion protein between the peptides to be screened and an endogenous protein that is exposed on the cell or viral surface. Expression of the fusion protein and transport to the cell surface results in display of peptides from the cell or viral surface.

A significant limitation with current phage-display technology, is that it is only applicable to display of peptides. Many of the most effective drugs, however, are small organic molecules. Because of the poor pharmacokinetic properties of peptides, lead candidates need to be transformed into non-peptidic structures to fully realize their pharmaceutical potential. A great deal of effort has been dedicated towards converting peptide structures into peptidomimetics, which retain the activity of the peptide but do not suffer from a short serum half-life and poor bioavailability. Unfortunately, these efforts have been largely unsuccessful.

SUMMARY OF THE INVENTION

Replicable genetic packages to which a wide variety of compounds are attached are provided. These replicable genetic packages can be utilized to rapidly screen large libraries of compounds to identify compounds that have a desired activity. Some of the replicable genetic packages harbor a nucleic acid tag that encodes a characteristic of the compound or compounds borne by the replicable genetic package. The tag can be utilized as a convenient way to identify active compounds. The use of compound-bearing replicable genetic packages allows for ease of quantitation and high sensitivity in a variety of different types of assays. A significant amount of information can also be encoded within the nucleic acid or genome of the replicable genetic package.

Certain of the replicable genetic packages display a compound other than a polypeptide and harbor a heterologous nucleic acid tag that encodes for a characteristic of the compound. A variety of different replicable genetic packages can be used to display the compound. Examples of replicable genetic packages include viruses, bacteriophage, bacteria, spores and cells. If the replicable genetic package is a bacteriophage, the replicable genetic package can be either a filamentous phage (e.g., fd, fl and MD13) or a non-filamentous phage such as the icosahedral phage T7 or lambda, for example. The type of compound attached to the replicable genetic package can vary. Exemplary compounds include heterocyclic compounds, carbocyclic compounds, proteins, combinations of various monomers such as amino acids, purine and pyrimidine bases and monosaccharides. Often the compounds are from combinatorial libraries.

The compounds can be attached in a variety of ways. Sometimes compounds are attached via a covalent bond formed between an endogenous functional group on the replicable genetic package and a functional group borne by the compound. Other replicable genetic packages bear a package linker, and the compound is attached to the replicable genetic package by association with the package linker. Likewise, in some instances, the compound bears a compound linker and the compound is attached to the replicable genetic package via the compound linker. Both the replicable genetic package and the compound can bear linkers, with association between the two linkers resulting in attachment of the compound to the replicable genetic package. The linkers can be of a number of different types. Certain linkers are members of binding pairs, with one member of the binding pair being attached to the replicable genetic package and the other to the compound.

Certain replicable genetic packages display multiple compounds. The compounds that are attached can be the same or different. When the replicable genetic package is a phage, for example, the multiple compounds can be attached to a single coat protein, different coat proteins having the same sequence or different coat proteins of different sequences. The replicable genetic packages can also bear a plurality of different exogenous attachment sites to which the compounds can be attached. These sites can have the same functionality or have different functionality such that different compounds are selectively attached to different attachment sites. In the case of phage, the attachment sites can be on a single coat protein, multiple coat proteins of the same sequence or multiple coat proteins having different sequences.

The heterologous nucleic acid tag is typically a nucleic acid segment other than a segment that encodes for an expressed polypeptide displayed on the replicable genetic package. The heterologous nucleic acid tag can encode a variety of things. In some instances, the tag encodes for a component of the compound; other tags encode the specific structural identity of the compound. Other tags encode a value or symbol assigned to the compound. In certain replicable genetic packages, the heterologous nucleic acid tag is inserted into a segment of the genome of the replicable genetic package (e.g., the genome of a phage) such that it is flanked by a heterologous promoter and a heterologous restriction site, the heterologous promoter being in operable linkage with the heterologous nucleic acid tag. This type of construct allows for transcription of the tag segment to generate a probe that can be used to screen replicable genetic packages to identify those bearing active compounds.

Other replicable genetic packages display a compound other than an expressed polypeptide, with the replicable genetic package and the compound being attached via a linker. The particular type of replicable genetic package can be any of those listed supra. Such replicable genetic packages optionally include a heterologous nucleic acid such as just described. These replicable genetic packages can also be linked via a compound linker an bear multiple compounds, which compounds can be the same or different.

Still other replicable genetic packages display a compound and include a heterologous nucleic acid tag that encodes a characteristic of the compound by a code other than the standard genetic code. The particular type of replicable genetic package can be any of those listed supra. Compounds can be linked to this particular type of replicable genetic package via linkers. These replicable genetic packages can also display multiple compounds which are the same or different.

Any of the replicable genetic packages can be part of a library. In certain libraries, the replicable genetic packages bear different compounds and harbor different heterologous nucleic acid tags. In some collections, the tags harbored by the different replicable genetic packages are isothermal tags which have the same base compositon. The compounds borne by the packages in certain collections are different compounds from a combinatorial library.

The replicable genetic packages can be used in a variety of screening assays. Certain screening methods involve contacting, for each compound to be screened, the compound with a replicable genetic package to form a plurality of replicable genetic packages displaying different compounds. These replicable genetic packages are then assayed to identify at least one replicable genetic package displaying at least one compound with a desired property.

The contacting step can be conducted in various ways to obtain the desired replicable genetic packages. For example, packages and compounds can be attached via a covalent bond formed between functional groups borne by the replicable genetic package and compound or via linkers. In certain methods, both the package and compound bear linkers and these are joined through non-covalent interactions. Certain methods involve modifying an endogenous functional group on the replicable genetic package using chemical and/or enzymatic approaches, with the compound becoming attached to the modified functional group. In certain methods, the replicable genetic packages are immobilized to a support and then contacted with the compounds to form the library of packages.

Certain methods involve pooling the replicable genetic packages and/or the compounds. For example, with some methods the compounds to be screened are combined into a plurality of pools and each pool is contacted with a single type of replicable genetic package. In other instances, the replicable genetic packages are combined into a plurality of pools and each pool is contacted with a single type of compound.

Other methods involve attaching a plurality of compounds at selected attachment sites on the replicable genetic packages. The attachment sites can be naturally occurring attachment sites or can be introduced. In the case of phage, for example, the attachment sites can be on a single coat protein, on different coat proteins of the same sequence or on different coat proteins having different sequences. By utilizing attachment sites of different functionality, one can selectively attach different compounds to different sites.

Related screening methods involve providing a plurality of replicable genetic packages displaying different compounds, wherein the compounds are other than an expressed polypeptide. These replicable genetic packages are then assayed to identify at least one replicable genetic package displaying at least one compound with a desired property.

Still other screening methods are conducted using replicable genetic packages that harbor heterologous nucleic acid tags. Some of these methods initially involve providing a plurality of different replicable genetic packages, each replicable genetic package displaying a compound other than an expressed polypeptide, with different replicable genetic packages displaying different compounds and harboring different heterologous nucleic acid tags. These replicable genetic packages are then assayed to identify at least one replicable genetic package displaying at least one compound with a desired property. The heterologous nucleic acid tag of the at least one replicable genetic package is decoded to identify a characteristic of the at least one compound with the desired property.

The different replicable genetic packages to be used in such assays can be formed, for each compound to be screened, by contacting the compound with a replicable genetic package, different compounds being contacted with different replicable genetic packages. In other methods, the compounds to be screened are combined into a plurality of pools and each pool is contacted with one or more replicable genetic packages that harbor the same heterologous nucleic acid tag, whereby each of the plurality of replicable genetic packages display a plurality of different compounds.

Decoding is accomplished in a variety of ways. In some instances, decoding involves sequencing the heterologous nucleic acid tag of the at least one replicable genetic package. Other decoding procedures involve generating a nucleic acid probe from the at least one replicable genetic package, the nucleic acid probe comprising or being complementary to the heterologous nucleic acid tag of the at least one replicable genetic package. This probe is then contacted with the heterologous nucleic acid tag from the different replicable genetic packages to identify the replicable genetic package to which the at least one compound was attached.

Other methods are conducted with replicable genetic packages that bear multiple compounds. Certain of these methods involve providing a plurality of different replicable genetic packages each displaying a compound and harboring a heterologous nucleic acid tag. These packages are then assayed to identify at least one replicable genetic package displaying at least one compound with a desired property. The heterologous nucleic acid tag of the at least one replicable genetic package is subsequently decoded to identify a characteristic of the at least one compound with the desirable property. In certain of these methods, the replicable genetic packages to be screened are formed first. One approach involves combining a plurality of replicable genetic packages harboring different nucleic acid tags into a pool. The pooled packages are then contacted with a compound such that at least some of the replicable genetic packages to be screened bear the same compound while harboring different tags. Alternatively, a plurality of compounds to be screened are combined into a pool and a plurality of replicable genetic packages harboring different nucleic acid tags are combined into a pool. The pool of replicable genetic packages is contacted with the pool of compounds such that the packages screened harbor different tags and bear the same plurality of compounds. These methods provide a convenient way to rapidly conduct initial screens. For pools showing activity, additional screens can be conducted to determine which compound in the pool is responsible for the observed activity. This can be done for example, by preparing packages that bear a single compound from those compounds in the active pool, with different packages optionally including a unique tag to aid in identification.

Any of the foregoing methods can be utilized to perform a wide variety of biological assays. For example, the methods can be used to assay individual compounds or libraries of compounds to identify compounds that have the capacity to bind to a receptor, the capacity to be transported into or through a cell, the capacity to be a substrate or inhibitor for an enzyme, the capacity to kill bacteria, fungi or other microorganisms, and the capacity to agonize or antagonize a receptor. Certain methods involve screening replicable genetic packages that bear multiple compounds to identify those in which multiple compounds interact with a target molecule (e.g., a receptor).

Assays utilizing replicable genetic packages to identify compounds that have the capacity to be transported through cells can be conducted in either in vitro or in vivo formats. In certain in vitro methods, a monolayer of polarized cells is layered above a membrane that is impermeable to the plurality of replicable genetic packages. Transport through the cell is assayed by detecting transport of a replicable genetic package through the cell to the membrane. In certain in vivo methods, a plurality of replicable genetic packages are introduced into a body compartment or tissue of an animal and allowed sufficient time for transport through cells lining the body compartment or tissue to occur. Replicable genetic packages bearing compounds able to effectuate transport through the cells are retrieved from a tissue or body fluid after being transported through the cells lining the body compartment and the identity of the compound(s) borne by the retrieved package determined. Some in vivo methods involve introducing the replicable genetic packages into the intestine of an animal to identify compounds capable of being transported through the intestinal epithelial cells. In other in vivo methods, the replicable genetic packages are introduced into the circulatory system of the animal and retrieved from the brain after transport through endothelial cells.

BRIEF DESCRIPTION OF THE DRAWINGS

FIG. 5 illustrates strategies to access phage attachment functionality upon cleavage from a solid support.

FIGS. 7A-7D illustrate other examples of approaches for joining a library compound a replicable genetic package.

FIGS. 10A and 10B depict various biotinylation substrate sequences (SEQ ID NOS:2-5). FIG. 10A shows a 16-amino acid BirA biotinylation substrate sequence fused to the 5' end of the gene for the filamentous phage coat protein pVIII. FIG. 10B shows a 16-amino acid BirA substrate sequence inserted into the 3' end of gene 10B, the major coat protein of T7 phage.

FIG. 16A shows ELISA results for filamentous phage when biotin was chemically conjugated to the phage using NHS ester, maleimide and amine/carbodiimide chemistries. FIG. 16B shows ELISA results for T7 phage when biotin was chemically conjugated to the phage using NHS ester, maleimide and amine/carbodiimide chemistries. FIG. 16C shows ELISA results with filamentous phage when biotin was chemically conjugated to the phage using hydrazide and iodoacetamide chemistries.

FIG. 17A shows titer results for filamentous phage treated with maleimide and NHS ester attachment chemistries. FIG. 17B shows titer results for filamentous phage treated with hydrazide and iodoacetamide attachment chemistries. FIG. 17C shows titer results for T7 phage treated with maleimide and NHS ester attachment chemistries.

FIGS. 18A and 18B are protein gels of fluoresceinated filamentous phage viewed in two channels: Channel A shows all the proteins on the gel; channel B shows only fluorescein-conjugated proteins.

FIGS. 19A and 19B are protein gels of T7 phage viewed in two channels: Channel A shows all the proteins on the gel; channel B shows only fluorescein-conjugated proteins.

DETAILED DESCRIPTION

I. Definitions

Figure 1:
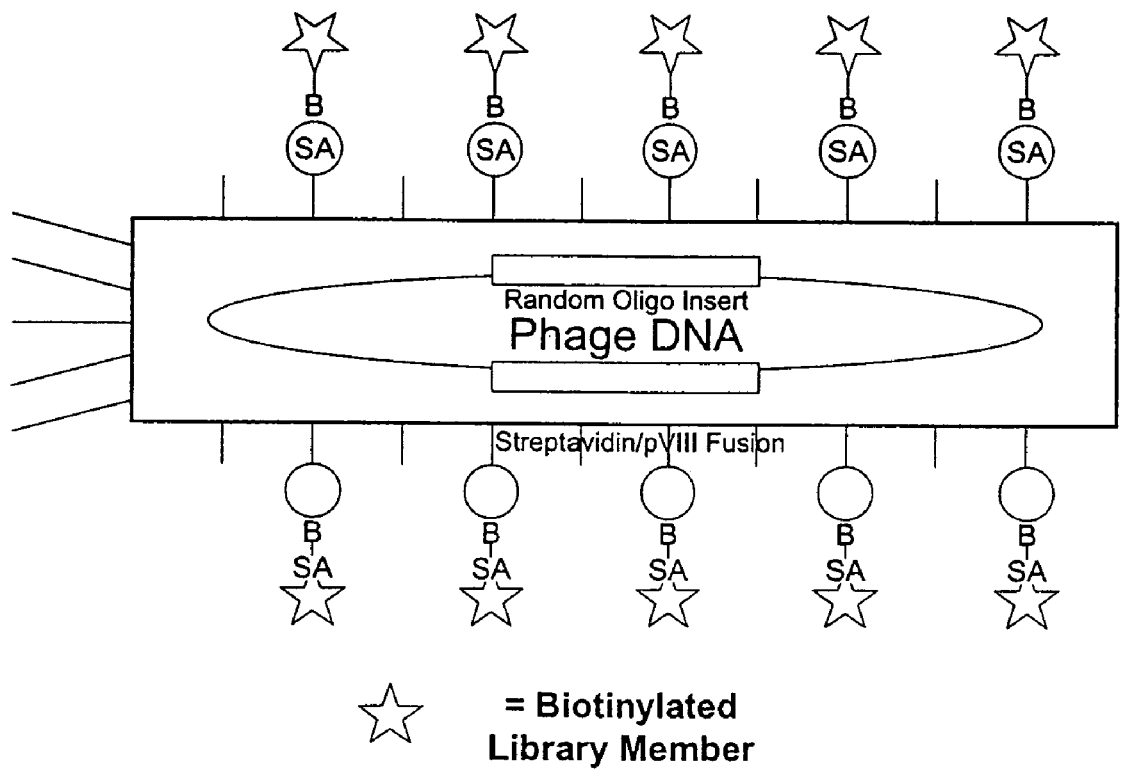
FIG. 1 is a schematic representation of a specific example of a replicable genetic package as disclosed herein, namely a package wherein the linker attached to the phage is streptavidin (SA) and the linker attached to the library compound is biotin (B).
Figure 2A:
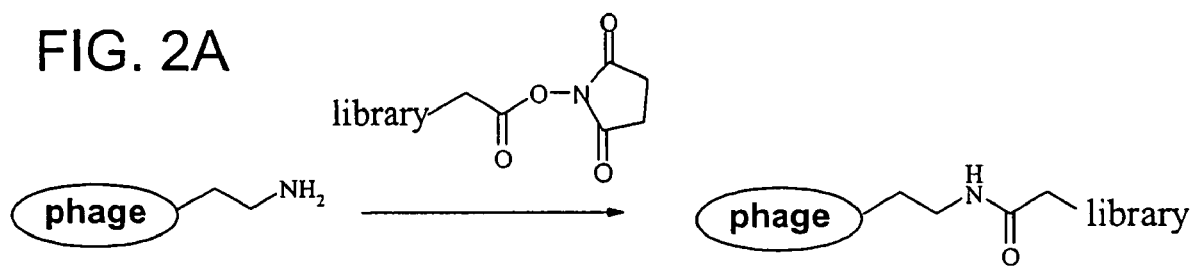
FIGS. 2A-2D depict exemplary strategies to effect the direct chemical conjugation of small molecule libraries to phage coat proteins.
Figure 2B:
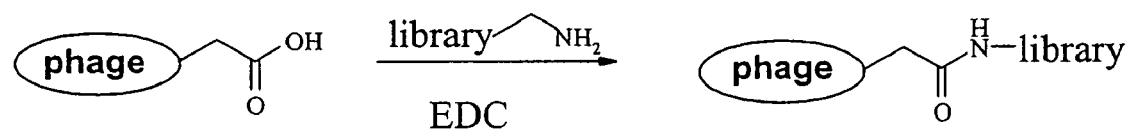
Figure 2C:
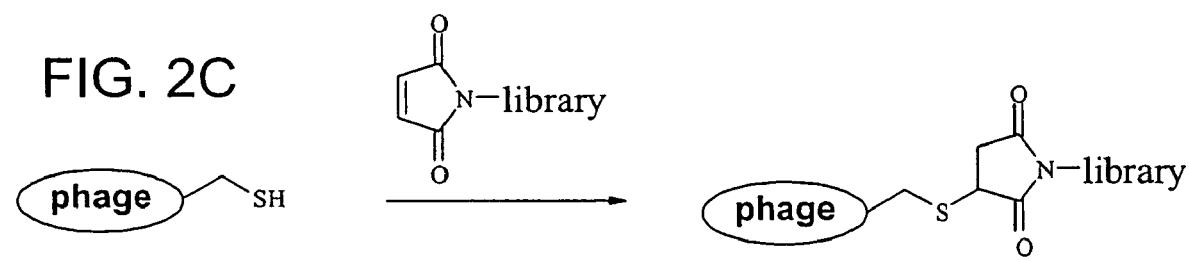
Figure 2D:
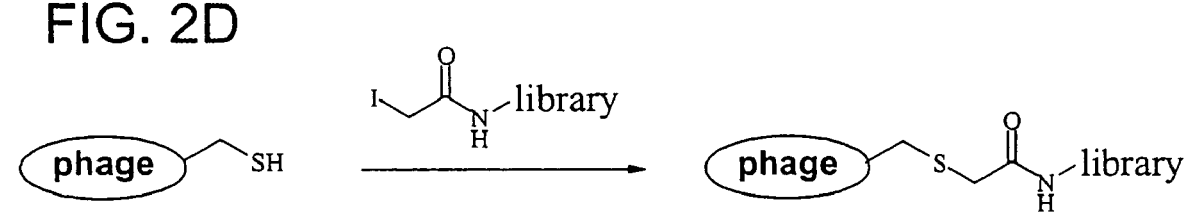

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occuring nucleotides.

A "polynucleotide" refers to a single or double-stranded polymer of deoxyribonucleotide or ribonucleotide bases.

An "oligonucleotide" is a single-stranded nucleic acid typically ranging in length from 2 to about 500 bases. Oligonucleotides are often synthetic but can also be produced from naturally occurring polynucleotides. Oligonucleotides can be prepared by any suitable method, including, for example, cloning and restriction of appropriate sequences and direct chemical synthesis by a method such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetrahedron Lett. 22:1859-1862 (1981); and the solid support method of U.S. Pat. No. 4,458,066.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site."

A "functional group" refers to an atom or group of atoms that defines the structure of a compound or family of compounds, while also determining the properties of the compound. Exemplary functional groups include, carboxyl, amino, sulfhydryl, carbonyl and double and triple bonds, for example.

The terms "polypeptides", "proteins" and "peptides" are used interchangeably and mean a polymer of amino acids.

The term "expressed polypeptide" refers to a polypeptide, protein, or peptide produced by translational expression of the nucleic acid of a replicable genetic package.

The term "a compound other than an expressed polypeptide" means a compound other than a polypeptide, protein or peptide produced by translational expression of the nucleic acid of the replicable genetic package.

Reference to a compound being "displayed" on replicable genetic package means that the compound is attached to a group (e.g., an amino acid residue) located at the exterior surface of the replicable genetic package.

A "small molecule" means a molecule having a molecular weight of less than 2000 daltons, in some instances less than 1000 daltons, and in still other instances less than 500 daltons or less. Such molecules include, for example, heterocyclic compounds, carbocyclic compounds, sterols, amino acids, lipids, and nucleic acids.

The term "naturally occurring" as applied to an object refers to the fact that an object can be found in nature.

An "exogenous" species is refers to a species that is not normally present in or displayed on a replicable genetic package, but can be introduced into a replicable genetic package by one or more genetic, biochemical or other methods. Normal presence in the replicable genetic package is determined with respect to the particular developmental stage and environmental conditions of the a replicable genetic package. An exogenous species can be, among other things, a small molecule, such as is generated by a combinatorial chemistry process, or a macromolecule such as a protein, nucleic acid, carbohydrate, lipid, glycoprotein, lipoprotein, polysaccharide, or any modified derivative of the above molecules, or any complex comprising one or more of the above molecules. When used in reference to a group such as a functional group or attachment site on the surface of a replicable genetic package, exogenous means the functional group or attachment site that does not naturally occur on the surface of the package. Such a group can be a functional group appearing at the surface of the package that has been derivatized or modified, for example.

By contrast, an "endogenous" species is one that is normally present in or on a replicable genetic package at a particular developmental stage under particular environmental conditions.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," is one that originates from a source foreign to the particular replicable genetic package, or, if from the same source, is modified from its original form. Thus, a heterologous gene in a prokaryotic replicable genetic package includes a gene that, although being endogenous to the particular host replicable genetic package, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a replicable genetic package indicates that the cell replicates a heterologous nucleic acid, or expresses a peptide or protein encoded by a heterologous nucleic acid. Recombinant replicable genetic packages can contain genes that are not found within the native (non-recombinant) form of the replicable genetic packages. Recombinant replicable genetic packages can also contain genes found in the native form of the replicable genetic package wherein the genes are modified and re-introduced into the replicable genetic package by artificial means. The term also encompasses replicable genetic packages that contain a nucleic acid endogenous to the replicable genetic package that has been modified without removing the nucleic acid from the replicable genetic package; such modifications include those obtained by gene replacement, site-specific mutation, and related techniques.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments can be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv" or "scFv") polypeptide is a covalently linked VH::VL heterodimer which can be expressed from a nucleic acid including VH- and VL-encoding sequences either joined directly or joined by a peptide-encoding linker. Huston, et al. Proc. Nat. Acad. Sci. USA, 85:5879-5883 (1988). A number of strategies for converting the naturally aggregated—but chemically separated light and heavy polypeptide chains from an antibody V region into an scFv molecule that will fold into a three dimensional structure substantially similar to the structure of an antigen-binding site, have been reported. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

The term "epitope" refers to the portion of an antigen that interacts with an antibody. More specifically, the term epitope includes any protein determinant capable of specific binding to an immunoglobulin or T-cell receptor.

The phrases "specifically binds" when referring to a protein or "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988)

*Antibodies, A Laboratory Manual,* Cold Spring Harbor Publications, New York, for a description of immunoassay formats and conditions that can be used to determine specific immunoreactivity.

A "binding pair" or "binding partners" refers to a first and second moiety that specifically bind to each other. Exemplary binding pairs include, but are not limited to, biotin and either streptavidin, avidin or neutravidin; a hapten and an antibody thereto; and an enzyme and an inhibitor.

A "transport protein" is a protein that has a direct or indirect role in transporting a molecule into and/or through a cell. The term includes, for example, membrane-bound proteins that recognize a substrate and effects its entry into a cell by a carrier-mediated transporter or by receptor-mediated transport. Transport proteins are sometimes referred to as "transporter proteins" or simply "transporters." The term also includes intracellularly expressed proteins that participate in trafficking of substrates through or out of a cell. The term also includes proteins or glycoproteins exposed on the surface of a cell that do not directly transport a substrate but bind to the substrate holding it in proximity to a receptor or transporter protein that effects entry of the substrate into or through the cell. Transport proteins involved in carrier-mediated transport are referred to as carrier-type transport proteins or simply carrier-type transporters. Those transport proteins involved in receptor-mediated transport are referred to as receptor-type transport proteins or simply receptor-type transporters.

Some examples of transporter proteins effecting carrier-mediated transport of nutrients, vitamins and xenobiotics include, but are not limited to: glutamate/neutral amino acid transporter; facilitated glucose transporter; d2/NBAT and 4F2 transporter; sodium/glucose transporter; GABA transporter; amino acid permease transporter; sodium/bile acid transporter; proton/oligopeptide transporter; monoamine transporter; folate transporter; organic anion/prostaglandin transporter; organic cation/organic anion transporter; sodium/ascorbic acid transporter; fatty acid transporter; sodium/nucleoside transporter and facilitated nucleoside transporter. Other examples of carrier proteins include: the ileal bile acid transporter (ASBT or IBAT); the liver bile acid transporters (NTCP); dipeptide transporters; oligopeptide transporters; simple sugar transporters (e.g., SGLT1); phosphate transporters; monocarboxylic acid transporters; ATP-binding cassette (ABC) family (e.g., P-glycoprotein); organic anion transporters (OATP); organic cation transporters; amino acid transporters; nucleoside transporters; vitamin transporters; and electrogenic transporters that carry charged substrates. Examples of receptor-mediated transport proteins include: viral receptors, immunoglobulin receptors, bacterial toxin receptors, plant lectin receptors, bacterial adhesion receptors, vitamin transporters and cytokine growth factor receptors.

A "substrate" of a transport protein is a compound whose uptake into or passage through a cell is facilitated by the transport protein.

The term "ligand" of a transport protein includes substrates and other compounds that bind to the transport protein without being taken up or transported through a cell. Some ligands by binding to the transport protein inhibit or antagonize uptake of the compound or passage of the compound through a cell by the transport protein. Some ligands by binding to the transport protein promote or agonize uptake or passage of the compound by the transport protein or another transport protein. For example, binding of a ligand to one transport protein can promote uptake of a substrate by a second transport protein in proximity with the first transport protein.

II. General

Disclosed herein are various replicable genetic packages that display a wide variety of compounds, including compounds other than expressed polypeptides. These replicable genetic packages can be utilized to conduct a variety of assays with high sensitivity. Compounds to be screened are sometimes synthesized independently of the replicable genetic packages and subsequently attached to preformed replicable genetic packages. Other compounds are directly synthesized on the replicable genetic package. Typically, the attachment is performed in such a manner that a clonal isolate of a genetic package receives a distinct compound or pool of compound, and a correspondence regime is preserved indicating which isolate receives which compound(s).

In some methods, the replicable genetic packages bear nucleic acid tags which serve to record at least one characteristic of a compound or pool of compounds attached to a clonal isolate of the package. Usually such a tag is a nucleic acid segment other than a segment that encodes for a peptide (or portion thereof) displayed by the replicable genetic package. In such methods, after attachment of compounds to replicable genetic packages, the different clonal isolates can be pooled for screening, and the identity of compounds tracked from the tags. In other methods, the replicable genetic packages lack tags, and are tracked by separate screening of different clonal isolates. Packages lacking tags can also be pooled. Pools showing activity are subjected to another round of screening to determine which compound borne by one of the packages in the pool is active.

There are several challenges to developing replicable genetic packages that display compounds other than expressed polypeptides. In the display of small molecules from a replicable genetic package for example, the host bacterial cell or the replicable genetic package itself can no longer be relied upon to synthesize the library. As a result, small molecules are either synthesized separately and then attached to replicable genetic package or the compounds synthesized directly on the replicable genetic package. Second, the attachment regime should be performed in such a way that the particular compound(s) borne by a replicable genetic package can be determined. In some instances, this means establishing a 1:1 correlation between individual members of the small molecule library and unique clonal isolates. This allows for the unique DNA sequence of individual phage clones to ultimately identify lead compounds with activity in a given assay. Another challenge, particularly an issue when phage are utilized, is that the conjugation method should not interfere with the infectivity of the phage particle, as this is important to its amplification.

The replicable genetic packages of the invention can be used in a variety of different screening methods to identify compounds with a desired biological activity. For example, the packages can be used to identify library members capable of: 1) binding to a receptor, 2) being transported into or through a cell, 3) functioning as a substrate or inhibitor of an enzyme, 4) killing bacteria, fungi or other microorganisms, 5) triggering signal transduction and 6) agonizing or antagonizing a receptor. The replicable genetic packages of the invention are capable of displaying multiple copies of a single compound (i.e., multivalent display) or single or multiple copies of multiple compounds, thereby facilitating identification of compounds that bind with low-affinity to the receptor.

Initial rounds of screening can be followed with more refined screening rounds. For example, subsequent screening tests can be performed using compounds related to a lead compound identified during initial rounds of screening to identify compounds that have activity that exceeds that of the lead compound. Additional screening can also be performed on compounds in free form or attached to a moiety other than a replicable genetic package. Moieties screened can include compounds that complement the activity of the active compound or particles that bear or encapsulate other desired compounds.

III. Replicable Genetic Packages

A. General

Replicable genetic packages that display essentially any compound capable of being attached to a replicable genetic package are provided herein. Certain replicable genetic packages display compounds other than expressed polypeptides, such as small organic molecules. Some replicable genetic packages display peptides in which the peptide is attached to a replicable genetic package via a peptide bond, whereas peptides in other replicable genetic packages are attached via a bond other than a peptide bond. As shown in FIG. 1, the compound-bearing packages can include one or more linkers for attaching the compound to the replicable genetic package. However, as described further infra, some replicable genetic packages are directly conjugated to the compound(s) they bear.

When linkers are utilized, in some instances one linker is either attached to the exterior surface of the replicable genetic package or is attached to a linkage site on the compound. In other instances, two linkers are utilized—one linker being attached to the exterior surface of the replicable genetic package and the second linker attached to the compound. The interaction between the two linkers acts to join the compound to the replicable genetic package. In still other instances, one or more bridging linkers can be utilized to effectuate the association between a package linker and a compound linker. Such an arrangement is useful, for example, for extending the distance between the compound and the surface of the replicable genetic package. This arrangement minimizes unfavorable steric interactions between the compound and the replicable genetic package. Any of these linkers can be a reversible linker that can be cleaved, thereby providing a mechanism for the release of compound from a replicable genetic package. As described in greater detail below, the replicable genetic packages of the invention can also optionally include a tag that encodes for the identity or a characteristic of the compound(s) borne by a replicable genetic package, thus providing a means for identifying the compound attached to replicable genetic package shown to be active in an assay. In the specific example illustrated in FIG. 1, the linker attached to the replicable genetic package is streptavidin and the linker borne by the compound is biotin.

The invention also provides collections or libraries of replicable genetic packages. Typically, such collections includes at least 3, 4, 5, 6, 7, 8 or 9 replicable genetic packages, each displaying a compound other than a polypeptide, wherein the replicable genetic packages each bear a first linker and the compound a second linker. In such libraries, the compounds attached to members of the library differ. Such libraries can include replicable genetic packages wherein different members of the collection bear different compounds from a combinatorial library. Larger collections are provided as well, for example collections that include at least 10, $10^2$, $10^3$, $10^4$, $10^5$, $10^6$, $10^7$ or more members or any number therebetween. Each replicable genetic compound in the collection can display multiple copies of the compound attached to it. In certain libraries, each replicable genetic package bears a different compound and harbors a different tag, such that there is a 1:1 correspondence between compound and tag. In other libraries, the same tag can encode for several compounds.

B. Types of Genetic Packages

A replicable genetic package means a biological complex comprising a nucleic acid, and at least one peptide encoded by the nucleic acid. Examples of replicable genetic packages include cells, spores, bacteria, viruses and bacteriophage. Thus, the particular replicable genetic package or collections thereof can be selected from any one of the foregoing and/or include different combinations thereof. Replicable genetic packages are capable of replication either by self-replication, in combination with a host and/or a helper virus, or by in vitro replication, transcription and expression.

Bacteriophage including phagemids are a preferred replicable genetic package. Preferred phage are the filamentous phage (e.g., M13, fd and fl) and phagemid vectors derived therefrom. See, e.g., Dower, WO 91/19818; Devlin, WO 91/18989; MacCafferty, WO 92/01047; Huse, WO 92/06204; Kang, WO 92/18619. Other phage of *E. coli*, such as T7 phage, or phage of other bacterial species can also be used. Filamentous phage are 6 nm in diameter and up to one micron in length. It has been used extensively in peptide phage display. Its surface consists of five coat proteins, two of which, pIII and pVIII, have been used to display peptide libraries. pIII, contains 406 amino acids and is present in three to five copies. The major coat protein, pVIII, which contains 50 amino acids, constitutes the bulk of the phage protein as it is present in approximately 2700 copies. The bacteriophage can also be a non-filamentous phage such as icosahedral phages T7 and lambda. The major coat protein of T7 phage is the gene 10 capsid protein, which contains 370 amino acids and is present in 415 copies.

In addition to phage, the replicable genetic package of the invention can include eukaryotic viruses, (e.g., the Moloney murine leukemia virus; see, e.g., Han, et al., Proc. Natl. Acad. Sci. USA 92:9747-9751 (1995)) or spores (e.g., spores from *B. subtilis;* see, e.g., Donovan, et al., J. Mol. Biol. 196:1-10 (1987)). A variety of different cells can also be used as replicable genetic packages in the present invention. Examples of suitable bacterial cells include, but are not limited to, *Salmonella typhimurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis,* and especially *Escherichia coli.*

C. Library Compounds

1. Types

The methods of the invention are typically used for screening compounds other than expressed polypeptides because expressed polypeptides can be screened by conventional phage display methods. Thus, as used herein the phrase "other than an expressed polypeptide" is defined, as noted supra, a compound other than a polypeptide, protein or peptide produced by translational expression of the nucleic acid (i.e., genome) of the replicable genetic package. In some instances, the compound attached to the replicable genetic package is a protein. In such situations, the protein can be attached by a peptide linkage (i.e., the amide bond formed as part of the protein backbone), while other proteins are attached via another type of linkage. Certain of these compounds include amino acids that are not included in naturally occurring proteins. The compounds can be of a variety of chemical types including, but not limited to, sterols, nucleic acids, derivatives of purine and pyrimidine bases, β-lactams, aromatic compounds, heterocyclic compounds, carbocyclic compounds, oligo-N-substituted glycines, polycarbamates, oligosaccharides, lipids and amino acids, and derivatives and combinations thereof. In some instances, the phrase other than a polypeptide can refer to small molecules produced by organic synthesis. Such small molecules can be attached to a polypeptide expressed by the replicable genetic package.

Compounds are often synthesized independently of the replicable genetic packages to which compounds are to be attached, but can also be synthesized on the replicable genetic package itself in some instances. Thus, compounds can be synthesized by conventional methods of combinatorial synthesis as summarized below. Such methods are subdivided into nonencoded and encoded methods. In the latter methods, compounds are synthesized on particles that also bear synthesis tags. These synthesis tags, if any, during compound synthesis are distinct from the tag, if any, contained in the replicable genetic packages.

2. Non-encoded Compound Libraries

Libraries of compounds are usually synthesized by solid phase chemistry on a support (e.g., a bead or particle). However, solution-phase library synthesis can also be useful. Strategies for combinatorial synthesis are described, for example, by Dolle and Nelson (*J. Combinatorial Chemistry* 1: 235-282 (1999) incorporated by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth.

Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. The size of libraries generated by such methods can vary from 2 different compounds to $10^2$, $10^4$, $10^6$, $10^8$, $10^{10}$, $10^{12}$ or $10^{15}$, or any range therebetween. If the synthesis is conducted on a support such as a bead, then the compounds are typically cleaved from the supports and individual library compounds stored separately.

3. Encoded Compound Libraries

An encoded library is one in which a synthesis tag is formed during the synthesis of the library compounds. This synthesis tag encodes at least one step in the synthesis of the library compound. An advantage of this approach is that the synthesis tag is designed to be easily decoded, thus permitting facile identification of the compound corresponding to the synthesis tag. Hence, the structure of the compound can be deduced from the synthesis tag rather than having to determine the structure of the compound directly, which, depending upon the type of compound, can be arduous and time consuming.

Preparation of encoded libraries is described in a variety of publications including Needels, et al. *Proc. Natl. Acad. Sci. USA,* 90: 10700 (1993); Ni, et al *J. Med. Chem.,* 39: 1601 (1996); WO 95/12608, WO 93/06121, WO 94/08051, WO 95/35503 and WO 95/30642 (each of which is incorporated herein by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first synthesis tag using different first monomer and synthesis tag combinations in each different reaction vessel; (c) pooling the supports; (d) apportioning the supports among a plurality of reaction vessels; (e) coupling to the first monomer a second monomer and coupling to either the solid support or to the first synthesis tag a second synthesis tag using different second monomer and second synthesis tag combinations in each different reaction vessel; and optionally repeating the coupling and apportioning steps with different tags and different monomers one to twenty or more times. The monomer set can be expanded or contracted from step to step; or the monomer set can be changed completely for the next step (e.g., nucleosides in one step and carbohydrates in another step).

The synthesis tags encode one or more reaction steps taken in synthesizing the test compound. For those compounds wherein the synthesis yields a single product in high yield (e.g., an oligonucleotide synthesis), the synthesis tag explicitly specifies one, and usually all, of the components of the compound and its structure. In some situations, for example, when only a small number of monomer units of an oligomer are varied, it is not necessary to identify all the monomers utilized in the synthesis, but only those monomers which vary among the oligomers. For other syntheses that give variable yields and frequently multiple products (such as regio- and stereoisomeric structures), a mixture of compounds is sometimes obtained on each bead. In such instances, the synthesis tag may not uniquely specify the chemical structure of the synthesize test compound. Instead, the synthesis tag encodes the synthetic protocol (e.g., reagents and reaction conditions) by which a test compound in a library was prepared.

Synthesis tags are selected to have a readily identifiable feature that is, for example, microscopically or otherwise distinguishable in shape, size, mass, charge, or emissions. This recognizable feature may arise from the spectral, chemical, electronic, or magnetic properties of the encoding tag, or from some combination of such properties. Through the use of synthesis tags to record the synthesis pathway that each member of a chemical library has taken, the structure of any chemical in the library can be determined from the synthesis tag.

Nucleic acids and inert hydrocarbons are examples of the type of molecules that have utility as synthesis tags in the present invention. Nucleic acids by virtue of the different bases and known chemistries regarding their attachment provide a natural and straightforward means for encoding the different synthetic steps. When decoding a nucleotide synthesis tag, several options are available. For example, the synthesis tag can be read directly from the bead by sequencing or hybridization. Alternatively, or in addition, a nucleic acid synthesis tag can be amplified (e.g., by PCR) to facilitate identification. Hydrocarbons provide another useful option, because their identity can readily be determined by a variety of well-known chromatographic techniques, for example, GC and GC/MS. Other options are described in Ohlmeyer et al (*Proc. Natl. Acad. Sci. USA,* 90: 10922-26 (1993); and WO 94/08051, each of which is incorporated herein by reference for all purposes).

The time at which the synthesis tag is attached to the support is not critical. For example, a synthesis tag can be attached immediately before, during, or after a round of monomer addition to compounds or other reaction, so long as such timing is compatible with the type of synthesis tag, modes of attachment, and the chemistries involved in preparing the library compound. The necessary encoding of the synthesis steps can be achieved using a single or multiple synthesis tags.

D. Linkers

1. General

A variety of linkers can be used to join replicable genetic packages and library compounds. Such linkers can be useful in providing distance between the replicable genetic package and the compound to avoid steric crowding that could prevent a recognition element (e.g., receptor or enzyme) to bind the displayed compound, thus generating false negative assay results. As used herein, a linker does not include moieties utilized simply to activate for reaction either an endogenous group borne by the replicable genetic package or an inherent functional group of the compound. When used in reference to a compound, an inherent functional group is one that is part of the compound as synthesized; the term does not include a functional group that is part of an activating group or linker incorporated or added to the synthetic compound. In some instances both the package and compound bear linkers. The association between such linkers can be either covalent or non-covalent.

2. Package Linkers

An optional linker can be attached to the exterior surface of the replicable genetic package to facilitate attachment to a library compound. Package linkers should be capable of forming stable complexes with the exterior surface of the replicable genetic package, as well as being capable of binding to a library compound (either directly or via a linker attached to the library compound).

As used herein, a package linker refers to an attachment moiety on the surface of the replicable genetic package that is not naturally occurring, recognizing that there can be some variation in expressed polypeptides that are displayed on the surface of different replicable genetic packages due to natural genetic variability in the replicable genetic package. Thus, a package linker encompasses amino acids and expressed polypeptides on the surface that have been derivatized or modified prior to attachment to a compound but not an amino acid or an expressed polypeptide as it exists naturally on the surface of the replicable genetic package. Such modifications can be introduced chemically, enzymatically or genetically.

One class of package linkers are those which are members of a binding pair. These linkers bind to compounds bearing the other complementary member of the pair. Certain linkers are expressed polypeptides displayed at the surface that are expressed from an exogenous sequence introduced into the replicable genetic package. Other peptides that can be used as suitable linkers include, but are not limited to, antibodies, peptide epitopes for antibodies, peptide substrates for enzymes (e.g., BirA and various kinases) and streptavidin. Other suitable package linkers include, for example, biotin and gold particles.

3. Compound Linkers

Compounds can be attached to the replicable genetic package through an inherent functional group or via an optional linker. In general, the compound linker is selected to have functionality that can react with or bind to a functional group on the replicable genetic package or linker attached thereto. If a pool of compounds (e.g., from a combinatorial library) is to be attached to replicable genetic packages, each compound can include the same linker to permit all the conjugation reactions to be performed under similar reaction conditions.

When compounds are to be attached to replicable genetic packages that bear one member of a binding pair at their surface, then the compounds are attached to the second member of the binding pair. Compounds and replicable genetic packages thus become attached through complementary binding pair members. Thus, for example, if the replicable genetic package includes a ligand-binding protein on the surface (e.g., streptavidin), the linker borne by the compound includes a ligand that binds specifically to the binding protein (e.g., biotin).

One or more additional bridging linkers can be used to increase the distance between the compound and the linker that ultimately becomes attached to the replicable genetic package. Such a linker is typically bifunctional (i.e., the linker contains a functional group at each end; one group is reactive with a functional group on the library compound, the second group being reactive with a functional group on the linker that binds to the package). The functional groups at each end can be the same or different. Examples of suitable linkers include straight or branched-chain carbon linkers, heterocyclic linkers and peptide linkers.

4. Reversible Linkers

Any of the foregoing linkers can be reversible linkers that can be readily cleaved under the appropriate conditions, thereby providing a facile way to release a compound from the replicable genetic package. This capability is important in some assays. NVOC (6-nitroveratryl-oxycarbonyl) linkers and other NVOC-related linkers are examples of suitable photochemical linkers (see, e.g., WO 90/15070 and WO 92/10092), as are nucleic acids with one or more restriction sites, or peptides with protease cleavage sites (see, e.g., U.S. Pat. No. 5,382,513). For cleavage during use, one selects a linker that is spontaneously cleaved under the conditions of the relevant assay (usually a physiological buffer).

Other exemplary linkers that can be employed in the present invention are available from Pierce Chemical Company in Rockford, Ill.; suitable linkers are also described in EPA 188,256; U.S. Pat. Nos. 4,671,958; 4,659,839; 4,414,148; 4,669,784; 4,680,338, 4,569,789 and 4,589,071; and in Eggenweiler, H. M, *Drug Discovery Today*, 3: 552 (1998), each of which is incorporated in its entirety for all purposes.

E. Tags

The replicable genetic packages of the invention optionally include a tag for use in identifying the library compound attached to the package. Typically, the tag is a heterologous nucleic acid sequence that is inserted into the nucleic acid or genome of the replicable genetic package or a separate vector harbored by the replicable genetic package. The heterologous sequence is sufficiently long to encode whatever information one seeks to record about a compound. In general (but not always) the tags will not be expressed as mRNA or expressed polypeptides. Thus, the tag typically is a nucleic acid segment other than a segment that encodes for a polypeptide displayed on the replicable genetic package. Furthermore, the code used normally is not the usual genetic code, i.e., the standard code in which a triplet of nucleotides encodes for an amino acid. Certain codes are simply used to indicate a symbol or value associated with a particular compound. In such instances, all that is necessary is that different packages harbor different tags, and that there is a different package available for each different compound or pool of compounds to be screened. Other codes are selected to record a particular structural step in the synthesis of a compound, while other codes are used to record one or more components of a compound. In other instances, the code can be used to record the complete structural identity of a compound.

The heterologous sequence can be flanked by other heterologous sequences that facilitate analysis of the heterologous sequence. For example, the heterologous sequence can be flanked with unique primer binding sites. In some methods, the heterologous sequence is flanked by a heterologous promoter (e.g., phage T7 promoter, T3 promoter and sp6 promoter) and a heterologous restriction site, thereby facilitating production of short transcript probes comprising or complementary to the heterologous sequence. In such instances, the heterologous sequence is sufficiently long so that a probe transcribed from the heterologous sequence can specifically hybridize with a complementary sequence under stringent conditions. For examples, lengths of 15 to 30 bases are suitable, although longer sequences can be used. Additional details regarding tags are set forth in the screening section below and in Examples 4 and 10.

When screens are conducted with replicable genetic packages that harbor sequences that allow for probe formation, hybridization analyses conducted with such probes can be facilitated using isothermal tags. Isothermal tags refer to nucleic acid sequences that have the same base composition but which differ in the ordering of the bases. Because they have the same overall base composition, isothermal tags have the same melting temperature. Consequently, the hybridization and washes conducted during hybridization analyses with the different probes can be conducted under the same conditions, thereby significantly simplifying the screening process. The use of such tags is described further in Example 10 infra.

IV. Methods of Preparing Replicable Genetic Packages

A. Attaching Compounds and Replicable Genetic Packages—Direct Chemical Attachment Compounds and replicable genetic packages can be directly conjugated through the reaction of an endogenous functional group that appears on the surface of the replicable genetic package and a functional group inherent to the compound. Typically, the reaction between such functional groups generates a covalent bond. Thus, as defined herein, direct chemical attachment refers to an attachment in which an endogenous group is joined to an inherent functional group borne by the compound. A covalent bond formed from such an interaction includes only atoms from the endogenous group on the replicable genetic package and the inherent functional group of the compound.

The exterior surface of the replicable genetic package allows for direct chemical attachment because it typically includes various functional groups to which the compound can be attached. For example, the exterior surface generally includes expressed polypeptides that present amino, hydroxyl, carboxyl and thiol groups which can serve as points of attachment.

The objective in direct coupling approaches is to develop chemical approaches that are compatible with the synthesis of large and structurally diverse small molecule libraries. As such, the methods should have an appropriate level of specificity to effect conjugation to replicable genetic packages in a controlled fashion, yet maintain enough generality so as not to obviate the use of a variety of synthetic chemistry methods during library construction. Chemical ligation strategies that utilize the chemical functionality already present at the exterior surface of replicable genetic packages are attractive because of the general utility of the methods.

Examples of suitable direct attachment methods are illustrated in FIGS. 2A-2D which illustrates the conjugation of small molecules bearing the appropriate functionality directly to residues within a phage coat protein. These include the acylation of lysine residues and free amino termini with an N-hydroxysuccinimide ester, use of carbodiimide chemistry to create an amide linkage between glutamate and aspartate residues, and free carboxy termini within the phage coat expressed protein and small molecules containing amines, and alkylation of cysteine residues with maleimide or iodoacetamide functional groups. While these particular examples show conjugation to phage, the methods are applicable to other replicable genetic packages displaying the same type of functionality.

B. Attaching Compounds and Replicable Genetic Packages—Attachment Via Linkers

Instead of being directly conjugated, replicable genetic packages and compounds can be attached via one or more linkers. The linkers can be useful for introducing certain functionality that facilitates the attachment process or can be used to obtain separation between compound and package.

1. Formation and Attachment of Package Linker with Chemical Methods

One option for chemically attaching a compound to a replicable genetic package involves the chemical formation of the linker or an attachment site at the exterior surface of the replicable genetic package. This can be done, for example, by derivatizing or modifying an endogenous functional group located at the exterior surface of the replicable genetic package. Typically, the exterior surface of a replicable genetic package includes a number of suitable functional groups. For example, the exterior surface generally includes expressed polypeptides that present amino, hydroxyl, thiol and carboxyl groups that can be derivatized or modified. Some modifications involve chemically modifying amino acids or segments of expressed polypeptides at the surface of the replicable genetic packages.

Figure 3A:
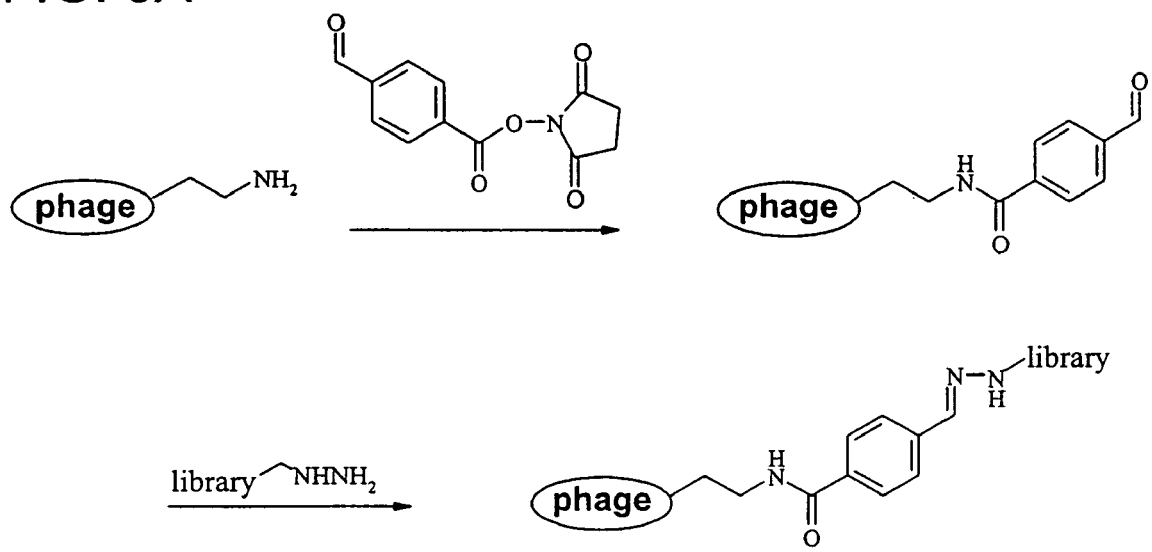
FIGS. 3A-3B depict strategies to effect the chemical conjugation of small molecule libraries to modified phage coat proteins.
Figure 3B:
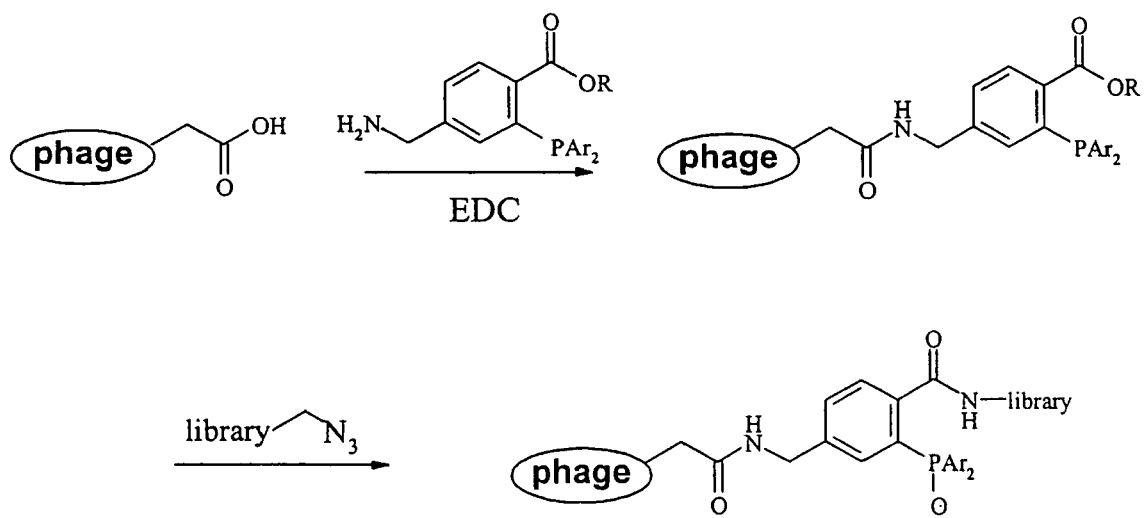

Specific examples illustrating this approach are shown in FIGS. 3A and 3B. These include displaying an aldehyde on the surface of phage, which undergoes a highly specific condensation with hydrazines, hydrazides, semi-carbazides and alkoxy amines to create a stable hydrazone or oxime linkage. In addition, the phage surface can be modified with an aryl phosphine that can condense with azides on compounds to form a highly stable amide linkage.

Instead of modifying an endogenous functional group, other conjugation methods involve chemically attaching a linker to an endogenous functional group borne by the replicable genetic package. Replicable genetic packages bearing the linker can subsequently be attached to compounds via the linker. As a specific example of this general approach, phage particles are reacted with an excess of NHS-biotin, which forms covalent bonds with free amine groups on the surface of the phage. The biotin on the exterior surface is then reacted with an excess of streptavidin to form a biotin/streptavidin complex. Unbound streptavidin is washed away before reacting the phage with a library member. The library member in this instance includes a biotin linker for attachment to the streptavidin/biotin complex formed on the surface of the phage. Methods involving the chemical attachment of biotin to the replicable genetic package are described further in Example 12 infra. Another alternative is to react an antibody with an appropriately activated functional group with the free amine on the surface of the phage. The antibody on the exterior surface of the phage can then be linked to a library compound including a hapten that has specific binding affinity for the antibody.

Figure 4:
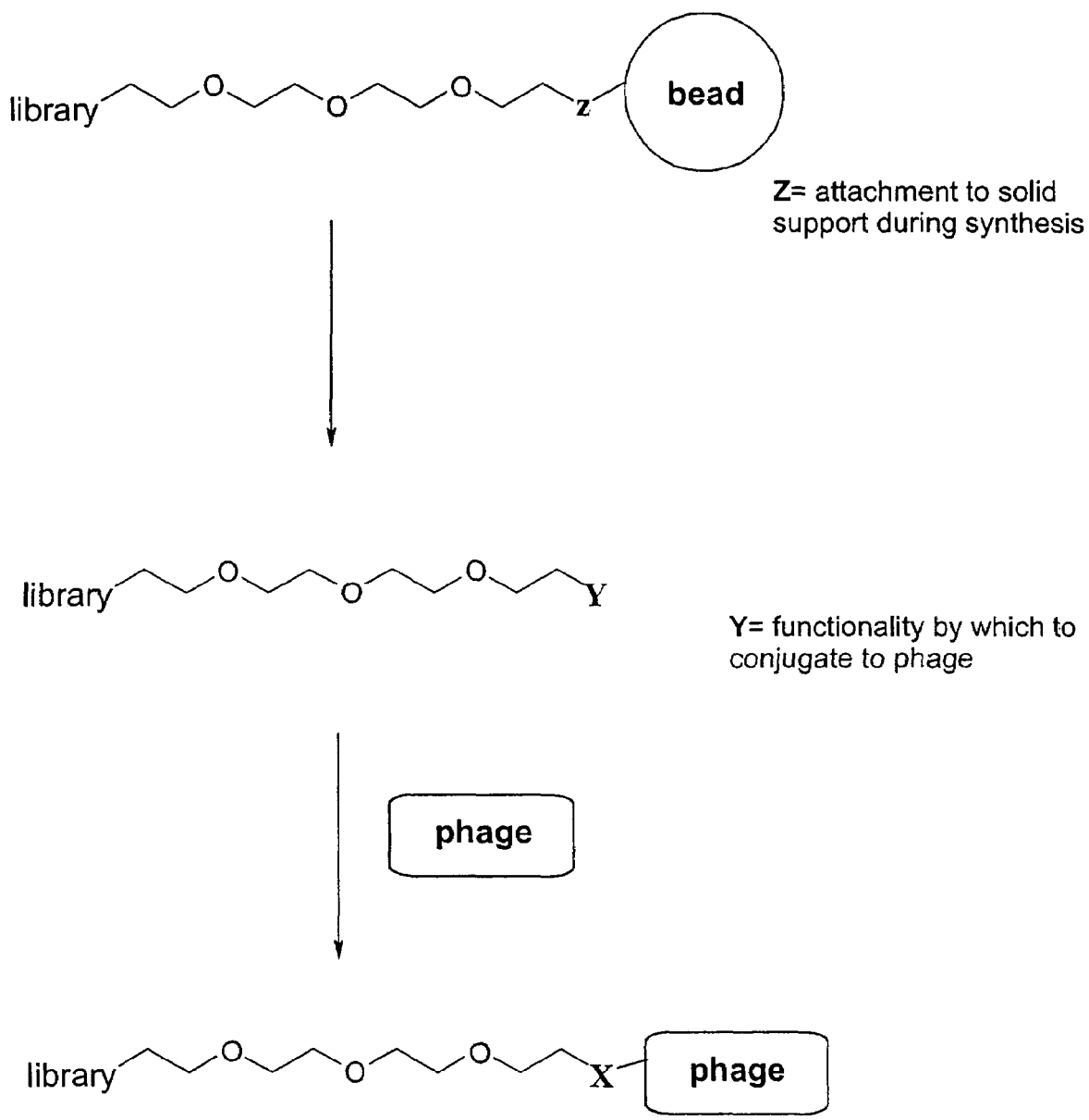
FIG. 4 illustrates a strategy utilizing solid phase attachment chemistry to access functionality to conjugate small molecule libraries to phage.

Other chemical approaches involve the attachment of a compound to an endogenous functional group on the replicable genetic package via a linker borne by the compound. In such instances, a functional group of the compound linker reacts with a functional group on the surface of the replicable genetic package. To increase the efficiency of the process of synthesizing small molecule libraries and their subsequent attachment to a replicable genetic package, the linker utilized to immobilize the compound during synthesis is preferably selected such that the linker can also be used in the attachment of the final compound to the replicable genetic package. In particular, the functionality by which small molecule libraries are tethered to a solid support should also serve as a site of attachment between the small molecules and the replicable genetic package. This strategy is outlined in FIG. 4. As illustrated in this figure, the functionality represented by the letter Z, utilized to attach the libraries to solid support, is transformed into functionality Y upon cleavage from the support. Functionality Y is then utilized to chemically ligate the small molecules to replicable genetic packages. Specific examples further illustrating this strategy are shown in FIG. 5, demonstrating how some of the attachment chemistries might be accessed upon cleavage of the small molecules from solid support.

2. Formation and Attachment of Package Linker with Non-Chemical Methods a. General Instead of chemically attaching a linker to the exterior surface of the replicable genetic package, the linker can be attached using recombinant and/or enzymatic methods. One approach is to enzymatically convert or modify an amino acid or expressed polypeptide displayed at the surface of the replicable genetic package to form an attachment site. Various recombinant methods can also be utilized. For instance, when the replicable genetic package is a phage, DNA encoding a protein linker can be cloned into the 5' end of the gene for one of the phage coat proteins (e.g., pIII, pVIII) that is contained in the phage genome itself or on a vector, (e.g., a plasmid).

Expression of the fusion gene results in a fusion protein that includes the expressed polypeptide encoded by the inserted sequence and the endogenous coat protein; this fusion protein is displayed on the exterior surface of the phage. Because there are multiple copies of each coat protein at the exterior surface of the phage, multiple linkers (and thus multiple compounds) are displayed at the surface. So long as the linker is not toxic to the host cell, the DNA encoding a protein linker can be directly inserted into the phage genome (as just noted, typically at or near the N-terminus of the genes for one of the phage coat proteins).

If toxicity is a concern, then filamentous phage engineered to produce a second copy of either gene III or gene VIII can be utilized. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, heterologous polypeptide sequences are cloned into phagemid vectors that encode a phage coat protein and phage packaging sequences but which are not capable of producing phage particles. Phagemids are transfected into cells and packaged by infection with helper phage. Use of phagemid system also has the effect of diluting fusion proteins formed from coat protein and expressed polypeptide with wild type copies of coat protein expressed from the helper phage. See, e.g., Garrard, WO 92/09690. In yet another approach, the linker sequence is inserted into a plasmid and placed under the control of a tightly inducible promoter. Suitable promoters include, for example, tet and araB.

Similar recombinant methods can be used with the other types of replicable genetic packages to obtain expression of a desired expressed polypeptide at the surface. For example, eukaryotic viruses (see, e.g., Han, et al., Proc. Natl. Acad. Sci. USA 92:9747-9751 (1995)) and spores (see, e.g., Donovan, et al., J. Mol. Biol. 196: 1-10 (1987)) have also been shown to be capable of displaying fusion proteins. The approach can also be utilized with cells by inserting the gene for the linker into a gene encoding an expressed polypeptide that is expressed on the surface of the cell. Details of expressed polypeptides are discussed by Ladner, et al., U.S. Pat. No. 5,571,698, and Georgiou, et al., Nature Biotechnology 15:29-34 (1997) and references cited therein. For example, the lamB protein of *E. coli* is suitable.

b. Covalent Attachment

One specific example of suitable linkers includes the display of enzymes that can be reacted with high affinity inhibitors (typically small molecules) that are incorporated into a complementary linker borne by the compound. The interaction of such inhibitors with the enzyme can be a non-covalent interaction, e.g. as in the interaction of a protease with a transition-state analog inhibitor, or more preferably, can be a permanent covalent interaction, as would be formed by a suicide substrate inhibitor of the enzyme. An example of the latter such interaction is the reaction of the enzyme β-lactamase expressed on the package with a penicillin sulfone derivative used as the compound linker (see, e.g., Vanwetswinkel et al, *Bioorg. Med. Chem.* 3:907 (1995)).

Figure 6:
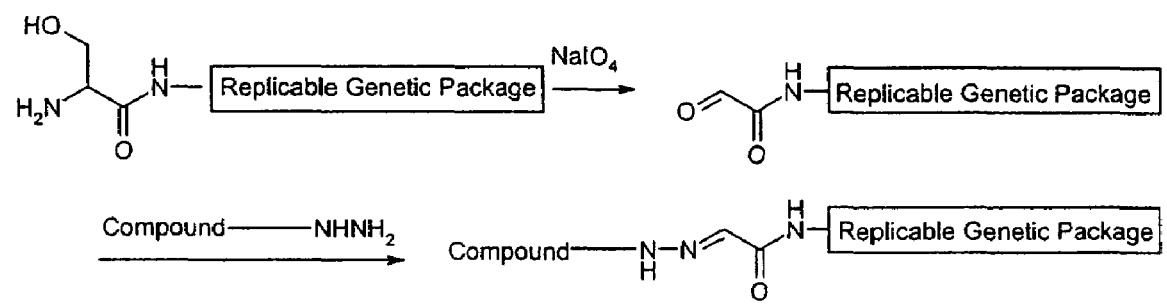
FIG. 6 illustrates one approach for joining a library compound and a replicable genetic package.

In other useful package linker/compound linker pairings, the package linker is an expressed polypeptide fragment that can be chemospecifically reacted under mild reaction conditions with the complementary compound linker. For example, as shown in FIG. 6, when the replicable genetic package is phage, expression of a recombinant pIII or pVIII molecule bearing an N-terminal serine residue can be converted by mild treatment with aqueous sodium periodate to a reactive N-terminal glyoxalamide moiety, that undergoes specific reaction with a compound bearing a hydrazine linker (e.g., see Rose, J. Am. Chem. Soc. 1994, 116, 30).

Similarly, as illustrated in FIGS. 7A to 7D phage expressing a recombinant pIII or pVIII molecule bearing an N-terminal cysteine residue on the surface can be reacted under mild conditions with various complementary compound linkers to form stable compound-bearing phage. Examples of such compound linkers include, for example: (i) an aromatic ortho-dialdebyde containing compound linker (FIG. 7A), (ii) a mono-aldehyde containing compound linker that reacts with the cysteine residue to form a thiazolidine ligation (FIG. 7B; see Zhang et al, Proc. Natl. Acad. Sci. USA 1998, 95, 9184), and (iii) a benzyl thioester containing compound linker according to the so-called method of "native chemical ligation" (FIG. 7C; see Cotton and Muir, Chem. Biol. 1999, 6, R247).

In yet another example involving phage, a phage expressing a recombinant pIII or pVIII molecule bearing a free cysteine residue that is accessible anywhere on the protein surface can be chemospecifically reacted under mild conditions with a complementary compound to form a stable compound-bearing phage, such as shown in FIG. 7D.

Certain methods involve combining of peptide display techniques and combinatorial chemistry methods to achieve a superposition of peptide and chemical diversity. Such methods initially involve generating a library of replicable genetic packages that display proteins according to any of the various known peptide display formats such as those described supra. The displayed proteins are subsequently modified by reacting small molecules prepared by synthetic methods to the displayed peptides or by directly synthesizing small molecules on the displayed peptides.

c. Non-Covalent Attachment

In certain recombination methods, the sequence for the protein streptavidin is inserted into the 5' end of the gene for a phage coat protein (e.g., pIII, pVIII) to yield phage displaying multiple copies of streptavidin. Library compounds including a biotin linker can then be joined to the streptavidin linker on the phage (see FIG. 1). Of course, genes for a variety of other proteins can be similarly inserted in place of the gene for streptavidin. For example, the gene for a single chain antibody can be inserted into the coat protein gene to display a fusion protein including the antibody. As described above, such a replicable genetic package can then be connected to a library compound having a hapten specific for the displayed antibody.

In a related approach, a 16 amino acid artificial biotinylation substrate sequence is cloned into one of the genes for the phage coat protein so that the substrate sequence is displayed at the surface. Phage are then treated with the enzyme Bir A which attaches biotin to a central lysine on each substrate peptide. (See, for example, U.S. Pat. Nos. 5,932,433; 5,922,545; 5,874,239; 5,723,584). Additional details regarding such methods are set forth in Examples 1 and 4 infra.

In still other methods, the gene inserted encodes for a peptide dimerization domain such that the replicable genetic package displays the dimerization domain at the surface. The compounds to be attached bear a complementary peptide dimerization domain. With such methods, the compounds and replicable genetic packages become associated through interaction of the dimerization domains. Another approach is to insert the gene for an enzyme into the genome of a replicable genetic package to achieve display of enzymes at the surface of a replicable genetic package. These enzymes can react with inhibitors to form stable non-covalent complexes.

Other attachment schemes utilize a particular compound linker to join the replicable genetic package and the compounds. For example, in one approach, compounds synthesized on a support are cleaved from the support and the resulting individual compounds attached to a large number of very small particles. The particles are then attached to the exterior surface of the replicable genetic package. The particles used in this approach typically range from approximately 1 to 50 nm, in other instances from 1 to 25 nm, and in still other instances from 5 to 10 nm. Examples of suitable small particles include colloidal gold particles. Given the small size of the particles, this approach enables many library compounds to be attached to the exterior surface of the replicable genetic package. This is of value when a pool of library compounds is contacted with the replicable genetic package since the small particles permit a plurality of different compounds to be displayed from the surface of the replicable genetic package (see below for more details on the pooling approaches).

3. Multivalent Display

Using the foregoing assembly methods, it is possible to prepare replicable genetic packages that display multiple copies of a single compound or multiple copies of multiple compounds. The display of multiple copies of either a single compound or multiple copies of different compounds allows multivalent binding assays to be conducted. Furthermore, such multivalent display enables the screening methods disclosed herein to identify compounds with low activity (e.g., binding affinity). Preparation of phage illustrates this aspect. Assuming that pools of compounds (10 to 100 compounds within a pool) are reacted with each phage and that 10% to 30% of the approximately 3000 pVIII molecules on a phage are populated with a compound, each phage can potentially display up to 100 copies of each library compound within the pool.

The multiple compounds are attached at attachment sites. An attachment site refers to a site that naturally appears on the surface of the replicable genetic package (i.e., an endogenous site) or to a site that is introduced using chemical, enzymatic or genetic techniques (i.e., an exogenous site) to the surface of the replicable genetic package. The attachment site allows for non-covalent interaction between the replicable genetic package and compound or can include functionality that allows for attachment of a compound to the attachment site.

Thus, multiple compounds can be attached by direct chemical attachment as described supra in which a replicable genetic package and multiple compounds become joined via formation of a covalent bond between an endogenous functional group expressed on the replicable genetic package and functional groups borne by the compounds. Another option is to derivatize different endogenous functional groups on the package prior to attaching the compounds. By selectively reacting different functional groups expressed on the surface of the replicable genetic package with different reagents, one can introduce different attachment sites onto the surface of the replicable genetic package. Alternatively, different encoding sequences can be inserted into appropriate regions (e.g., 5' region) of the genes for different expressed polypeptides to display different attachment sites on the surface. By displaying more than one type of functional group or expressed polypeptide on the surface in this manner, one can selectively attach different compounds at different locations on a single replicable genetic package. The display of multiple compounds can be useful, for example, in screening for compounds that both bind to a receptor, potentially resulting in synergistic binding.

Moreover, with phage, for example, one can selectively display multiple compounds on particular coat proteins (e.g., for phage fd, the coat proteins are pIII, pVI, pVII, pVIII, and pIX). The multiple compounds can be displayed on a single coat protein, or one or more copies of each compound can be displayed on multiple coat proteins that each have the same sequence. Alternatively, one or more compounds can be displayed on each of a plurality of different coat proteins that have different sequences. The multiple compounds that are displayed can be the same or different, allowing for an even greater number of display formats. One way in which compounds can be selectively displayed is to utilize different functional groups on the surface of the phage to control the placement of the compounds. For example, thiols and amino groups on the surface can be selectively attached to different compounds by using compounds that bear functional groups that preferentially react with a particular one of the functional groups displayed by the phage.

In like manner, multiple attachment sites having the same or different chemistry can be selectively utilized to attach compounds at particular coat proteins. For instance, one or more copies of attachment sites having the same functionality may be present or can be introduced into a single coat protein or several coat proteins that each have the same sequence. With other packages, one or more copies of attachment sites having the same functionality are present or introduced in each of a plurality of different coat proteins that have different sequences. Alternatively, one or more copies of attachment sites of differing functionality may be present or can be introduced on one or more coat proteins that share the same sequence. Finally, one or more copies of attachment sites of differing functionality may be present or can be formed at each one of a plurality of coat proteins having different sequences.

4. Replicable Genetic Package Immobilization and Release Strategies

The attachment process in some instances is performed by initially immobilizing the replicable genetic package on a support, typically via a reversible linker that is cleavable. The compound is then attached to the immobilized replicable genetic package, unreacted compound washed away and the replicable genetic package displaying the compound released by cleaving the linker. The resulting package can then be used in assays. Additional details regarding this method are provided in Example 11.

B. Tagging Replicable Genetic Packages

1. Insertion of Heterologous Sequence to form a Package Library

As indicated above, some replicable genetic packages of the invention include a tag to facilitate the identification of library compounds that appear from assay results to have a desired characteristic. In some methods, the tag is a heterologous nucleic acid that is inserted into the genome of the replicable genetic package. In such instances, a degenerate nucleic acid mixture is inserted into a convenient location of the genome of the replicable genetic package. By inserting a degenerate nucleic acid mixture into a population of packages, a library of packages can be prepared in which each member contains a different heterologous sequence.

While in some methods only a heterologous nucleic acid sequence is inserted into the genomic DNA of the library member, in other methods an inducible promoter and a restriction site are also inserted into the genome. The promoter and restriction site are inserted so that they flank the heterologous nucleic acid; the promoter is also positioned so that it is operably linked to the heterologous nucleic acid. The promoter initiates transcription of the inserted heterologous sequence to produce a probe that lacks upstream package (e.g., phage) sequences. By cleaving the DNA at the restriction site prior to transcription, the transcribed probe also lacks downstream package sequences. Thus, the RNA probe resulting from transcription of the heterologous nucleic acid sequence primarily contains only the sequence unique to a particular package clone. As described in more detail below, this probe can be utilized to identify those compounds that produce positive assay results.

In preparing clones in this manner, the heterologous nucleic acid, the promoter and the restriction site are all typically inserted at sites that do not create any deleterious effects on the replicable genetic package (and in the case of viruses, no adverse effects on host physiology), such as non-coding sites for example. When phage are used, one useful site for insertion of the heterologous site is at the C-terminus of the gene for the pill or pVIII coat protein. If promoters are inserted, suitable promoters include, for example, the phage T7 promoter, the T3 phage promoter and the SP6 phage promoter.

As indicated above, the heterologous sequence is typically 15 to 30 bases long. This length is sufficiently long to ensure that during hybridization reactions the probe generated from the heterologous sequence can specifically hybridize with a complementary sequence, even in complex mixtures. A nucleic acid this long also provides enough sequence complexity ($4^{15}$ to $4^{20}$=30 million to 1 billion members) that large numbers of randomly-picked clones from a population of clones are very unlikely to carry the same (or even similar) sequences.

With certain collections of replicable genetic packages, the heterologous tags inserted into the different packages are selected to be isothermal. As indicated supra, this involves introducing sequences that have the same base composition, thereby resulting in tags that have the same melting temperature. The preparation of isothermal tag sequences is described in greater detail in Example 10.

2. Transformation of Host Cells

When the package library is a phage library, the phage library is used to transform host cells so that a population of each clone can be formed. The transformed host cells optionally include a vector such as that described above that includes a fusion gene for a phage coat protein and a protein linker so that the new phage produced through assembly in the host cell display a linker at the surface (alternatively, such a fusion gene can be formed in the phage genome). Infected host cells are plated out as individual colonies. Each colony is picked and separately grown, typically in separate wells on a multi-well plate (e.g., a 864-well plate, each well having a 20 µl volume). Individual colonies can be picked and placed manually or automated using commercially available systems (e.g., QBot). Such systems allow the facile production of 10 to 100 multi-well plates or more. Each colony is grown under suitable conditions for expansion. Bacteria are subsequently removed using standard filtration or centrifugation methods, thus leaving an encoded phage library in the plates—each well of the multi-well plate containing a single clone. Such plates are referred to as "master plates."

A variety of different host cells can be transformed with the phage library members. Examples of suitable host cells include *E. Coli* (for specific examples of suitable strains of *E. coli*, see, for example, Peters, et al., J. Bacteriology 176:4296-4305 (1994)).

V. Screening Methods—No Tags

A. Establishing a Correspondence Regime

A correspondence regime refers to a system that allows one to keep track of which replicable genetic package bears which compound so that the identity of a compound showing activity can be identified. A library of compounds to be tested can be formed in the following manner. Replicable genetic packages (often including a first linker attached to the exterior surface of the package as described above) are placed in an array, typically the wells of a multi-well plate. An individual member from a library of compounds is incubated separately with the replicable genetic packages to form a plurality of replicable genetic packages displaying different compounds other than expressed polypeptides, each well containing a replicable genetic package that displays a different compound. The compounds can be from a known array such as a parent plate of compounds that have been cleaved from the support (e.g., a bead) upon which they were synthesized; alternatively, the compounds can be compounds severed from stochastically chosen supports, where the supports remain spatially arrayed for future identification.

Instead of contacting packages with a single library compound member, small pools of library compounds can be contacted with the replicable genetic packages, such that each well contains a replicable genetic package that displays multiple compounds. This significantly increases the efficiency of the screening process. If pools of library compounds are reacted, the pools typically contain less than 10, 25, 50 or 100 different compounds, although larger and smaller pools can also be used. During the contacting step, which compound or pool of compounds is added to each array location is tracked.

Assays can also be conducted using a pool of compound-bearing replicable genetic packages. In such instances, the particular replicable genetic packages pooled are tracked such that replicable genetic packages from a pool showing activity can be individually reassayed to identify the active compound(s) in the pool.

Replicable genetic packages can be designed to display multiple copies of a single compound or compounds per package by providing multiple binding sites per package. In instances in which a single compound is added to a group of replicable genetic packages, each replicable genetic package contains multiple copies of a single compound. When a pool of compounds is attached to a clonal isolate of packages, a single package in the isolate can display more than one type of compound. An excess of compound is added to the reaction mixture. Typically, approximately $10^6$ to $10^8$ replicable genetic packages are incubated with a large excess of compound(s). The concentration of compounds usually is more than 1 nM, often greater than 1 µM, and sometimes as more or more than 1 mM.

B. Screening

An aliquot of replicable genetic packages displaying a compound or multiple compounds is taken from a location in the array and assayed to determine whether the compound(s) on the packages taken from that particular location have a desired characteristic. The process is sequentially repeated with the packages at the other array locations. Because the location from which an aliquot is taken is noted prior to conducting the assay, it is possible to identify those array locations containing a compound or compounds that have the desired characteristic being assayed for. Since the compound or compounds added to each array location is also known, the identity of the compound can be established. In addition to assay of compounds in arrays, aliquots can be taken from the arrays and mixed for screening.

C. Compound Identification

In sequential methods such as those just described in which each replicable genetic package contains a single type of compound, the structural identity of the compound can be determined directly if the identify of the compound was ascertained prior to the assay. Even if the identity of the compound was not determined prior to forming the display package, the compound can be readily identified using standard analytical techniques such as mass spectrometry (MS), gas chromatography-mass spectrometry (GC-MS), infrared spectroscopy (IR), high performance liquid chromatography (HPLC), and/or nuclear magnetic resonance spectroscopy (NMR). If the compound was prepared on a support with a synthesis tag, the tag can be decoded to reveal the structure of the compound.

When pools of compounds are reacted with the replicable genetic packages so that they display different compounds, a subsequent round of screening is necessary to identify those compounds within the group of compounds that have the desired characteristic. For example, because the pool of compounds added to the packages at any array location is known, it is possible to individually reassay each compound in the pool of compounds shown in the initial assay to include at least one compound with the desired characteristic. Thus, for example, if array location 10 contains packages displaying compounds 50-60 and an aliquot of compound bearing packages from this location produces a positive assay result, compounds 50-60 are individually contacted with replicable genetic packages in separate array locations and then sequentially assayed in a second round of screening to identify which of the eleven compounds have the desired characteristic.

To ensure accuracy in the assay results various controls may be performed in parallel with the assays of the library compounds. For example, as a negative control, assays may be conducted with replicable genetic packages lacking a linker to which a library compound can attach (i.e., the assay is conducted with a replicable genetic package that lacks a library compound). As a positive control, a compound known to have the characteristic that is being screened for can be displayed from a replicable genetic package and assayed to ensure that a positive result is obtained.

VI. Screening Assays—with Tags

A. Correspondence Regime

Assays utilizing tags use the master plates described above in which cloned packages are stored in individual locations in an array (e.g., wells of a multi-well plate), each location including a population of cloned packages containing a unique heterologous sequence that encodes for the compound(s) displayed from the package. Separate aliquots are typically removed from the each of the array locations and individually spotted on a membrane to also form an "archival grid". The archival grids are arrayed such that each spot on the grid can be tracked or correlated with its corresponding location on the master plate. Many such archival grids can be routinely prepared using available automated and robotic spotting technologies.

To associate a clone with a library compound, library compounds are arrayed in separate locations, generally within the wells of a multi-well plate. As indicated above, the compounds may be from a known array such as a parent plate of compounds that have been cleaved from the support (e.g., a bead) upon which they were synthesized; alternatively, the compounds may be compounds severed from stochastically chosen supports, where the supports remain spatially arrayed for future identification.

Aliquots of packages taken from the master plate array are transferred to the wells containing library compounds so that each location in the array contains an aliquot of a single library compound and an aliquot of a unique clone package. The aliquots are transferred such that the clone package and library compounds remain spatially segregated and kept in registration with the array that contains the clones. As described above, when the clone package and library compounds are contacted, a sufficient excess of library molecules is contacted with the clone package to occupy the desired number of linker sites on the replicable genetic package.

B. Screening

The compound-bearing packages are then screened as individual entities or, more typically, pooled into complex mixtures for screening. If pools of packages are screened, a subsequent round of screening is performed with individual packages from a pool showing activity to identify which replicable genetic package in the pool bears the compound responsible for the observed activity. Pooling of aliquots can be performed using convention multichannel pipettors. The resulting compound-bearing packages are then ready to be assayed.

In addition to using pools of packages to increase screening efficiency, the capacity of the screening process can be greatly amplified by reacting each clone package with a pool of library compounds rather than a single compound. In this way, each package displays multiple compounds rather than a single compound. As described for the non-tag screening methods, in the pooled compound approach, typically 10, 25, 50 or 100 different compounds are reacted with the clone packages. If a package displaying different compounds produces a positive assay result, a second round of screening is necessary to identify which of the compounds in the pool have the desired characteristic.

If pools of 10 compounds are reacted with each phage clone and 10,000 phage clones are arrayed in multi-well plates, the method just described can be used to readily screen $10^5$ compounds. Since phage master plates can be used repeatedly, the methods of the invention can be easily scaled to allow rapid screening of greater than $10^6$ synthetic compounds.

After an initial round of screening, further enrichment for positive compounds can be achieved through additional rounds of screening. Although amplification of the replicable genetic packages between rounds is typically not done, multiple rounds of screening can be performed to achieve optimal enrichment of positive clones by starting the screening process with excess of each compound-bearing package. After the final round of screening, positive compound-bearing packages are expanded. In the case of phage, the positive clones are infected into a host such as *E. coli* and plated under selection.

C. Compound Identification

1. Sequencing Tag

The tag can be used to identify the compound utilizing several different approaches. When the package contains a heterologous sequence but lacks the other elements necessary to produce a probe from the heterologous sequence, the compound can be identified by sequencing the heterologous nucleic acid inserted into the genome of the clone package. Sequencing can be done before screening, but usually is done after screening. Sequence determinations can be performed using standard automated sequencing equipment and technologies. Thus, when individual (or small pools of) library compounds are joined to the clone packages, each library compound (or small pool of compounds) becomes associated with a particular known heterologous sequence. Thus, by sequencing the heterologous sequence of compound-bearing packages that give positive assay results, it is possible to unambiguously identify the compound (or pool of compounds) having the desired characteristic. As described above, in pooled approaches, a second round of screening is performed to identify which members of the pool have the desired characteristic.

2. Using Tag to Generate Hybridization Probe

When the clone packages include a promoter and appropriate restriction site to generate a probe, it is not necessary to sequence the heterologous sequence either before the packages are contacted with library compounds or after an assay has been performed. Instead, probes from packages bearing compounds with the desired characteristic are generated, labeled and used to probe the archival grids that contain sample dots for each of the compound-bearing packages that were prepared. Spots containing packages that contain heterologous sequences that specifically hybridize to the labeled probe can be identified from the bound label; it is these packages that display compounds with the desired characteristics. Since the compound or compounds added to any genetic package is known based upon the correspondence regime described above, the identity of compounds having the desired characteristics can be established. If the structural identity of the compounds was not previously determined, it can be determined using conventional analytical techniques such as those described above (i.e., MS, GC-MS, HPLC and NMR, for example). If the compound was synthesized on a support that included a synthesis tag that encodes at least one step of the synthesis, the synthesis tag can be decoded using the techniques described above to identify the active compound.

The probes can be prepared from individual clones and hybridized as individual clones, prepared from individual clones and then mixed, or prepared in batch. One approach for preparing individual phage clones initially involves picking 100 colonies and inoculating each clone into a 4 ml culture tube for expansion of the clone and growth of the phage. A set of 10 "clone arrays" or "clone grids," are prepared from the phage samples. Each of these is a 10×10 array of the 100 expanded clones. Ten of the clones are chosen for labeled probe preparation. Once labeled, each of the probes is hybridized under the appropriate stringency condition against the clone array to determine the frequency of each clone's appearance in the positive clone picks. Based upon this frequency information, a determination is made regarding the number of positive clones from which probes should be prepared for use in hybridization experiments against the heterologous sequences contained in the compound-bearing phage spotted in the archive grids. Further details regarding one approach for probe preparation and labeling is set forth in Example 10.

VII. Types of Assays

A variety of different assays can be performed with the replicable genetic packages of the present invention. The assays can also be performed with peptide display libraries. For instance, a number of different protein binding assays can be performed. Examples of such assays include, assays to identify novel nucleic acids capable of binding to a protein, assays for drug derivatives that are able to bind to a receptor, and assaying for compounds capable of being transported into a cell via a transport protein. Assays can also be performed to determine the epitope that is recognized by an antibody. Other examples of protein binding assays include screening for compounds that can either antagonize or agonize a receptor. Other types of assays can be performed as well, including for example, screening for compounds having antibacterial activity and compounds that are substrates or inhibitors of enzymes.

Certain features of the replicable genetic packages make them useful in such assays. Most notable among these is the ease of quantitation, sensitivity of detection, and ability to incorporate large amounts of information in the nucleic acid or genome of the replicable genetic package. For example, most viruses and phage can be quickly and accurately counted by the process of titering—growing plaques on host cells, each plaque representing a single viral particle from the analyte, and counting the plaques. In principle, the sensitivity of detection is a single particle—considerably more sensitive than available with most synthetic detection schemes using other types of particles (e.g., nanoparticles). Moreover, detection can usually be accomplished from a dilute and complex medium, such as a tissue fraction. The ability to easily encode additional information in the nucleic acid or genome of the replicable genetic packages allows individual packages to be tracked as each moves through a biological system, a goal that is considerably more difficult to achieve with synthetic particles.

A. Receptor Binding Assays

1. ELISA

One approach for screening library compounds for those capable of binding a particular receptor utilizes known enzyme-linked immunosorbent assay (ELISA) methods. For instance, a receptor of interest (or a cell expressing the receptor of interest) can be immobilized on a solid support according to known procedures. An aliquot of a compound-bearing package is withdrawn from an array location such as described above and contacted with the immobilized receptor under conditions conducive to specific binding. Unbound compound is rinsed away. Binding of compound to the immobilized receptor can be detected by adding labeled anti-package antibody to the assay mixture to bind to packages immobilized to the support.

As described above, the assays are typically conducted using multi-well plates, in which each well contains the immobilized receptor of interest. Which compounds bind to the receptor of interest can be determined according to the correspondence regimes set forth above. If the package displays multiple different compounds, a second round of screening is necessary to identify which of the displayed compounds is in fact active.

The general ELISA method just described can be modified to enable multiplex analyses to be conducted. In such multiplex assays, multiple different receptors are placed in a single assay location (e.g., a well in a multi-well plate) so that binding of compounds to multiple different receptors is assayed simultaneously. In certain multiplex methods, each of the different receptors is attached to a different type of support, each type of support being distinguishable from the other support types. For instance, the supports may differ in size, shape or be labeled with different labels (e.g., different fluorescent dyes). Confocal or semi-confocal microscopy can distinguish between the different support structures and thus can identify which of the receptors is bound to a compound. The confocal and semi-confocal fluorescent microscopy equipment necessary to conduct such assays is commercially available from either Perkin Elmer (FMAT instrument) or Cellomics.

2. Binding/Elution Approaches

Another approach, typically utilized when the packages include a tag, involves the direct binding of pools of compound-bearing packages against an immobilized receptor and subsequent elution (see, for example, Cwirla, et al., Proc. Natl. Acad. Sci. USA 87:6378-6382 (1990)). Incubation of the pools of compound-bearing packages with the desired immobilized receptor is generally performed in the well of a multi-well plate. Unbound phage are washed away. Bound phage are subsequently eluted at low pH or under other conditions that disrupt specific binding between a compound displayed on a package and the immobilized receptor. When phage are utilized, eluted phage are then used to infect a host cell (e.g., E. coli) and then plated out as individual colonies. Individual colonies are picked and placed into separate wells either manually or, more typically, with a commercial system (QBot) and grown.

Compounds borne on packages that yield positive assay results can be identified through standard analytical techniques or, for packages carrying a heterologous sequence tag, by sequencing the tag or generating a probe from the tag that can be used to probe the archival plates as set forth above.

3. FACS

Another option for assaying for receptor binding is to contact the multivalent packages with fluorescently labeled receptors. The packages are allowed to form a complex with the receptors and then washed to remove unbound or non-specifically bound receptors. A FACS instrument is then utilized to identify and physically isolate individual packages to which a fluorescent receptor is bound.

B. Assays for Cellular Transport

1. General

Active transport of compounds into or through cells typically occurs by carrier-mediated systems or receptor-mediated systems. Carrier-mediated systems are effected by transport proteins anchored to the cell membrane and are thought to function by transporting their substrates by an energy-dependent flip-flop mechanism. In receptor-mediated transport systems, substrate binding triggers an invagination and encapsulation process that results in the formation of various transport vesicles to carry the substrate into and through the cell.

This process, known as endocytosis, is often initiated by the binding of a ligand to a cell surface receptor (receptor-mediated endocytosis), and results in the uptake of extracellular materials, including fluid, dissolved solutes, and particulate matter. All eukaryotic cells undergo a continuous process of vesicle formation at the cytoplasmic side of the plasma membrane. The resulting membrane-enclosed vesicles are of a variety of sizes and compositions, generally of diameters of ~50 to 200 nm, enclosing volumes of roughly $10^{-20}$ to $10^{-17}$ liters ($10^7$ to $10^{10}$ $A^3$). Following endocytosis, the vesicles are directed to any of a number of cellular locations. The pathway and ultimate destination are directed by a variety of signal motifs present in the cytoplasimic, transmembrane and extracellular domains of the proteins located on the vesicles, and, in some cases, by the non-protein membrane components of the vesicles.

In polarized cells, such as epithelial and endothelial cells, the vesicles may be transported from one side of the cell to the other, a process of transcellular transport known as transcytosis. The vesicle docks and fuses with the plasma membrane and the contents emptied to the extracellular compartment. Polarized cells in which such transport occurs are present in many tissues. In all epithelial layers, the layers of cells separating the body from the outside world, the cells are polarized. Epithelial cell layers are characterized by the presence of tight junctions that form an effective seal between all the cells of the layer. It is this seal that divides the cells into an apical (outside) and a basal (inside) surface. The areas between the cells on the inside side are lateral; hence, the entire inside surface of the epithelial cell is known as the "baso-lateral" surface. The cytoskeletal structure, which is connected to the sites of the tight junctions, serves as an internal indicator of the orientation of the cell, and provides a signal to guide the proteins and organelles to their appropriate location in the polarized cell.

The foregoing pathways can be utilized for the delivery of foreign materials into or through cells for purposes of therapeutics, diagnostics, intracellular monitoring, and so on. Agents that can be delivered by these routes include small molecules, macromolecules, and particles. For delivery of agents by transcytosis, pathways with particular features are chosen. For example, to deliver drugs across the intestinal epithelium, one prefers a pathway with a reasonably high capacity of transport. In the intestine, most of the known pathways directed from apical to basal-lateral (lumen to blood) are of limited capacity and generally not optimal for drug delivery.

The replicable genetic packages described herein (compound-bearing packages) can be utilized in assaying transporter proteins. Because of their relatively large size, the compound-bearing packages are typically utilized in assays of endocytotic and transcytotic mechanisms because these processes by virtue of their mechanism of action accommodate the transport of particles. Hence, the methods described in this section can be utilized to discover novel transport pathways, and for readily quantitating the capacity for transport of known or novel pathways. Furthermore, the methods can be used to identify the specific receptors that mediate the transport event. Additionally, the methods can be performed to identify ligands that engage and activate the receptors. The methods are applicable for use in vitro (e.g., with cultured polarized cells), ex vivo with an excised tissue (e.g., an isolated section of small intestine), and even in vivo, as might be done in the small intestine of a living animal.

Replicable genetic packages (e.g., viral and phage particles) are an effective surrogate for methods that utilize nanoparticles in the assay of the disposition and transport of nanoparticles in endocytotic and transcytotic pathways since they can assume a variety shapes, and have dimensions of 20 to 200 nm, similar to the size range of nanoparticles that are utilized in studies of endocytotic and transcytotic transport. While certain of the methods are described primarily with respect to phage, it should be understood that some methods can be conducted with other types of replicable genetic packages.

2. Methods for Assaying Endocytosis and Transcytosis a. General

Assays of endocytosis and transcytosis can be conducted with various replicable genetic packages such as a series of bacteriophage with different shapes, sizes and other relevant attributes for this purpose. A primary feature of the methods is the use of the outer surfaces of the phage to deploy a variety of molecule types as potential ligands of the receptors mediating transport. The phage are produced as populations, or libraries consisting of many members of each of many clones. The members of each clone contain a unique nucleic acid tag which unambiguously distinguishes that clone from all others. A single phage particle can be detected and identified as member of a specific clone by growth (an thereby amplification) on host bacterial cells; thus phage provide a uniquely sensitive analytical tool.

In the present method, the phage are engineered to carry foreign compounds attached to their surfaces according to the various methods discussed herein. Each phage carries one to many copies of a single compound species, or in some cases several to many different compound species. All members of a clone carry the same compound, or set of compounds, which corresponds to the unique oligonucleotide tag sequence carried in the phage genome of all members of that clone. The compounds on the surfaces of the phage are of several types: peptides, comprised of any natural or unnatural amino acids, 3 to 100 residues in length; non-peptides; synthetic compounds constructed from a large variety of building blocks; combinations of peptides and non-peptide compounds; macromolecules such as proteins, carbohydrates, nucleic acids, and the like. Certain specific types of proteins, such as antibodies are of special utility here.

The methods generally involve contacting libraries of phage clones representing many different displayed compounds with the targeted cell population under conditions allowing endocytosis/transcytosis to occur. After an appropriate incubation time, the compartment of the cell or tissue that serves as the desired destination of the pathways of interest are analyzed for the presence of phage delivered via an endocytosis/transcytosis pathway. Such analysis can be performed in a variety of formats. For example, fluid from the destination compartment (the blood for example) can be taken and placed on a lawn of host bacteria to produce phage plaques—each plaque representing a single, successfully transported phage particle. Each plaque can be isolated, expanded and sequenced to specify the nucleic acid tag and assign the plaque to a particular phage clone. Alternatively, the plaques can be identified in situ by a process of hybridization with labeled oligonucleotides (see section on tag decoding) to assign and quantify the members of each clone. This assignment allows determination of the compound initially placed on that phage clone.

Certain methods are conducted with compound-bearing packages that bear a reporter capable of generating an optical signal. The reporter can be attached to the compound (either directly or via a linker) or attached to the surface of the package itself. The methods generally involve contacting one or more cells expressing one or more transporter proteins with a replicable genetic package of the type disclosed herein. Often contacting is performed within the wells of a microtiter plate. After incubating for a period sufficient to permit transport or binding of the compound, the location of signal from the reporter is detected. Detection of the signal at a location that indicates that a package has passed through a cell indicates that the package bears a compound that is a substrate for a receptor-mediated transporter protein expressed by the cell.

A reporter, if utilized, can be attached to the compound (either directly or via a linker) or attached to the surface of the package itself. An example of a suitable attachment point is the N-terminus of the coat protein pIII. Thus, for example, if pIII provides an attachment site for the reporter, library compounds can be displayed on pVIII. As a specific example, an epitope peptide sequence (e.g., YGGFL; SEQ ID NO:7) can be installed at the very N-terminus, thus resulting in this sequence being displayed upon expression. The epitope peptide can be labeled by reacting the peptide with a labeled antibody (mAb 3E7, for example, when the epitope sequence is YGGFL;SEQ ID NO:7).

Additional details regarding methods of assaying transport proteins utilizing compound-bearing particles is described in copending and commonly owned U.S. application Ser. No. 09/661,927, entitled "Substrates and Screening Methods for Transport Proteins," filed Sep. 14, 2000, and having attorney docket number 019282-000110US.

b. Exemplary In Vitro Assay Methods

Figure 8:
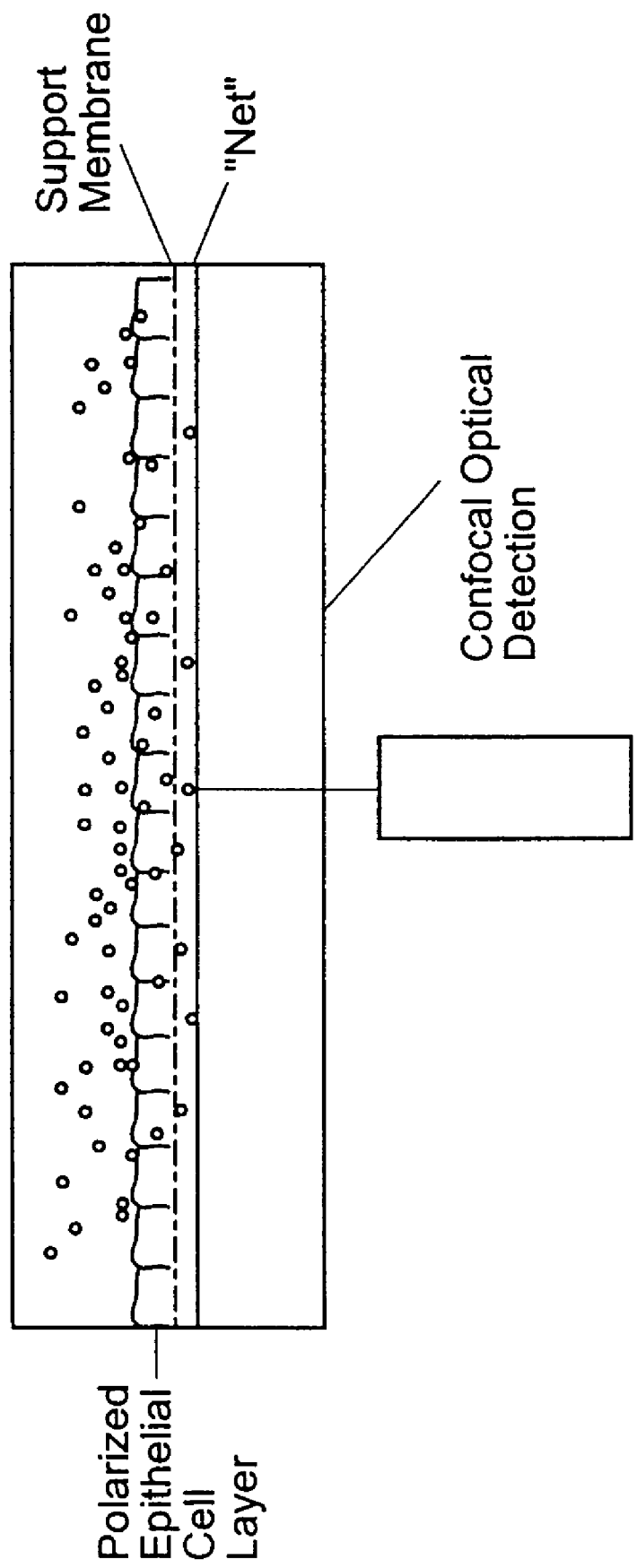
FIG. 8 depicts a two-membrane system (a transwell) for assaying for transport through a cell.

One assay method designed especially to screen for compounds capable of being transported through a cell utilizes a two membrane system (see FIG. 8). The first membrane or upper membrane is a porous membrane that includes pores that are larger than the compound-bearing packages being screened; this membrane is located within an apical chamber. A monolayer of polarized cells is placed on this upper membrane. A second or lower porous membrane is positioned under the first membrane and is structured to retain any complexes capable of traveling through the polarized cells and through the pores in the upper membrane. This membrane is part of a basal chamber. When the compound-bearing package is a phage, passage of a package through the cell monolayer and the permeable first membrane in the apical chamber and into the basal chamber can be detected by standard titering protocols which are described in further detail in Examples 2 and 5.

If the compound-bearing package also bears a label as described supra, internalization of a complex can be detected by detecting a signal from within a cell from the reporter. The reporter can be a label such as a fluorophore, a chromophore, a radioisotope, a magnetic particle or an electron dense reagent. The reporter can also be a protein, such as green fluorescent protein or luciferase expressed on the surface of the replicable genetic package. Confocal imagining can also be used to detect internalization of a package as it provides sufficient spatial resolution to distinguish between fluorescence on a cell surface and fluorescence within a cell; alternatively, confocal imaging can be used to track the movement of packages over time. In yet another approach, internalization of a package is detected using a reporter that is a substrate for an enzyme expressed within a cell. Once the complex is internalized, the substrate is metabolized by the enzyme and generates an optical signal that is indicative of uptake. Light emission can be monitored by commercial PMT-based instruments or by CCD-based imaging systems.

Movement of packages through the layer of cells on the transwell system described above can be observed with confocal microscopy, for example. Alternatively, movement of packages through cells can be monitored using a reporter that is a substrate for an enzyme that is impregnated in a membrane supporting the cells. Passage of a package bearing such a substrate generates a detectable signal when acted upon by the enzyme in the membrane. This assay can be performed in the reverse format in which the reporter is the enzyme and substrate is impregnated in the membrane.

C. Exemplary In Vivo Assays

The compound-bearing packages disclosed herein can also be used in in vivo screening methods to identify compounds that are substrates for transport proteins. In general, the in vivo methods involve introducing a population of packages into a body compartment in a test animal and then recovering and identifying the subset of introduced complexes transported through cells lining the body compartment into which the complexes were placed. More specifically, the screens typically involve monitoring a tissue or body fluid (e.g., the mesenteric blood and lymph circulation) for the presence of complexes that have entered the blood or lymph of the test animal. The packages can be deposited in any body compartment that contains transport proteins capable of transporting a package into a second body compartment, especially the intestinal lumen and the central nervous system compartment. The test animal can be of essentially any type including primates, domestic animals (e.g., dogs and cats), farm animals (e.g., sheep, pigs and cows). Certain methods can be performed with human subjects, whereas other methods are conducted with non-human animals.

Certain methods using phage are performed by withdrawing a sample from the receiving compartment and titering the sample to detect plaque formation which indicates transport of a package through the cell layer separating the two compartments. Other methods are performed with packages that include a reporter. The reporter can be a capture tag that facilitates the retrieval and concentration of packages that are transported. Suitable capture tags, include for example, biotin, magnetic particles associated with the library complex, haptens of high affinity antibodies, and high density metallic particles such as gold or tungsten. The complexes can also include a detection tag to further enhance the retrieval and detection process. As the name implies, detection tags are molecules that are readily identifiable and can be used to monitor the retrieval and concentration of transported complexes. Examples of such compounds include fluorescent molecules, amplifiable DNA molecules, enzymatic markers, and bioactive molecules.

Because of the replication and amplification potential of the replicable genetic packages of the present invention, the in vivo assay methods of the invention provide a very sensitive means of tracking compound-bearing packages as transit from the body cavity to the blood. Even if only a very small number of packages are recovered, the packages can be amplified to facilitate identification.

d. Tissue Localization Methods

Other methods provides information on tissue localization of the transported phage. For example, phage libraries introduced into the blood can be analyzed for members taken into the brain through the blood brain barrier. The destination tissue (brain) is excised and sectioned (though not fixed) as for histological examination. Phage that successfully transported into the tissue can be analyzed by homogenization of the tissue, followed by titering on host cells and sequence tag identification as described above. Alternatively, detection can be performed in situ. In such methods, a histological slice of thickness from 0.1 to several millimeters (depending on the resolution required for a particular analysis) is placed on a filter spread with a lawn of growing host bacteria and placed on a nutrient agar plate. This is placed at 37° C. for a time sufficient to allow diffusion of phage in the tissue to infect the bacteria and to form plaques of ~0.1 to several mm. In another option, slices are placed on a membrane filter for a period of sufficient duration that allows phage particles that have diffused from the slices to be captured on the filter. The filter is then placed on lawn of host bacteria overnight to allow plaque formation.

The time of incubation depends on the type of phage employed and the size of plaques desired, and can range from a few minutes to many hours for prokaryotic viruses. The tissue slice is then removed and analysis of the plaques is undertaken. As apparent to one skilled in the art, there are a variety of possible formats by which the phage can be amplified and immobilized for analysis. The protocol described here represents just one of the acceptable protocols. The phage plaques can be counted, individual plaques eluted and sequenced, and the array of plaques probed with a panel of labeled oligonucleotides for in situ tag identification, much as described above. This process provides information on the identification of successfully transported phage clones (and their attached compounds), quantitation of the number of transported particles from each clone (a measure of the success and capacity of a given clone (compound), and the micro-localization of the phage in the tissue.

The most successful clones are selected and decoded to identify the compound borne by their coat. This compound represents an activating ligand for a receptor mediating the transport of the phage. With this ligand as a probe, the responsible receptor can then be identified and cloned by standard expression cloning techniques. The general method thus identifies a receptor mediating a endocytosis/transcytosis pathway with desirable characteristics (high capacity in this example), and a ligand that activates the receptor, along with some detail on the kinetics of transport and the microlocalization within the destination tissue.

C. Assays for Antimicrobial Activity

The replicable genetic packages of the invention can also be used in screens to identify compounds having antimicrobial activity, i.e., the ability to retard or kill microorganisms (e.g., bacteria, viruses, fungi and parasites). One suitable approach is described in WO 95/12608 (incorporated by reference in its entirety). In brief, cells are plated on agar plates and then overlayed with a layer of agar into which the replicable genetic packages of the invention are suspended at a suitable dilution so that individual packages can be picked using a capillary for example. The compound borne by the package is released, such as by cleavage of a linker attached to the compound. The agar plate is cultured to allow diffusion of the compound through the upper layer of agar down to the layer containing cells. The extent to which the released compound affects the growth or morphology of the cells is monitored. Zones showing the desired response (e.g., death) are selected and regions within the zone from which the compound diffused are picked. The package in the picked zone is expanded and the tag decoded to identify the compound originally attached to the package, thus identifying a compound with the desired antibacterial activity.

D. Signal Transduction Assays

Cells can be genetically engineered so that upon binding of a compound to a receptor signal transduction triggers the formation of a detectable signal. For example, an exogenous gene encoding an enzyme can be inserted into a site where the exogenous gene is under the transcriptional control of a promoter responsive to a signal transducing receptor. Thus, binding to the receptor triggers the formation of the protein which can react with a substrate within the cell to generate a detectable signal. Using such cells, the compounds of the invention can be screened for their ability to bind a receptor and transduce a signal within the cell. In certain instances, the compound can be released from the package by cleavage of a linker attached to the compound. By conducting the assay within a well, it is still possible to keep track of the compounds that are active, even when released from the package. Related assays can be conducted to identify compounds capable of agonizing or antagonizing a signal transducing receptor.

E. Assays for Enzyme Substrates

1. General

A library of compounds displayed on replicable genetic packages can also serve as a source of potential substrates for enzymes of interest. The particular substrate being screened can vary. Certain methods involve screening a library of compound-bearing packages for activity with essentially any type of enzyme, including, but not limited to, proteases, kinases, phosphatases, conjugating enzymes (e.g., glucuronidation, sulfation), metabolizing enzymes and hydrolases (e.g., those cleaving ester linkages). In other methods, the compounds borne by the replicable genetic packages are potential prodrug linker moieties and the screen involves identifying linkers that are cleaved under particular physiological conditions. Still other screens are conducted with a library of compounds attached to packages that are variants of a drug molecule. The goal being to identify a compound that is less susceptible to modification or inactivation by an enzyme.

2. Assay Procedures

The methods initially generally involve contacting the library of compound-bearing packages with either a purified or crude enzyme preparation under conditions compatible with the activity of the target enzyme. After sufficient exposure of the library to the active enzyme, two primary options are available to identify packages that bear substrates for the enzyme. One approach is a negative selection approach and involves detecting the absence of the initial compounds displayed on the package. Alternatively, a positive selection approach can be utilized. This approach involves selecting for the presence of a product displayed on the package resulting from the conversion of displayed compounds.

The selection step is often performed by binding the library to a "receptor" chosen to bind the substrates of the products of the enzyme reaction. The particular "recepto" utilized can take a variety of forms. Suitable receptors include, but are not limited to: 1) an antibody or biological receptor recognizing some, most, or all of the starting displayed compounds; 2) an antibody or cellular receptor recognizing potential products of the reaction; 3) an antibody or cellular receptor recognizing a moiety added to the library compounds via the activity of the enzyme; 4) an antibody or biological receptor recognizing a degradation product of the reaction; and 5) an antibody or biological receptor recognizing a portion of the initial compounds that becomes exposed as a consequence of the activity of the enzyme.

Enzymatic degradation can be assayed for and detected by utilizing the displayed compounds to link a common affinity "handle" to the phage. For example, protease substrates can be selected by creating a library of compounds attached to a replicable genetic package such as a phage. A common antibody epitope or hapten (the affinity handle) is installed or attached to the displayed compounds distal to the phage attachment point. The library is subsequently exposed to the protease of interest. The resultant library is screened against an antibody specific for the affinity handle, with free phage being enriched for protease substrates.

A similar method can be utilized to select and optimize prodrug linker moieties. Initially, a library of potential prodrug linkers is created and attached to replicable genetic packages such as phage clones. A common affinity handle is installed on the displayed compounds distal to their attachment point on the phage and the library exposed to specific enzyme preparations or to extracts of the tissue likely (or desired) to effect cleavage. Following exposure, the library is selected against an antibody recognizing the affinity handle. The remaining free phage carry compounds enriched in linker moieties cleaved by the enzyme/tissue fraction of interest.

Another option for selecting prodrug moieties is as follows. A library of potential prodrug linkers connected to the drug compound of interest is created and attached to replicable genetic packages, with attachment to the package through the drug portion of the complex. The library is then exposed to the enzyme or tissue fraction of interest. The library is screened for binding to a receptor or antibody specifically recognizing the drug cleaved free of the linker moiety. The captured phage carry compounds enriched in linkers cleaved by the enzyme/tissue of interest.

The foregoing screening methods for prodrug moieties can be adjusted to identify prodrug linkers that are optimized to be more easily or less easily cleaved by an enzyme/tissue fraction of interest. For example, the stringency of selection can be controlled by altering the conditions of the enzyme reaction. In particular, the time and temperature of the reaction can be increased or decreased to favor the selection of either more labile or more stable linker structures, either in the context of the drug of interest or in a general format.

Certain methods can be designed to select a variant of a drug molecule that is less susceptible to modification or inactivation by an enzyme or a target tissue or systemic exposure in an animal. Such methods involve creating a library of the variants of the drug and attaching them to a replicable genetic package (e.g., a phage). The library is exposed to the enzyme, the target tissue, or the body compartment of the animal. The library is recovered and then screened against a target receptor of the drug (the receptor recognizing only the pharmacologically active molecules). The captured phage are enriched in compounds stable to the metabolic activity of the chosen enzyme, tissue, or tissue compartment. Optimization of the selected variants can be accomplished by controlling the stringency of the metabolic step as just described.

VIII. Options Subsequent to Screening

A. Modification of Lead Compound

Once a compound or multiple compounds have been identified after an initial round of screening as having a desired characteristic or activity (a lead compound or lead compounds), the compound(s) can serve as the basis for additional rounds of screening tests. For example, if several different compounds are identified in an initial round, the compounds can be analyzed for common structural features or functionality. Based upon such common features, another library incorporating one or more of the common features or functionalities can be synthesized and subjected to another round of screening to identify compounds that are potentially more active than the compounds identified initially. Alternatively, a new set of compounds derived from each of the positive compounds identified in the initial screening can be synthesized and utilized in another round of screening. Of course, this process can be repeated in an iterative manner until the desired degree of refinement in the compound is obtained.

B. Attachment of Different Moieties at Linkage Site

One feature of the present invention is that the screening methods typically utilize compounds that are tethered to a relatively large moiety, namely a replicable genetic package such as a phage. Hence, active compounds identified through the screening methods of the invention are likely able to retain activity even if a different moiety is attached at the linkage site (i.e., the site on the compound to which the replicable genetic package or a linker is attached). Further studies can be undertaken to identify what other types of moieties can be attached at the linkage site. Since the screening methods often are designed to screen for potential therapeutic agents, various moieties that complement the potential therapeutic value of the compound can be attached and screened to determine if activity is retained.

For example, various other small molecules can be attached at the linkage site. Such small molecules can have activities similar to that of the identified compound or an unrelated but complementary activity. Examples of the latter type of compound include buffers, antioxidants, molecules with affinity for serum albumin (useful for extending half-life of the compound in vivo), molecules that are substrates for transport proteins, and molecules with affinity for proteins expressed in specific organs.

Instead of attaching another small molecule, various supports can be attached to the linkage site. Examples of such supports include nanoparticles (see, e.g., U.S. Pat. Nos. 5,578,325 and 5,543,158), molecular scaffolds, liposomes (see, e.g., Deshmuck, D. S., et al., Life Sci. 28:239-242 (1990), and Aramaki, Y., et al., Pharm. Res. 10:1228-1231 (1993), protein cochleates (stable protein-phospholipid-calcium precipitates; see, e.g., Chen et al., J. Contr. Rel. 42:263-272 (1996), and clathrate complexes. These supports can be used to attach other active molecules. Certain supports such as nanoparticles can also be used to encapsulate desired compounds.

C. Formulation of Active Compounds into Pharmaceutical Compositions

Compounds identified through the screening and rescreening processes described above to have a desired biological activity can be incorporated into pharmaceutical compositions. Typically, such compounds are combined with pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., Remington's Pharmaceutical Sciences, Mace Publishing Company, Philadelphia, Pa., 17th ed. (1985); for a brief review of methods for drug delivery, see, Langer, Science 249:1527-1533 (1990); each of these references is incorporated by reference in its entirety).

The compositions can be administered for prophylactic and/or therapeutic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, compositions are administered to a patient susceptible to or otherwise at risk of a particular disease or infection. Hence, a "prophylactically effective" is an amount sufficient to prevent, hinder or retard a disease state or its symptoms. In either instance, the precise amount of compound contained in the composition depends on the patient's state of health and weight.

An appropriate dosage of the pharmaceutical composition is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The pharmaceutical compositions can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. The route of administration depends in part on the chemical composition of the active compound and any carriers.

Particularly when the compositions are to be used in vivo, the components used to formulate the pharmaceutical compositions of the present invention are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The following examples are provided to illustrate certain aspects of the invention and are not to be construed to limit the invention.

EXAMPLE 1

Attachment of Compounds to fd Phagemid Particles through Non-Covalent Linkage (biotin/streptavidin)

I. Preparation of the Phagemid

A. General

Figure 9:
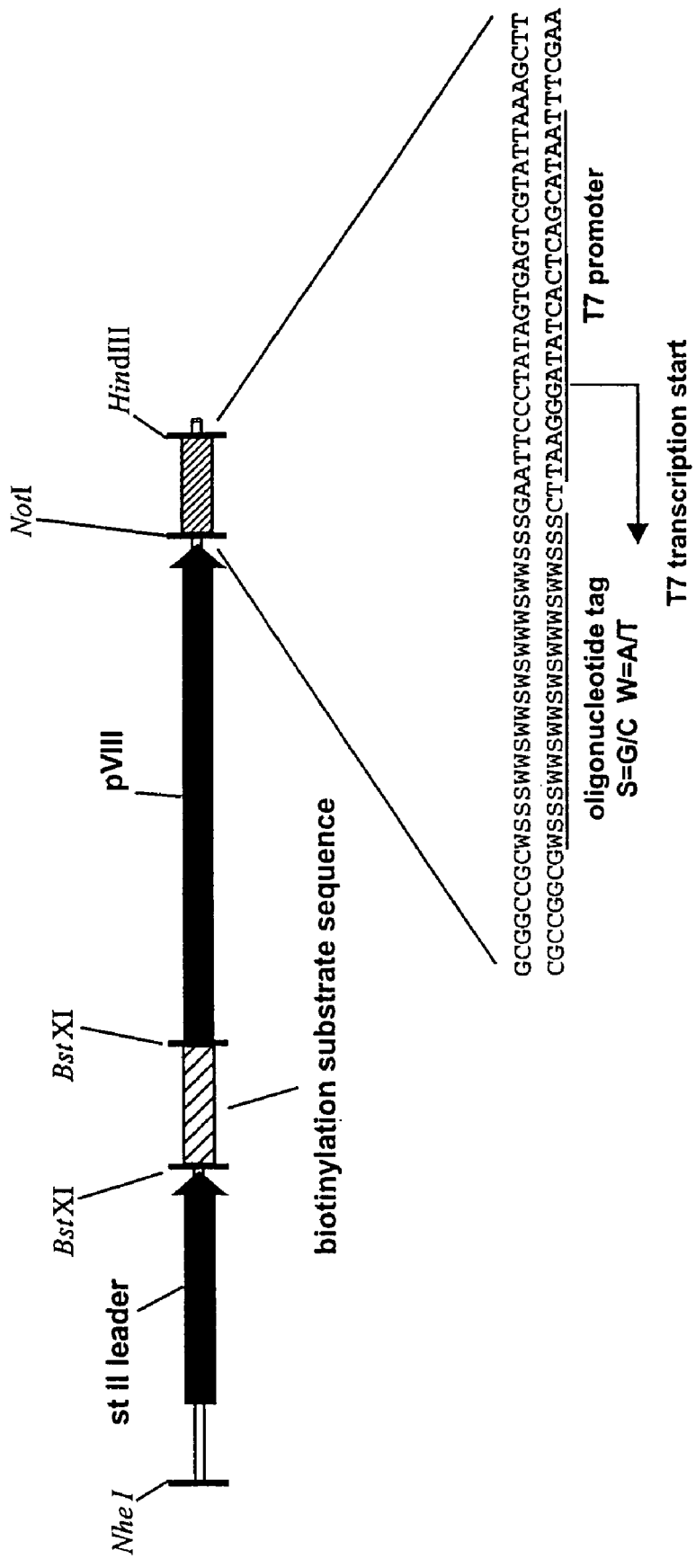
FIG. 9 shows an example of the location and orientation of various genetic elements (SEQ ID NO:1) inserted into a phagemid (gene VIII) thus enabling a hybridization probe to be prepared from the replicable genetic package.

Filamentous phagemid vector is constructed to place a peptide biotinylation substrate sequence (see Schatz (1993) Bio/Technology 11: 1138-1143) in the N-terminus of the major coat protein pVIII. A library is then constructed in this modified vector as follows. A collection of randomly synthesized oligonucleotides is inserted into a non-expressed portion of the phagemid to create a population of phage clones, each uniquely encoded by a specific oligonucleotide sequence (FIG. 9). The library is transformed into bacteria by electroporation, plated on LB ampicillin plates, and individual colonies are picked and added to wells of microtiter plates. Helper phage are added to each well and the phagemid clones are expanded by overnight growth. The bacteria are then removed from each well by centrifugation or filtering.

B. Biotinylation

1. General

Biotinylation of the substrate sequence by the native E. coli biotin holoenzyme synthetase (BirA) occurs in vivo during overnight growth of the phagemid. Increased levels of biotinylation can be achieved by using a host bacterial strain that overexpresses BirA to amplify the phagemid. Alternatively biotinylation of the displayed substrate sequence can take place in vitro by adding biotinylation buffer, biotin, and the enzyme BirA to the phage containing supernatant. The plates are incubated at 30° C. for 30 minutes to biotinylate the phagemid particles, and the phage are precipitated or affinity purified in the wells and washed to remove the excess biotin. Streptavidin is added to all wells at sufficient excess to saturate the biotinylated phagemid. Once again the phagemid particles are precipitated or affinity purified and washed to remove the excess streptavidin.

2. Protocol for Enzymatic Biotinylation of Phagemid

Figure 13:
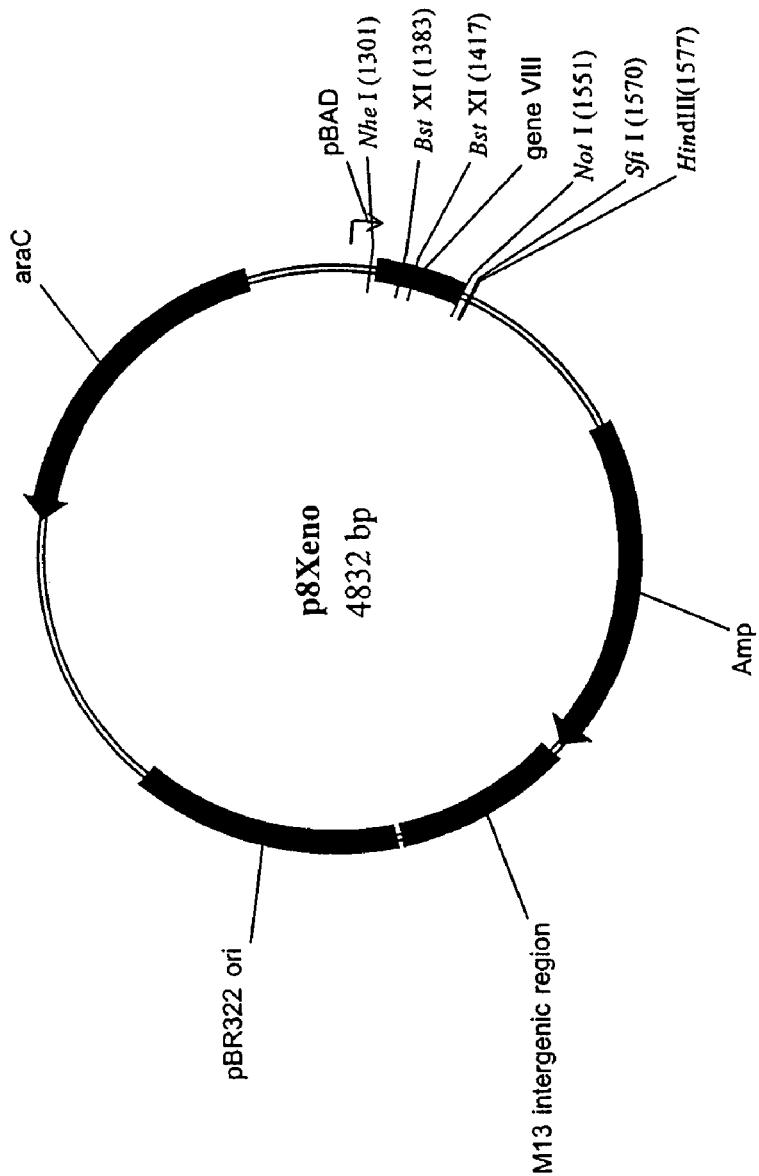
FIG. 13 is a map of the pVIII phagemid vector p8Xeno. The vector was constructed by inserting gene VIII of M13 into the multiple cloning site of the phagemid vector pBAD18. The pBAD promoter of the arabinose operon and its regulatory gene, araC, tightly regulate the expression of pVIII.

Phage coat proteins can be specifically labeled in vivo with biotin by cloning a substrate sequence for E. coli biotin holoenzyme synthetase (BirA) into the appropriate display vector. A 16-amino acid substrate sequence was cloned into the 5' end of the gene for the filamentous phage coat protein pVIII in the phagemid vector p8Xeno (FIGS. 10A and 13). The expression of gene VIII is under the control of the inducible arabinose promoter. In the presence of arabinose, transcription from the promoter is induced; in the presence of glucose it is strongly repressed. The substrate sequence phagemid DNA was introduced into E. coli DH5α F' by electroporation, followed by infection of the cells with M13KO7 helper phage. Phagemid vectors require helper phage to provide all the necessary gene products for the production of phage particles. Cells were cultured in bacterial medium containing the appropriate antibiotics for selection of cells containing both phagemid and helper phage, and 0.2% arabinose and glucose to induce the expression of the recombinant pVIII protein. These culture conditions are designed to produce phage that display several hundred copies of substrate sequence fused to pVIII on each phage particle.

Figure 11:
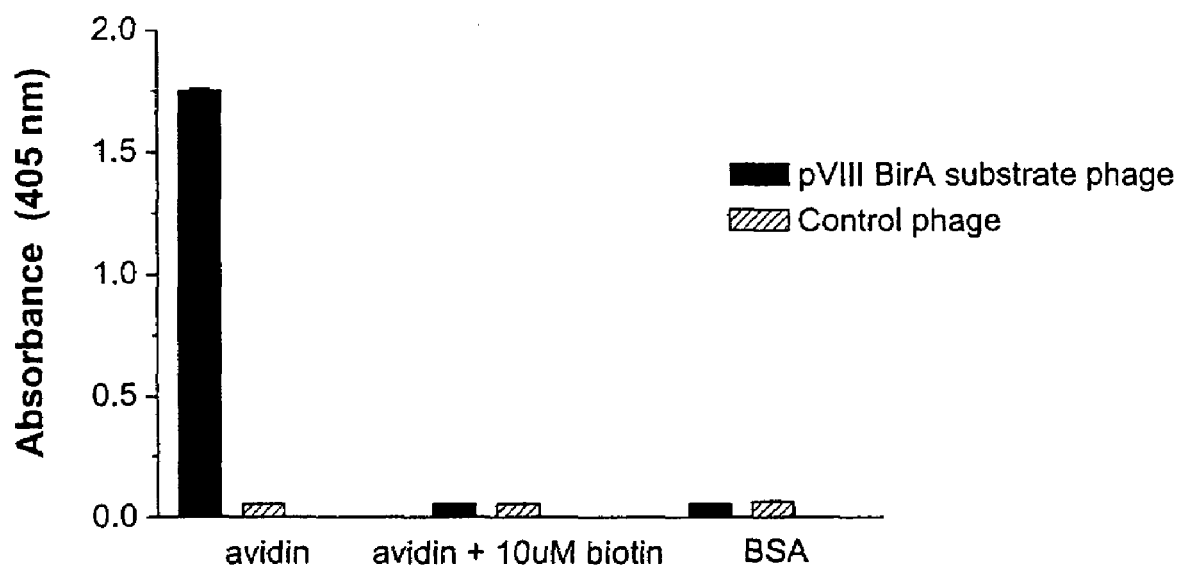
FIG. 11 illustrates the result of a phage ELISA with filamentous phage displaying the BirA substrate sequence and biotinylated in vivo. The assay is described in detail in Example 1.

The extent of in vivo biotinylation of filamentous phage particles displaying the substrate sequence was measured using a phage ELISA. The wells of a microtiter plate were coated with 2.5 µg of avidin and blocked with PBS/1% BSA. Phage were added to each well in the presence or absence of 10 µM free biotin and incubated at 4° C. for 1 hour. Bound phage were detected with a horseradish peroxidase-conjugated anti-M13 antibody followed by the addition of ABTS development buffer. The amount of horseradish peroxidase activity in each well was then measured by reading the absorbance at 405 nm with a microtiter plate reader. Phage displaying the BirA substrate sequence were specifically captured on avidin coated microtiter wells, indicating that the coat protein was biotinylated in vivo (FIG. 11).

II. Attaching the Compounds to the Phagemids

A collection of D-peptides is synthesized to contain a common C-terminal biotinylated lysine. An aliquot of each of the compounds is added to a corresponding well of the 96 wells containing the streptavidin-prepared phagemid particles. After a period of incubation to allow the biotinylated compounds to bind to the phagemid particles, 10 µM biotin is added to block available binding sites on the phage, and an aliquot is taken from each well and pooled. The microtiter plate is set aside as a spatially-addressed archive of compound-decorated phagemid clones. The pooled phagemids are precipitated and washed to remove the free compound and biotin.

EXAMPLE 2

Screen of Library of Compounds Displayed on Filamentous Phage Particles for Compounds Absorbed by Transcytosis through Polarized Epithelial Cells I. Cell Culture Low passage number MDCK (Madin Darby Canine Kidney) cells are grown in DMEM supplemented with 10% FBS and antibiotics (Kanamycin 100 ug/ml; Penicillin 0.5 units/ml; Streptomycin 0.5 ug/ml) to approximately 80% confluence on TC plastic. The cells are removed from the dishes with trypsin/EDTA and seeded at confluent density (approximately $5 \times 10^5$ cells/cm$^2$) onto 12 mm or 24 mm transwells (0.4 µm pore size). The cells are returned to the incubator for 5 days, with daily medium change, to establish differentiated (fully polarized) monolayers.

II. Screening for Transcytosis of Library Members

Normal growth medium containing antibiotics is removed from the 5 day differentiated cultures and replaced with DMEM supplemented with 10% FBS (no antibiotics). The cells are returned to the incubator for 1 to 2 h to allow equilibration of the medium. A filamentous phage library is precipitated with 1/10 volume of acetic acid, and resuspended in 1 ml of DMEM supplemented with 10% FBS (0.5 ml for 12 mm transwell) at a concentration of ~$10^{12}$ TU/ml.

Approximately 1 ml of medium (0.5 ml for 12 mm transwell) is removed from the apical chamber and replaced with 1 ml (0.5 ml for 12 mm transwell) of phage resuspended in cell culture medium. (Alternatively, amplified phage stocks are added directly (without PEG precipitation) to the apical chamber in a volume not exceeding 10% of the total apical volume; the appropriate volume of cell culture medium is removed from the apical chamber just prior to the addition of the amplified phage stock to maintain the correct apical volume).

2 µCi of $^3$H-inulin (1 µCi for 12 mm transwells) is also added to each transwell along with the phage to monitor monolayer integrity.

The cultures are returned to the 37° C. incubator for 2 h. At the end of 2 h, the medium from the apical chamber (1.5 ml for 24 mm transwell; 0.5 ml for 12 mm transwell) and basal chamber (2.5 ml for 24 mm transwell; 1.5 ml for 12 mm transwell) is collected. 1% of the medium from each chamber is counted in a scintillation counter to measure $^3$H-inulin passage.

The remaining sample is then titered as follows:

Apical medium is diluted down to approximately $10^4$ TU/ml. 10 µl of this dilution is then combined with 100 µl of K91 recA bacteria (O.D. 0.6-0.8). The phage and bacteria are placed at 37° C. for 20-30 min and then plated onto LB Amp (100 ug/ml ampicillin) plates. The plates are then placed at 37° C. overnight. 10% of the basal medium (250 µl for 24 mm transwell; 150 µl for 12 mm transwell) is combined with 10 µl of concentrated K91 recA bacteria (O.D. 0.6-0.8) (K91 recA bacteria are concentrated 10 fold following centrifugation at 3000 rpm for 5 min). The phage and bacteria are placed at 37° C. for 20-30 min and then plated onto LB Amp (100 ug/ml ampicillin) plates. The plates are then placed at 37° C. overnight.

EXAMPLE 3

Screen of Library of Compounds Displayed on Phage Particles for Compounds Absorbed by Transcytosis through the Intestinal Epithelium A library of compounds displayed on filamentous phage is prepared as described in Example 1 and screened as follows:

The washed pool is resuspended in 0.2 ml of buffered saline and placed directly into the proximal portion of the small intestine of a rat. At times 10, 30, 60, 120, 240, 480 minutes following insertion of the library, blood samples are taken from the tail vein of the animal. Samples are anticoagulated and the red blood cells removed by centrifugation.

Each sample of cleared plasma is then combined with host bacteria, plated on the appropriate growth medium, and incubated overnight to form colonies. The heterologous nucleic acid tag in each colony is determined as previously described in the tagged screening method described supra.

EXAMPLE 4

Attachment of Compounds to T7 Phage Particles through Non-Covalent Linkage (Biotin/Streptavidin)

I. Preparation of T7 Phage

Figure 12:
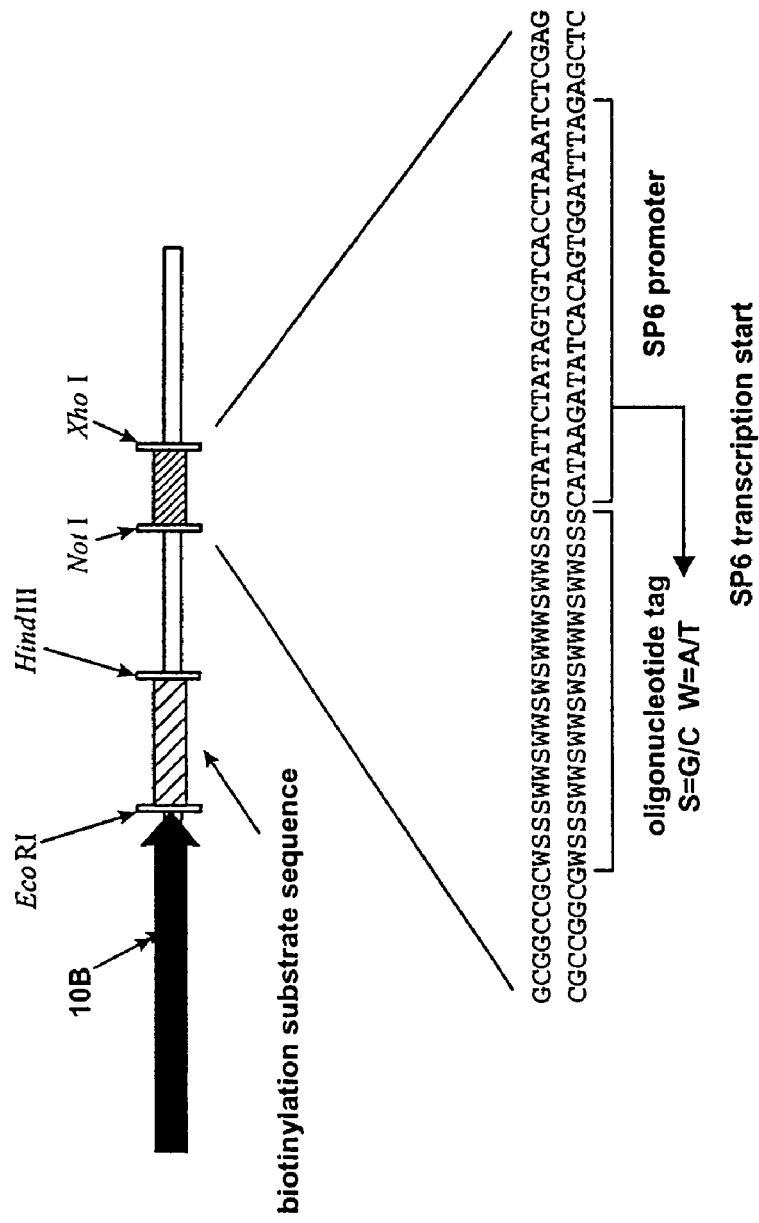
FIG. 12 shows an example of the location and orientation of various genetic elements (SEQ ID NO:6) inserted into a T7 phage vector thus enabling a hybridization probe to be prepared from the replicable genetic package.

The 16-amino acid BirA substrate sequence was cloned into the 3' end of gene 10B, the major coat protein of T7 phage (FIG. 10B). Phage DNA was packaged in vitro followed by infection into E. coli BL21 cells. Phage produced by this vector display substrate sequence fused to all 415 copies of major coat protein present in the mature T7 particle. A collection of randomly synthesized oligonucleotides is inserted into a non-expressed portion of the phage genome to create a population of phage clones, each uniquely encoded by a specific oligonucleotide sequence (FIG. 12). The library is then plated on a bacterial lawn of BL21 cells, and individual plaques picked and added to wells of microtiter plates. Host bacteria are added to each well and the phage clones expanded by growth for 3 to 6 h at 37° C. The bacterial debris is then removed from each well by centrifugation or filtering. Streptavidin is added to all wells at sufficient excess to saturate the biotinylated phage. Once again the phage particles are precipitated or affinity purified and washed to remove the excess streptavidin.

Biotinylation of the substrate sequence is accomplished using the in vivo or in vitro methods described in Example 1.

II. Attaching the Compounds to the Phage

A collection of D-peptides is synthesized to contain a common C-terminal biotinylated lysine. These compounds are subsequently attached to the phage as described supra in Example 1.

EXAMPLE 5

Screening a Library of Compounds Displayed on T7 Phage Particles for Compounds Absorbed by Transcytosis through Polarized Epithelial Cells I. Cell Culture:

Low passage number MDCK cells are grown in DMEM supplemented with 10% FBS and antibiotics (Kanamycin 100 ug/ml; Penicillin 0.5 units/ml; Streptomycin 0.5 ug/ml) to approximately 80% confluence on TC plastic. The cells are removed from the dishes with trypsin/EDTA and seeded at confluent density (approximately $5 \times 10^5$ cells/cm$^2$) onto 12 mm or 24 mm transwells (0.4 μm pore size). The cells are returned to the incubator for 5 days, with daily medium change, to establish differentiated monolayers.

II. Screening for Transcytosis of Library Members

Normal growth medium containing antibiotics is removed from the 5 day differentiated cultures and replaced with DMEM supplemented with 10% FBS (no antibiotics). The cells are returned to the incubator for 1 to 2 h to allow equilibration of the medium. A T7 phage library is PEG precipitated and resuspended in 1 ml of DMEM supplemented with 10% FBS (0.5 ml for 12 mm transwell) at a concentration of ~$10^{12}$ TU/ml One ml of medium (0.5 ml for 12 mm transwell) is removed from the apical chamber and replaced with 1 ml (0.5 ml for 12 mm transwell) of phage resuspended in cell culture medium. (Alternatively amplified phage stocks are added directly (without PEG precipitation) to the apical chamber in a volume not exceeding 10% of the total apical volume; the appropriate volume of cell culture medium is removed from the apical chamber just prior to the addition of the amplified phage stock to maintain the correct apical volume). 2 μCi of $^3$H-inulin (1 μCi for 12 mm transwells) is also added to each transwell along with the phage to monitor monolayer integrity.

Cultures are returned to the 37° C. incubator for 2 h. At the end of 2 h, the medium from the apical chamber (1.5 ml for 24 mm transwell; 0.5 ml for 12 mm transwell) and basal chamber (2.5 ml for 24 mm transwell; 1.5 ml for 12 mm transwell) is collected. 1% of the medium from each chamber is counted in a scintillation counter to measure $^3$H-inulin passage.

The remaining sample is then titered:

Apical medium is diluted down to approximately $10^3$ TU/ml. 100 μl of this dilution is then combined with 200 μl of BL21 cells (O.D. 0.6-0.8) and 3 ml top agar and plated onto LB plates. The plates are then placed at 37° C. for 3 h or at room temperature overnight. 10% of the basal medium (250 μl for 24 mm transwell; 150 μl for 12 mm transwell) is combined with 200 μl of BL21 cells (O.D. 0.6-0.8) and 3 ml top agar and plated onto LB plates. The plates are then placed at 37° C. for 3 h or at room temperature overnight.

EXAMPLE 6

Screening a Library of Compounds Displayed on Phage Particles to Identify Compounds Absorbed by Transcytosis through the Intestinal Epithelium A library of compound displayed on T7 phage is prepared as described in Example 4 and screened as follows:

The washed pool is resuspended in 0.2 ml of buffered saline and placed directly into the proximal portion of the small intestine of a rat. At times 10, 30, 60, 120, 240, 480 minutes following insertion of the library, blood samples are taken from the tail vein of the animal. Samples are anticoagulated and the red blood cells removed by centrifugation. Each sample of cleared plasma is then plated on a lawn of host bacteria and incubated overnight to form plaques. The nucleic acid tag in each plaque is determined as previously described in the tagged screening section supra.

EXAMPLE 7

Screening Library of Compounds Displayed on Phage Particles to Identify Compounds Absorbed by Transcytosis through the Endothelial Blood Brain Barrier Libraries of compounds displayed on phage particles are prepared as described in Examples 1 and 4 and screened as follows:

The washed pool is resuspended in 500 μl of buffered saline and 50 μl injected into each of 10 rats by IV injection. At times 10, 30, 60, 120, 240, 480 minutes following insertion of the library, rats are killed, and their brains perfused with saline. Their brains are excised and divided along the medial axis. One half of each brain is homogenized and the supernatant from a low speed spin is plated on a lawn of host bacteria for plaque growth. The remaining half of each brain is sliced into ~1 mm slices and placed on a membrane filter for captured of diffusing phage particles. The array of slices is photographed for later alignment of plaques with brain slices, and the filter is marked for orientation. After overnight period at 4° C., The slices are removed and the filter is placed on a lawn of host bacteria and incubated at 37° C. overnight to allow plaque formation. The nucleic acid tag in each plaque is determined as previously described in the tagged screening section supra.

EXAMPLE 8

Quantitative Assay of Single Compounds for Transcytosis through Epithelial Cell Layer I. Cell Culture:

Low passage number MDCK cells are grown in DMEM supplement with 10% FBS and antibiotics (Kanamycin 100 ug/ml; Penicillin 0.5 units/ml; Streptomycin 0.5 ug/ml) to approximately 80% confluence on TC plastic. The cells are removed from the dishes with trypsin/EDTA and seeded at confluent density (approximately $2\times10^5$ cells/well) onto 0.4 μm millicell inserts arranged in 96 well format (6 mm diameter inserts). Each chamber contains 250 μl medium. The cells are returned to the incubator for 5 days to establish differentiated monolayers (medium is changed daily).

Addition of Phage:

Normal growth medium containing antibiotics is removed from the 5 day differentiated cultures and replaced with DMEM supplemented with 10% FBS (no antibiotics). The cells are returned to the incubator for 1 to 2 h to allow equilibration of the medium.

During this time each phage clone is precipitated (using 1/10 vol of acetic acid for fd or PEG for T7) and resuspended in 250 μl of DMEM supplemented with 10% FBS at a concentration of $\sim10^{12}$ TU/ml. The medium is removed from the apical chamber and replaced with 250 μl of phage resuspended in cell culture medium. (Alternatively each phage clone is added directly (without precipitation) to the apical chamber in a volume not exceeding 10% of the total apical volume; the appropriate volume of cell culture medium is removed from the apical chamber just prior to the addition of the amplified phage stock to maintain the correct apical volume). $^3$H-inulin (0.5 uCi) is also added to each transwell along with the phage to monitor monolayer integrity.

The cells along with phage and $^3$H-inulin are returned to the 37° C. incubator for 2 to 6 h. At the end of the incubation, the medium from the apical chamber (250 ul/well) and basal chamber (250 ul/well) is collected. 1% of the medium from each chamber is then placed in a white 96 well plate with a clear bottom. 150 μl of scintillation fluid is added to each well, the plate is mixed, centrifuged, and placed in a scintillation counter to measure $^3$H-inulin passage.

The remaining sample is then titered:

Apical medium is diluted down to approximately $10^4$ TU/ml. 10 μl of this dilution is then combined with 100 μl of K91 recA bacteria (O.D. 0.6-0.8). The phage and bacteria are placed at 37° C. for 20-30 min and then plated onto LB Amp (100 ug/ml ampicillin) plates. The plates are then placed at 37° C. overnight. 50% of the basal medium (125 ul/well) is combined with 10 μl of the appropriate host bacteria and titered as described in the preceding examples.

EXAMPLE 9

Quantitative Assay of Single Compounds for Transcytosis through Intestinal Wall of Test Animal A single clone of phage is decorated with the test compound prepared as described in example 1 and 4. The phage particles are placed in the delivery compartment of the animal (e.g., small intestine) and samples are taken from the destination compartment (e.g., blood) at times of 10 min to 12 h. Samples are plated on lawns of host bacteria, grown overnight and titer determined. The titer provides an estimate of the relative transport of that compound.

EXAMPLE 10

Identification of Library Members Positive for Transcytosis

I. Preparation of Labeled Probes for Hybridization with Archival Grids

The following example is for a phage having the genetic structure shown in FIG. 9. This particular phage is a filamentous phagemid pVIII vector with BstXI cloning sites in the N-terminal domain of the major coat protein pVIII, with a T7 RNA polymerase recognition sequence placed on the 3' side of the second BstXI site (T7 promoter pointed upstream, in opposite direction of pVIII transcription) and a NotI site immediately upstream of a 21-base pair tag. The sequence of the oligonucleotide tag is designed such that each tag will contain an equivalent number of G/C and A/T base pairs, and therefore will produce isothermal probes for hybridization from the in vitro transcription reaction described below. In this example, $(2)^{21}$ or 2.1 million different sequence tags are encoded.

II. DNA Template Preparation

Phage particles, recovered by elution from the immobilized protein matrix, are amplified by infection of host E. coli cells, grown under selective conditions, and harvested according to standard procedures, and double-stranded RF-DNA is prepared as described (W. J. Dower and S. E. Cwirla. "Epitope mapping using libraries of random peptides." in Peptide Antigens: A Practical Approach (G. B. Wisdom, Ed.) Oxford University Press, 1994, pp. 219-243).

The phage DNA is digested with NotI to linearize the DNA, followed by agarose gel isolation of the digested DNA from the undigested DNA. The linearized, purified plasmid is extracted with phenol:chloroform:isoamyl alcohol prior to adding to in vitro transcription reactions.

III. Preparation of $^{33}$P-Labeled RNA Probe

Radiolabeled RNA is prepared using a Promega Corp Riboprobe T7 system according to manufacturers protocols. The protocols described below are a modification of the procedure described by Melton (Melton, D. A. et al., Nucl. Acids Res. 12: 7035 (1984). For RNA synthesis in vitro, RNA transcripts may be radiolabeled with $^{32}$P-, $^{33}$P-, $^{35}$S- or $^3$H-labeled ribonucleotides. Precautions should be taken to protect against ribonuclease contamination.

A standard in vitro transcription reaction (minus the nucleotides and RNA polymerase) is set up at room temperature, as follows:

1. Combine:
   4 μl Transcription Optimized 5× Buffer
   2 μl 100 mM DTT
   20 units Recombinant RNasin® Ribonuclease Inhibitor
   1 μl linearized template DNA (0.2-1.0 mg/ml in water or TE buffer)
2. Transcription reaction is initiated by adding the nucleotide mix and RNA polymerase:
   4 μl of nucleotide mix [rATP, rGTP and rUTP (2.5 mM each) (prepared by mixing 1 volume deionized water with 1 volume of each of the 10 mM rATP, rGTP and rUTP stocks supplied]
   2.4 μl of 100 μM RCTP (diluted from stock)
   5 μl [α-$^{33}$P]rCTP (50 μCi at 10 Ci/μl [~1000 Ci/mmol])
   15-20 units T7 RNA Polymerase
   The mixture is brought to a final volume of 20 μl with water.
3. Incubate for 1 hour at 37-40° C.
4. Remove 1 μl from the reaction to determine the percent incorporation and specific activity of the probe. RNA transcribed in vitro will typically have a specific activity of 2-2.5× $10^8$ cpm/μg.

IV. Removal of the DNA Template following Transcription

The DNA template is removed by digestion with RNAse-free DNase I (Promega) following the transcription reaction. After performing the in vitro transcription reaction:
1. RQ1 RNase-Free DNase is added to a concentration of 1 u/μg of template DNA and incubated for 15 minutes at 37° C.
2. The reaction is extracted with 1 volume of TE-saturated phenol:chloroform:isoamyl alcohol (25:24:1 [pH 4.5]), vortexed for 1 minute and centrifuged in a microcentrifuge (12,000×g) for 2 minutes.
3. The upper, aqueous phase is transferred to a fresh tube and 1 volume of chloroform:isoamyl alcohol (24:1) is added. The mixture is vortexed for 1 minute and centrifuged in a microcentrifuge (12,000×g) for 2 minutes.
4. The upper, aqueous phase is transferred to a fresh tube and 0.5 volume of 7.5 M ammonium acetate and 2.5 volumes of 100% ethanol are added. Tube is mixed and placed at −70° C. for 30 minutes, then centrifuged in a microcentrifuge for 20 minutes.
5. The supernatant is carefully removed and the pellet washed with 1 ml of 70% ethanol, followed by drying of the pellet under vacuum.

V. Removal of Unincorporated Nucleotides

The newly synthesized RNA is separated from unincorporated nucleotides by size exclusion chromatography through a small Sephadex® G-100 or G-50 column in 10 mM Tris-HCl (pH 7.5), and 0.1% SDS (Sambrook, J., Fritsch, E. F. and Maniatis, T. (1989) Molecular Cloning: A Laboratory Manual, Cold Spring Harbor Laboratory, Cold Spring Harbor, N.Y.). Prepacked columns. (from Amersham Pharmacia Biotech) are equilibrated in SDS-containing buffer. Carrier tRNA is added to the sample, the sample passed over the column to remove the unincorporated nucleotides, and ethanol precipitated as described above. The pellet is dried under a vacuum, then suspended in 10-20 μl of TE buffer and stored at −70° C. until use.

VI. Hybridization to Clone Collection Array

To 60 ml of hybridization solution (20.4 ml sterile dH2O, 12.0 ml 50% PEG, 4.5 ml 20×SSPE, 21.0 ml 20% SDS) is added sheared denatured herring sperm DNA to a concentration of 10 ug/ml, and incubated with the array membrane for 1 to 4 hr. Add $10^6$ to $10^7$ cpm of radiolabeled RNA probe to the hybridization mix and incubate at 65° C. overnight with constant, gentle shaking.

Following hybridization, the filters are washed with 200 ml of each of the following:
   Wash 1: 15 minutes in 2×SSPE+0.1% SDS at room temperature
   Wash 2: 15 minutes in 2×SSPE+0.1% SDS at room temperature
   Wash 3: 15 minutes in 0.1×SSPE+0.1% SDS at 65° C.
   Wash 4: 15 minutes in 0.1×SSPE+0.1% SDS at 65° C.

The solution for these washes are prewarmed to 65° C. before use.

The filters are then blotted and prepared for autoradiography. The filters are wrapped in plastic wrap (Glad) and placed on Kodak X-omat AR film, and exposed at −80° C. for 2 to 24 hr.

EXAMPLE 11

Solid State Method of Attachment of Compounds to Phage Clones. Reversible Immobilization of Phage Particles in Wells via Photocleavable Biotin Conjugate I. In Vivo Biotinylation of Phage Particles Filamentous phage coat proteins were specifically labeled in vivo with biotin by cloning a substrate sequence for *E. coli* biotin holoenzyme synthetase (BirA) into the appropriate display vector. A 16-amino acid substrate sequence was cloned into the 5' end of the gene for the filamentous phage coat protein pVIII in the phagemid vector p8Xeno (FIGS. 10A and 13). The expression of gene VIII is under the control of the inducible arabinose promoter. In the presence of arabinose, transcription from the promoter is induced; in the presence of glucose it is strongly repressed. The substrate sequence phagemid DNA was introduced into *E. coli* DH5α F' by electroporation, followed by infection of the cells with M13KO7 helper phage. Phagemid vectors require helper phage to provide all the necessary gene products for the production of phage particles. Cells were cultured in bacterial medium containing the appropriate antibiotics for selection of cells containing both phagemid and helper phage, and 0.2% arabinose and glucose to induce the expression of the recombinant pVIII protein. These culture conditions are designed to produce phage that display several hundred copies of substrate sequence fused to pVIII on each phage particle. Biotinylation of the substrate sequence by BirA occurs in vivo during overnight growth of the phagemid.

Figure 14A:
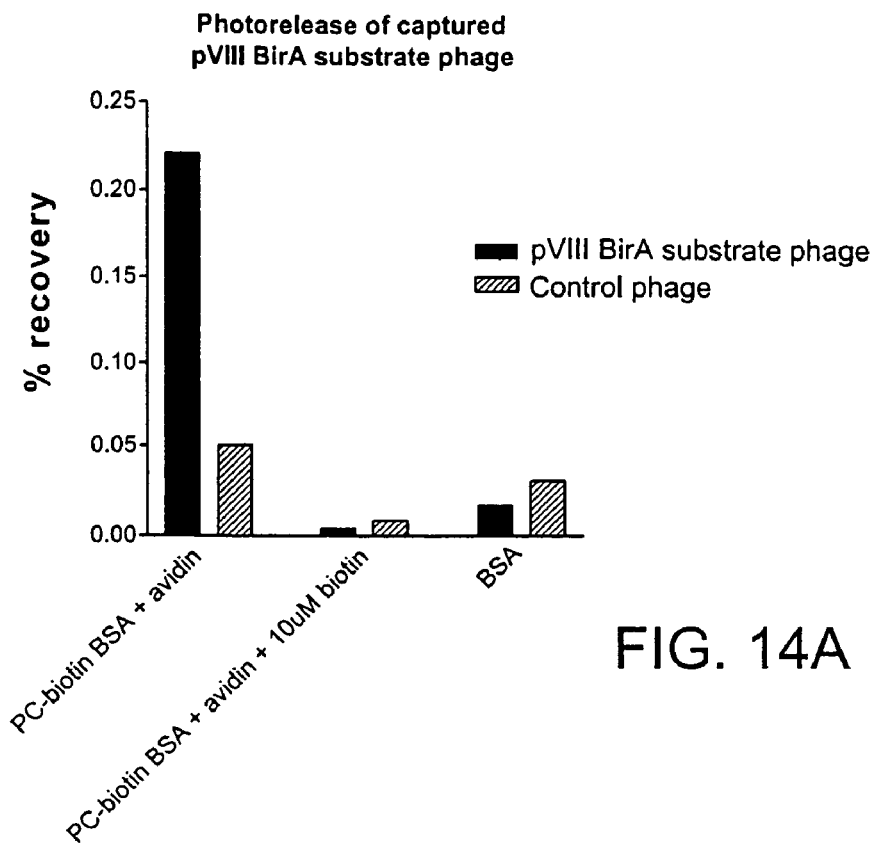
FIGS. 14A and 14B illustrate the result of an assay with biotinylated phage particles captured on immobilized photocleavable-biotin BSA and avidin. The assay is described in detail in Example 11.
Figure 14B:
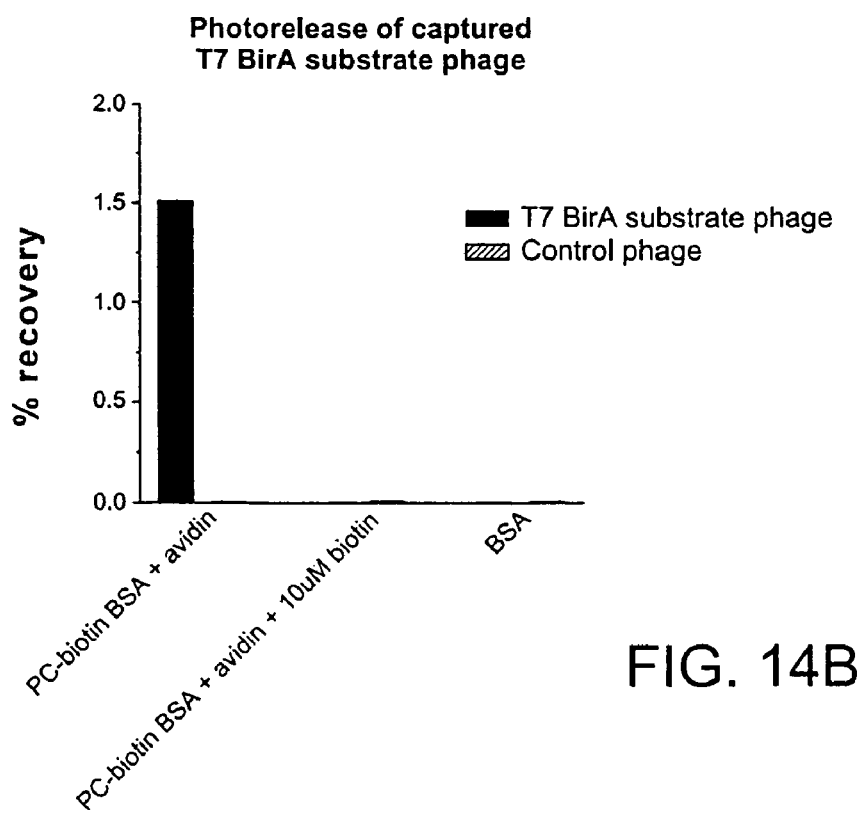

II. Reversible Immobilization of Phase Particles for Covalent Attachment of Small Molecules Individual phage clones containing unique sequence tags and biotinylated as described above, were immobilized in the wells of a microtiter plate to facilitate the attachment of compounds. Bovine serum albumin was first labeled with a photocleavable NHS-biotin reagent (Pierce Chemical Company) using standard methods. The wells of a microtiter plate were then coated with approximately 10 μg photocleavable-biotin BSA (PC-biotin BSA), blocked with PBS/1% BSA, followed by the addition of 2.5 μg avidin. Biotinylated phage particles were added to each well and incubated at 4° C. for 1 hour. The wells were washed with PBS and 10 μM biotin was added to each well to prevent cross linking of the phage/streptavidin complexes. The immobilized phage were released from the surface of the wells by exposing the plate to medium wave UV light (302 nm) for 10 minutes at room temperature. BirA substrate displaying phage particles biotinylated in vivo were efficiently recovered by photolysis when captured on wells coated with photocleavable-biotin BSA and avidin as shown in FIGS. 14A and 14B.

III. Covalent Attachment of Fluorescein to Filamentous Phage Reversibly Immobilized in Microtiter Wells Phage clones, immobilized as described above, are treated with various concentrations of fluorescein-5-EX, succinimidyl ester (fluorescein-SE, available from Molecular Probes) as follows: 1)10 μL of DMSO only is added, 2) 10 μL of a 6 mM solution of fluorescein-SE in DMSO is added, 3) 10 μL of a 60 μM solution of fluorescein-SE in water is added, 4) 10 μL of a 600 nM solution of fluorescein-SE in water is added, and 5) 10 μL of a 6 mM solution of 5-(and-6)-carboxy fluorescein [5(6)-FAM, available from Molecular Probes] in DMSO is added. To all of these reactions 90 μL PBS buffer is added and incubated at 0° C. for 3 h. The wells are then washed three times with 100 μl PBS.

Following attachment of the compounds, the immobilized phage are released from the surface of the well by exposing the plate to medium wave UV light (302 nm) for 10 minutes at room temperature. Aliquots of the phage from each well are pooled in preparation for screening the library.

EXAMPLE 12

Covalent Attachment of Compounds to Filamentous and T7 Phage

I. General

Figure 15:
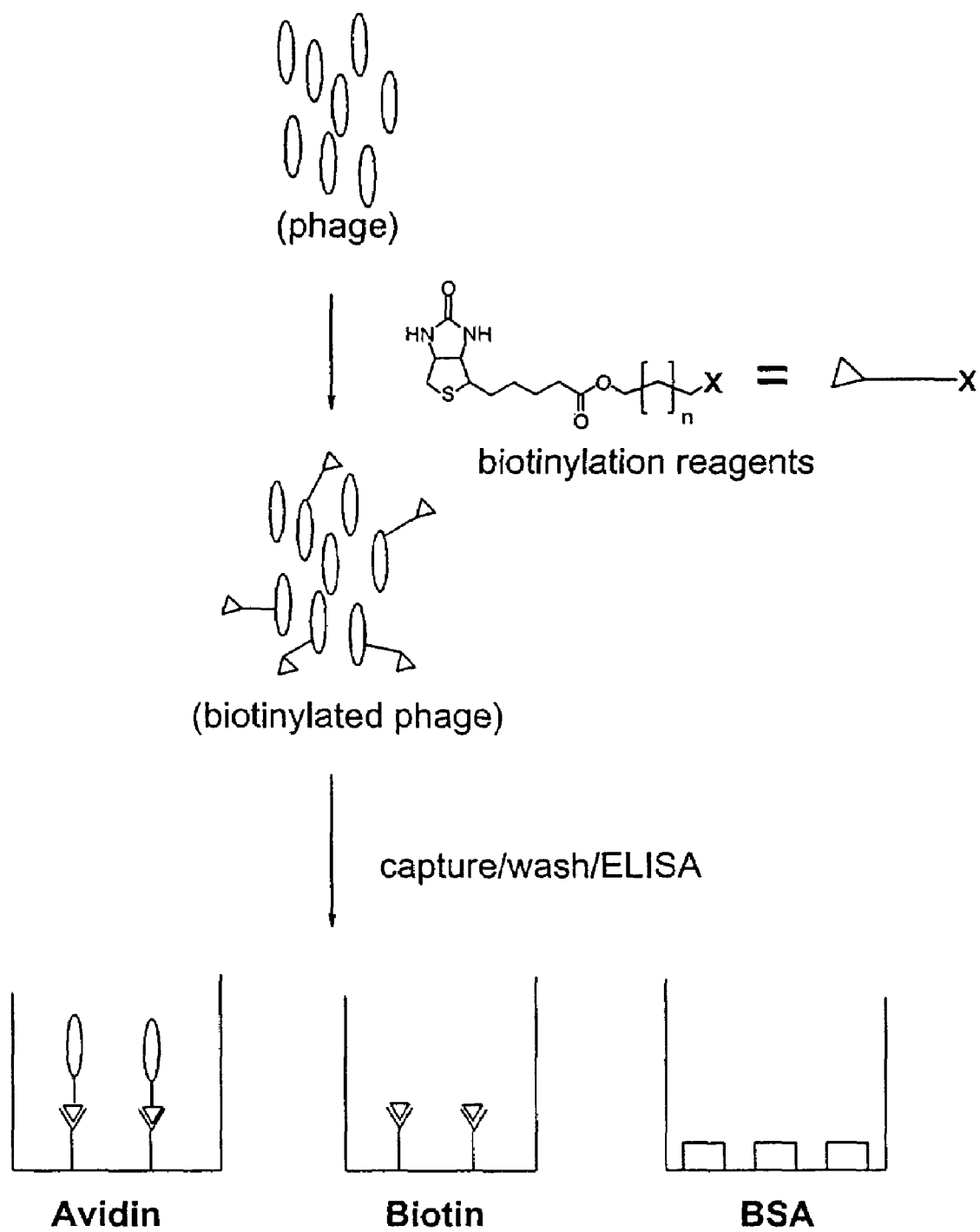
FIG. 15 summarizes the experimental design to demonstrate the chemical conjugation of biotin to phage.

This example describes an experimental system utilized to validate various strategies for covalently attaching small molecules to the coat proteins of filamentous and T7 phage. A representative small molecule was chosen, the successful attachment of which would indicate that a similar strategy could be employed to attach a variety of small molecules. Biotin served as this pilot small molecule, as its covalent attachment to the surface of phage can be easily detected due to its very strong and specific interaction with streptavidin. The experimental system used to validate the chemical conjugation of biotin to phage is depicted in FIG. 15.

This experiment entailed treating phage with various biotinylation reagents to covalently attach biotin to phage. Phage with covalently bound biotin were detected by first isolating the phage from excess biotinylation reagent and then adding the phage to immobilized streptavidin. The immobilized streptavidin binds biotin, thereby capturing biotinylated phage. After washing away any unbound phage, the captured phage were detected utilizing an Enzyme Linked Immunosorbent Assay (ELISA). This assay involved contacting captured phage with an anti-phage antibody that binds to captured phage. The anti-phage antibody is conjugated to horseradish peroxidase (termed anti-phage/HRP). After washing away the unbound anti-phage/HRP, a substrate of HRP is added, producing a colored product when acted on by HRP. This colored product is detected by monitoring absorbance at 450 nm. Consequently, the production of the colored HRP product indicates bound phage particles, captured via covalently attached biotin.

In order to ensure that the phage detected in this assay were captured by the specific interaction of the covalently attached biotin with immobilized streptavidin, a number of controls were included to account for non-specific binding. These controls involve first adding a large excess of biotin to the immobilized streptavidin prior to the addition of phage. The biotin binds streptavidin, blocking its ability to bind the biotin-conjugated phage. In addition, bovine serum albumin (BSA) was immobilized. Any phage captured by either immobilized BSA, or by streptavidin saturated with biotin, are not captured by the specific interaction of biotin with streptavidin, indicating the level of non-specific binding inherent in this assay.

II. Methods

A. Protocols for Covalent Attachment of Biotin to Filamentous Phage

1. NHS Ester Conjugation Chemistry

To 100 μL of a stock solution of filamentous phage (titer=$3.6 \times 10^{12}$ TU/mL) in PBS buffer was added 10 μL of a 6 mM aqueous solution of Sulfo-NHS-LC-biotin (available from Pierce). 90 μL of PBS buffer was added, and the solution was incubated at 0° C. for 3 h. 20 μl of aqueous 1.0 N AcOH was added, and the solution was centrifuged at 16,000×g for 10 min to pellet the phage particles. The supernatant was discarded. The phage pellet was washed gently with 10:1 PBS:1.0 N AcOH, centrifuged at 16,000×g for 10 min, and the supernatant again discarded. The phage pellet was resuspended in 500 μL PBS buffer. The procedure was repeated using 60 μM and 600 nM aqueous solutions of Sulfo-NHS-LC-biotin.

2. Maleimide Conjugation Chemistry

To 100 μL of a stock solution of filamentous phage (titer=$3.6 \times 10^{12}$ TU/mL) in PBS buffer was added 10 μL of a 6 mM aqueous solution of PEO-maleimide-biotin (available from Pierce). 90 μL of PBS buffer was added, and the solution was incubated at room temperature for 2 h. 20 μL of aqueous 1.0 N AcOH was added, and the solution was centrifuged at 16,000×g for 10 min to pellet the phage particles. The supernatant was discarded. The phage pellet was washed gently with 10:1 PBS: 1.0 N AcOH, centrifuged at 16,000×g for 10 min, and the supernatant again discarded. The phage pellet was resuspended in 500 μL PBS buffer. The procedure was repeated using 60 μM and 600 nM aqueous solutions of PEO-maleimide-biotin.

3. Amine/Carbodiimide Conjugation Chemistry

To 100 μL of a stock solution of filamentous phage (titer=$3.6 \times 10^{12}$ TU/mL) in 0.1 M MES buffer was added 10 μL of a 6 mM aqueous solution of 1-ethyl-3-(3-dimethylaminopropyl)carbodiimide (EDAC, available from Pierce) and 10 μL of a 6 mM aqueous solution of Biotin-LC-PEO-Amine (available from Pierce). 80 μL of PBS buffer was added, and the solution was incubated at room temperature for 2 h. 20 μL of aqueous 1.0 N AcOH was added, and the solution was centrifuged at 16,000×g for 10 min to pellet the phage particles. The supernatant was discarded. The phage pellet was washed gently with 10:1 PBS:1.0 N AcOH, centrifuged at 16,000×g for 10 min, and the supernatant again discarded. The phage pellet was resuspended in 500 μL PBS buffer. The procedure was repeated using 60 μM and 600 nM aqueous solutions of EDAC and Biotin-LC-PEO-Amine.

4. Hydrazide Conjugation Chemistry

To 100 μL of a stock solution of filamentous phage (titer=$3.6 \times 10^{12}$ TU/mL) in PBS buffer was added a solution of Biocytin hydrazide (available from Pierce) and/or a solution of Succinimidyl-4-formyl benzoate (available from Molecular Probes). Five reactions were performed in which: 1)10 μL of a 6 mM solution of Succinimidyl-4-formyl benzoate in DMSO was added, followed by 90 μL of PBS buffer, 2) 10 μL of a 6 mM solution of Succinimidyl-4-formyl benzoate in DMSO and 80 μL of PBS buffer were added, followed by 10 μL of a 6 mM solution of Biocytin hydrazide in 0.1 M MES buffer, 3) 10 μL of a 6 mM solution of Succinimidyl-4-formyl benzoate in DMSO and 80 µL of PBS buffer were added, followed by 10 µL of a 60 µM solution of Biocytin hydrazide in 0.1 M MES buffer, 4) 10 µL of a 60 µM solution of Succinimidyl-4-formyl benzoate in water with 1% DMSO and 80 µL of PBS buffer were added, followed by 10 µL of a 6 mM solution of Biocytin hydrazide in 0.1 M MES buffer, and 5) 10 µL of a 60 µM solution of Succinimidyl-4-formyl benzoate in water with 1% DMSO and 80 µL of PBS buffer were added, followed by 10 µL a 60 µM solution of Biocytin hydrazide in 0.1 M MES buffer.

All of these reactions were initially incubated at 0° C. for 2 h with Succinimidyl-4-formyl benzoate, and then warmed to room temperature upon addition of Biocytin hydrazide and incubated 3 h. 20 µL of aqueous 1.0 N AcOH was then added, and the solution was centrifuged at 16,000×g for 10 min to pellet the phage particles. The supernatant was discarded. The phage pellet was washed gently with 10:1 PBS:1.0 N AcOH, centrifuged at 16,000×g for 10 min, and the supernatant again discarded. The phage pellet was resuspended in 500 µL PBS buffer.

5. Iodoacetamide Conjugation Chemistry

To 100 µL of a stock solution of filamentous phage (titer=3.6×10$^{12}$ TU/mL) in PBS buffer was added 10 µL of a 6 mM aqueous solution of PEO-iodoacetyl-biotin (available from Pierce). 90 µL of PBS buffer was added and the solution was incubated at room temperature for 3 h. 20 µL of aqueous 1.0 N AcOH was added, and the solution was centrifuged at 16,000×g for 10 min to pellet the phage particles. The supernatant was discarded. The phage pellet was washed gently with 10:1 PBS: 1.0 N AcOH, centrifuged at 16,000×g for 10 min, and the supernatant again discarded. The phage pellet was resuspended in 500 µL PBS buffer. The procedure was repeated using a 60 µM aqueous solution of PEO-iodoacetyl-biotin.

B. Protocols for Attachment of Biotin to T7 Phage

1. NHS Ester Conjugation Chemistry

To 100 µL of a stock solution of T7 S-Tag phage (titer=1.0× 10$^{11}$ pfu/mL; T7 S-Tag phage are T7 phage that display a 15-amino acid peptide fused to the C-terminus of the major coat protein that binds to ribonuclease S-protein) in PBS buffer was added 10 µL of a 6 mM aqueous solution of Sulfo-NHS-LC-biotin (available from Pierce). 90 µL of PBS buffer was added, and the solution was incubated at 0° C. for 3 h. 50 µL of 50% PEG was added to each reaction vial, cooled to 0° C. and centrifuged at 16,000×g for 5 min. The supernatant was discarded, and the phage pellet was resuspended in 500 µL PBS buffer. The procedure was repeated using 60 µM and 600 nM aqueous solutions of Sulfo-NHS-LC-biotin.

2. Maleimide Conjugation Chemistry

To 100 µL of a stock solution of T7 S-Tag phage (titer=1.0× 10$^{11}$ pfu/mL; T7 S-Tag phage are T7 phage that display a 15-amino acid peptide fused to the C-terminus of the major coat protein that binds to ribonuclease S-protein) in PBS buffer was added 10 µL of a 6 mM aqueous solution of PEO-maleimide-biotin (available from Pierce). 90 µL of PBS buffer was added, and the solution was incubated at room temperature for 2 h. 50 µL of 50% PEG was added to each reaction vial, cooled to 0° C. and centrifuged at 16,000×g for 5 min. The supernatant was discarded, and the phage pellet was resuspended in 500 µL PBS buffer. The procedure was repeated using 60 µM and 600 nM aqueous solutions of PEO-maleimide-biotin.

3. Amine/Carbodiimide Conjugation Chemistry

To 100 µL of a stock solution of T7 S-Tag phage (titer=1.0× 10$^{11}$ pfu/mL; T7 S-Tag phage are T7 phage that display a 15-amino acid peptide fused to the C-terminus of the major coat protein that binds to ribonuclease S-protein) in PBS buffer was added 10 µL of a 6 mM aqueous solution of 1-ethyl-3-(3-dimethylaminopropyl)carbodiimide (EDAC, available from Pierce) and 10 µL of a 6 mM aqueous solution of Biotin-LC-PEO-Amine (available from Pierce). 80 µL of PBS buffer was added, and the solution was incubated at room temperature for 2 h. 50 µL of 50% PEG was added to each reaction vial, cooled to 0° C. and centrifuged at 16,000×g for 5 min. The supernatant was discarded, and the phage pellet was resuspended in 500 µL PBS buffer. The procedure was repeated using 60 µM and 600 nM aqueous solutions of EDAC and Biotin-LC-PEO-Amine.

C. Methods For Detection of Covalent Conjugation of Biotin to Phage

1. Detection of Biotinylated Filamentous Phage (a) Microtiter Plate Preparation: NeutrAvidin and two controls of biotin saturated-NeutrAvidin and BSA were immobilized according to the following procedure. 50 µL of a 100 ug/mL solution of NeutrAvidin (available from Pierce) was added to each well of columns 1-4 and 7-10 of a 96 well microtiter plate. The plate was covered, incubated at 37° C. for 1 h, and washed with PBS. 300 µL of 1% BSA/PBS was added to each well of the plate, incubated overnight at 4° C., and washed with PBS. 50 µL of 0.1% BSA/PBS was added to each well of columns 1,2,5-8, 11 and 12, and 50 µL of 0.1% BSA/PBS containing 20 µM biotin was added to each well of columns 3,4,9 and 10.

(b) Capture and Detection of Biotinylated Filamentous Phage: 50 µL of the biotinylated filamentous phage solutions, prepared in part II. A. 1-5 in this Example, were added to the first 6 wells of a row, which included duplicates of Neutravidin, biotin saturated-NeutrAvidin and BSA. In addition to phage treated with the biotin-conjugation conditions described above, the following controls were included: filamentous phage treated with no biotinylation reagent, and filamentous phage treated only with Succinimidyl-4-formyl benzoate. Following addition of the phage preparations, the microtiter plate was incubated overnight at 4° C. The plate was then washed with PBS, and 100 µL of a 1:5000 dilution of anti-M13 monoclonal antibody conjugated with horseradish peroxidase (anti-phage/HRP) in 0.1% BSA/PBS was added to each well. The plate was incubated at room temperature for 1 h, and washed with PBS. 100 µL of substrate solution (18 µL of 30% $H_2O_2$ added to 10 mL 1×ABTS) was added to each well, and the absorbance at 405 nm was measured in a microtiter plate reader.

2. Detection of Biotinylated T7 Phage (a) Microtiter Plate Preparation: The microtiter plate was prepared as described above.

(b) Capture and Detection of Biotinylated T7 S-tag Phage: 50 µL of the biotinylated T7 S-tag phage solutions, prepared in part II.B.1-3 in this Example, were added to the first 6 wells of a row, which included duplicates of Neutravidin, biotin saturated-NeutrAvidin and BSA. In addition to phage treated with the biotin-conjugation conditions described above, a control experiment of untreated T7 S-tag phage was included. Following addition of the phage preparations, the microtiter plate was incubated overnight at 4° C. The plate was then washed with PBS, and 50 µL of a 1:5000 dilution of S-protein conjugated with horseradish peroxidase (S-protein/HRP, available from Novagen) in 0.1% BSA/PBS was added to each well. The plate was incubated at room temperature for 2 h, and washed with PBS. 100 µL of substrate solution (18 µL of 30% $H_2O_2$ added to 10 mL 1×ABTS) was added to each well, and the absorbance at 405 nm was measured in a microtiter plate reader.

III. Results

Figure 16A:
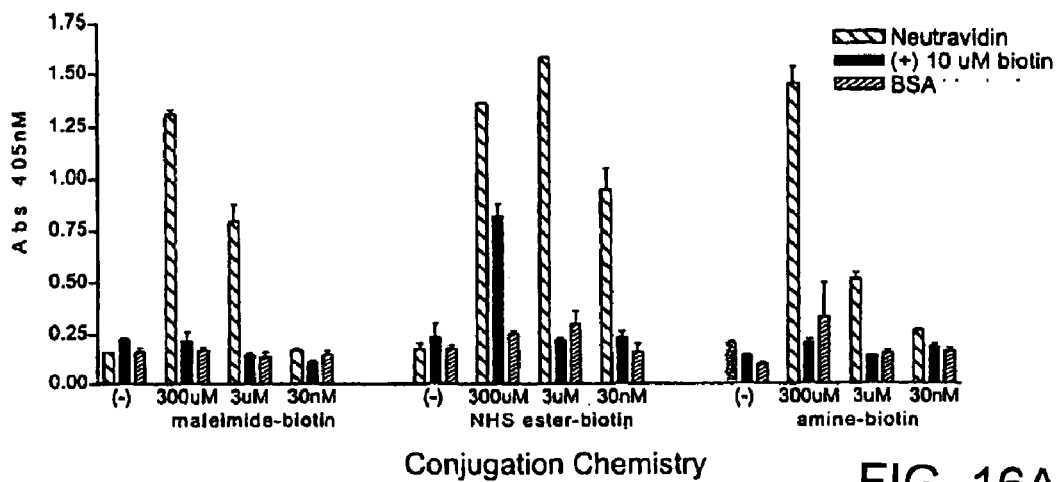
FIGS. 16A-16C present ELISA results for the detection of biotinylated phage captured by immobilized Neutravidin.
Figure 16B:
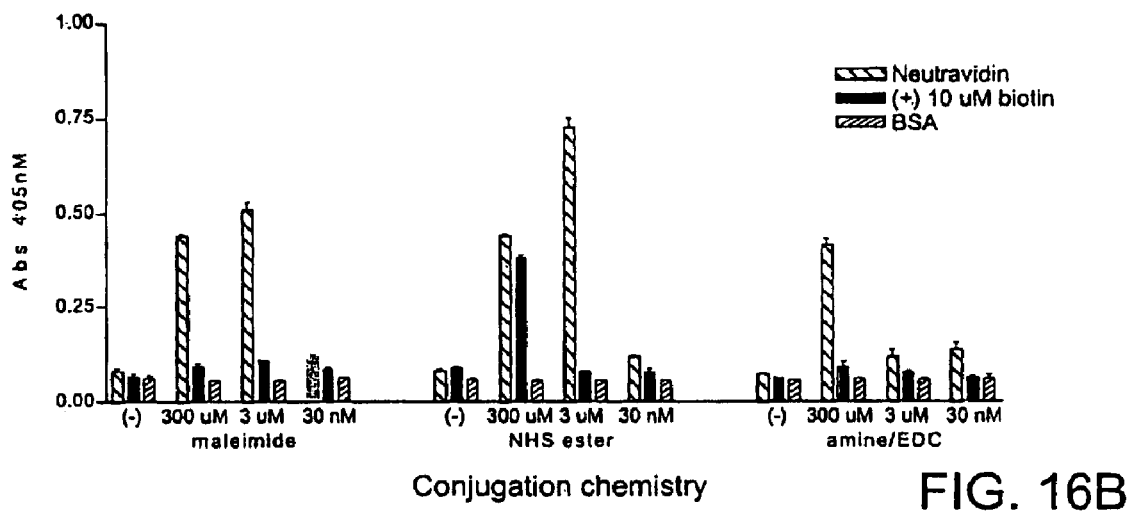
Figure 16C:
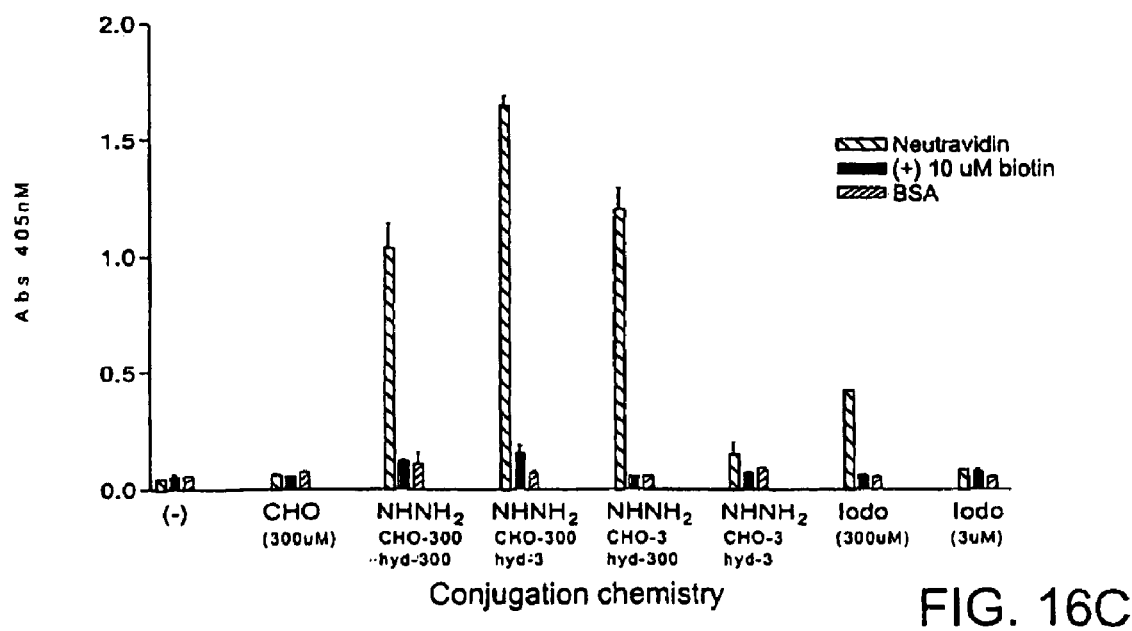

The data from the foregoing ELISA assays are presented in FIGS. 16A-16C. FIG. 16A illustrates the use of NHS ester, maleimide and amine/carbodiimide chemistry to conjugate biotin to the surface of filamentous phage. FIG. 16C shows the use of hydrazide and iodoacetamide attachment chemistry in conjugating biotin to filamentous phage. FIG. 16B shows the results of the use of NHS ester, maleimide and amine/carbodiimide chemistry with T7 phage. In all these ELISA assays, a strong signal is detected when the phage were treated with 300 μM of the biotinylation reagent. This signal drops when the phage were treated with 3 μM or 30 nM of the biotinylation reagents. The NHS ester attachment chemistry appears to be the most robust, as it produces a strong signal even at the lowest concentration of 30 nM. In addition, the controls for all these experiments have low signals, indicating that the biotinylated phage are specifically bound to NeutrAvidin.

EXAMPLE 13

Determination of the Infectivity of Phage Treated under Biotinylation Conditions I. General Having determined that a variety of attachment chemistries serve to conjugate biotin to both filamentous and T7 phage, the effect this has on the ability of the phage to infect bacterial host cells was examined. This was determined by simply measuring the titer of phage populations treated with various biotinylation reagents. Determining the titer of a phage population counts the number of infective phage particles in that population. The assay consists of adding the phage to an excess of host bacterial cells. The bacterial cells are then plated on the appropriate growth medium and incubated at 37° C. The number of bacterial colonies or plaques that form determines the number of infective phage particles. If attaching biotin to phage abrogates their ability to infect host bacterial cells, this would be detected as a decrease in the titer of that phage population.

II. Methods

A. Titer Determination of Filamentous Phage

100 μL of E. coli K91recA cells at log phase were inoculated with 10 μL of appropriate dilutions of the preparations of biotinylated filamentous phage. These were plated onto LB/amp plates and incubated overnight at 37° C. The colonies were counted to determine the titer of the phage preparation.

B. Titer Determination of T7 Phage

200 μL of E. coli BL 21 cells at log phase were inoculated with 100 μL of the biotinylated T7 phage preparations. This was suspended in 3 mL of warm top agar, plated onto agar plates and incubated overnight at room temperature. The plaques were counted to determine the titer of the phage preparation.

III. Results

Figure 17A:
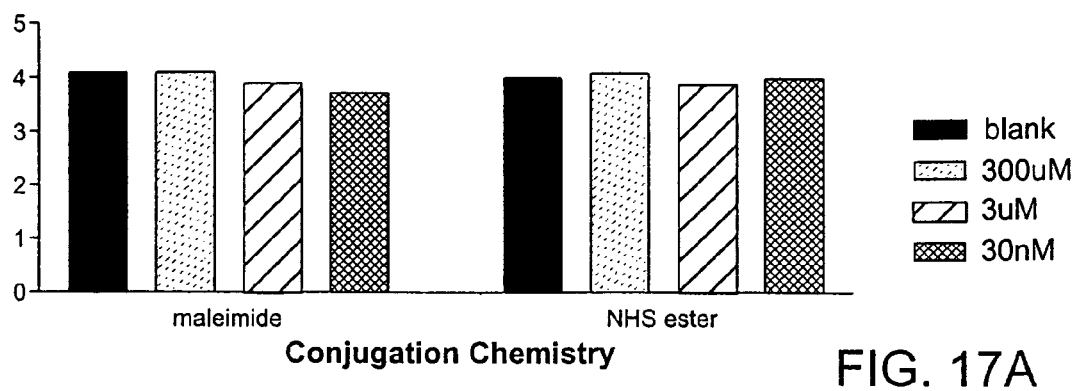
FIGS. 17A-17C show the effect of chemical conjugation of biotin with different chemistries.
Figure 17B:
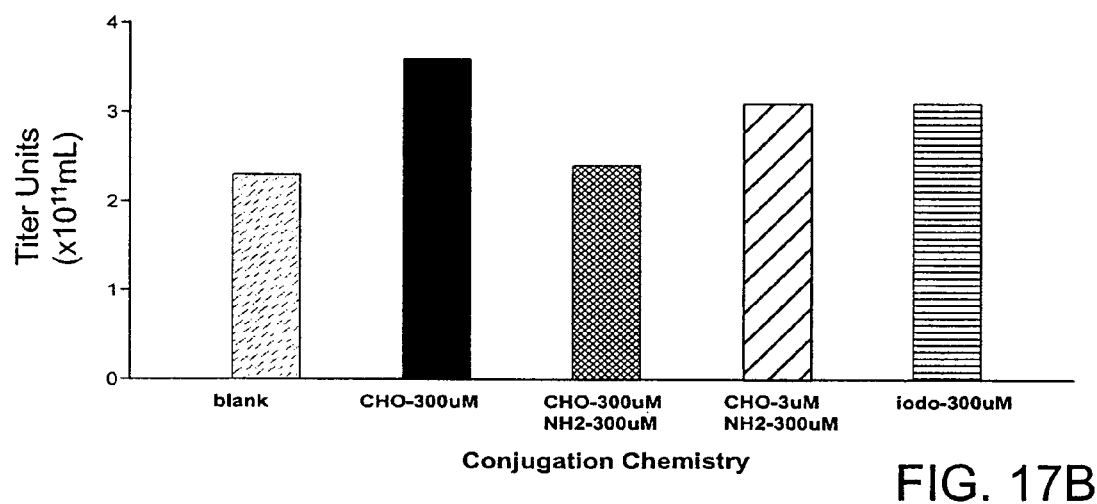
Figure 17C:
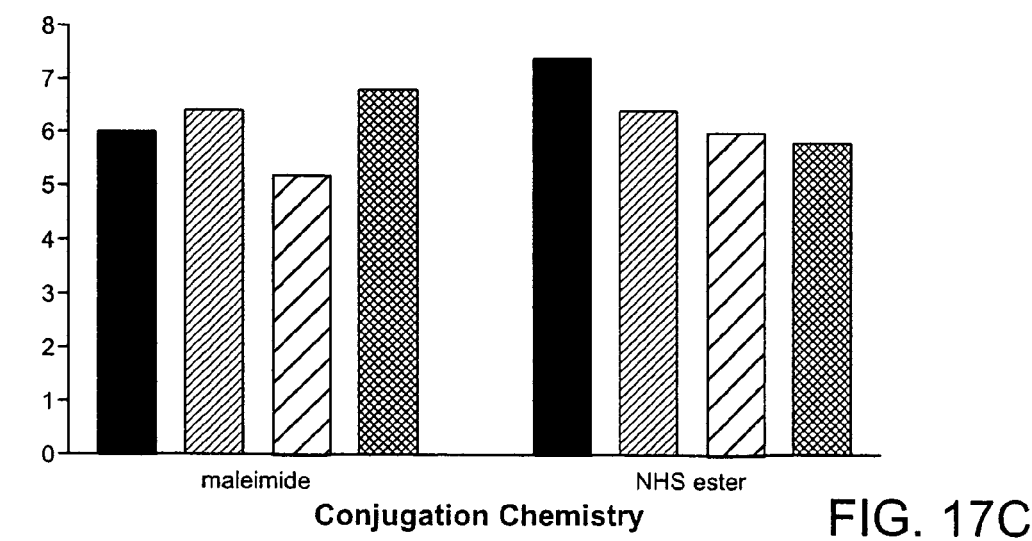

FIGS. 17A-17C demonstrate that conjugating biotin to both filamentous and T7 phage using maleimide, NHS ester, hydrazide or iodoacetamide attachment chemistries has no detrimental effect on the infectivity of those phage as the infectivity was not adversely effected by any of the conjugation methods.

EXAMPLE 14

Identification of Attachment Sites for Biotin in Filamentous and T7 Phage

I. General

The experiments described above demonstrate that several different attachment chemistries are able to conjugate biotin to phage, without interfering with their ability to infect host bacterial cells. In order to characterize which coat protein serves as the site of attachment, and to determine the extent of conjugation, fluorescein was attached to phage. Protein gel analysis allows for determination of which coat protein is fluoresceinated.

II. Methods

A. Covalent Attachment of Fluorescein

1. Filamentous Phage

Five reactions were run in which 100 μL of a stock solution of a clone of filamentous phage that contains a unique sequence tag at the 5' end of gene VIII (clone=ON5/6-#4, titer=1×10$^{12}$ TU/mL) were treated with various concentrations of fluorescein-5-EX, succinimidyl ester (fluorescein-SE, available from Molecular Probes): 1) 10 μL of DMSO only added, 2) 10 μL of a 6 mM solution of fluorescein-SE in DMSO added, 3) 10 μL of a 60 μM solution of fluorescein-SE in water added, 4) 10 μL of a 600 nM solution of fluorescein-SE in water added, and 5) 10 μL of a 6 mM solution of 5-(and-6)-carboxy fluorescein [5(6)-FAM, available from Molecular Probes] in DMSO added. To all of these reactions was added 90 μL PBS buffer and incubated at 0° C. for 3 h. 20 μL of 1.0 N AcOH was added to each tube and spun at 16,000×g for 10 min. The supernatant was removed, and the phage pellet was gently washed with 200 μL of 10:1 PBS: 1.0 N AcOH. The phage were again precipitated by spinning at 16,000×g for 10 min, and the supernatant was discarded. The phage pellet was resuspended in 500 μL PBS buffer.

2. T7 Phage

Five reactions were run in which 200 μL of a stock solution of T7 S-Tag phage (titer=1×10$^{11}$ TU/mL, T7 S-Tag phage are T7 phage that display a 15 amino acid peptide fused to the C-terminus of the major coat protein that binds to ribonuclease S-protein) were treated with various concentrations of fluorescein-5-EX, succinimidyl ester (fluorescein-SE, available from Molecular Probes): 1) 20 μL of DMSO only added, 2) 10 μL of a 6 mM solution of fluorescein-SE in DMSO added, 3) 20 μL of a 60 μM solution of fluorescein-SE in water added, 4) 20 μL of a 600 nM solution of fluorescein-SE in water added, and 5) 10 μL of a 6 mM solution of 5-(and-6)-carboxy fluorescein [5(6)-FAM] in DMSO added. To all of these reactions was added 180 μL PBS buffer and incubated at 0° C. for 3 h. 100 μL of 50% PEG was added to each tube and spun at 16,000×g for 5 min. The supernatant was removed, and the phage pellet was resuspended in 400 μL PBS. 100 μL 50% PEG was added, cooled to 0° C. and spun at 16,000×g for 5 min. The supernatant was again removed, and the pellet resuspended in 500 μL PBS buffer.

B. Protein Gel to Identify Coat Protein to which Fluorescein is Attached

1. Gel for Filamentous Phage

The fluoresceinated filamentous phage prepared in reaction #2 as described in part II. A. 1 of this Example were diluted a total of 128 fold by a series of eight 2-fold dilutions with PBS buffer as the diluent. In addition, the phage preparation from reaction #5 as described in part II. A. 1 of this Example was diluted 10 fold with PBS as the diluent. To 15 μL of each of these dilutions was added 5 μL of 4× sample buffer and heated at 80° C. for 1 h. These were centrifuged at 16,000×g for 1 min, then loaded onto a 4-12% Bis-Tris gel such that the dilutions from reaction #2 were in lanes 1-8, lane 9 contained MW markers, and lanes 10 and 11 contained the dilutions from reaction #5. The gel was run at 200 V for 30 min, then soaked in fixing buffer (50% MeOH/10% Acetic Acid/40% $H_2O$) overnight, followed by equilibration in PBS buffer for 3 h. The gel was visualized to detect those bands that contained fluorescein, then stained with SYPRO Ruby (available from Molecular Probes) for 4 h, followed by washing with PBS for 1 h and visualized to detect all the protein bands on the gel.

2. Gel for T7 Phage

The T7 phage preparations from reaction #1 and #2 in part II. A. 2 of this Example were diluted by 2× and 4× and run on a protein gel, with decreasing dilutions of sample #1 run in Lanes 1-3 and decreasing dilutions of sample #2 run in Lanes 4-6 respectively. The samples were prepared by adding 5 µL of 4× sample buffer to 15 µL of the indicated dilution and heated at 80° C. for 1 h. These were then loaded onto a 4-12% Bis-Tris gel and run at 200 V for 30 min. The gel was soaked in fixing buffer (50% MeOH/10% Acetic Acid/40% $H_2O$) overnight, followed by equilibration in PBS buffer for 3 h. The gel was visualized to detect those bands that contained fluorescein, then stained with SYPRO Ruby for 4 h, followed by washing with PBS for 1 h and visualized to detect all the protein bands on the gel.

III. Results

Protein gel analysis allows for determination of which coat protein is fluoresceinated. FIGS. 18A and 18B show the result of this experiment with filamentous phage. This figure shows two images of the same protein gel. Image A shows all the proteins on the gel. The major band visible in lanes 1,2 and 10 is the p8 coat protein. This protein constitutes 95% of the total protein content of filamentous phage particles, and, not surprisingly, is the only protein visible by protein staining. Image B shows only fluoresceinated proteins, clearly illustrating that, as expected, p8 is the main site of attachment. Control lanes 10 and 11, which contain phage treated with fluorescein-carboxylic acid instead of fluorescein-NHS ester, do not contain fluoresceinated proteins suggesting that the covalent attachment of fluorescein is due to the specific reaction of fluorescein-NHS ester with an available amine, either the side chain of lysine 8 or the free N-terminus or of the p8 coat protein.

T7 phage were treated with fluorescein-NHS ester as well. The results of this experiment are shown in FIGS. 19A and 19B. The two images are again of the same protein gel. Image A visualizes all the proteins on the gel, while image B visualizes only those proteins that have been fluoresceinated. The major band evident in lanes 1-6 of image A is the gene 10 capsid protein. Image B clearly shows that this is the major site of attachment in T7 phage, although other minor coat proteins may be labeled as well.

EXAMPLE 15

Quantifying the Amount of Fluorescein Incorporated into Phage Coat Protein

I. General

The extent of conjugation of filamentous phage was characterized by determining the number of fluorescein molecules per phage particle. This entailed first detecting the amount of fluorescein in a sample of fluoresceinated phage, then dividing by the number of phage particles in that sample. The amount of fluorescein was determined by comparing it with a known standard (NeutrAvidin-FITC). A calibration curve was generated by plotting the fluorescence intensity vs. fluorescein concentration of these samples. Plotting the fluorescence intensity of the fluoresceinated phage samples on this curve determined the amount of fluorescein in that sample.

The number of filamentous phage particles per sample was determined by quantitating the amount of phage DNA present. Titering the phage sample does not provide a reliable evaluation of the total number of phage particles. Titering phage only detects infective phage particles while phage preparations contain non-infective as well as infective phage. The amount of phage DNA per sample was determined by comparing it with a calibration curve generated by loading known amounts of DNA onto an agarose gel.

II. Methods

A. Gel to Quantify the Amount of Fluorescein Incorporated in Phage Coat Protein

The fluoresceinated filamentous phage prepared in reaction #2 as described in Example 14 II. A. 1 were diluted a total of 16 fold by a series of four 2-fold dilutions with PBS buffer as the diluent. Five 2-fold dilutions of FITC-conjugated NeutrAvidin were similarly prepared (concentrations=134 ug/mL, 67 ug/mL, 34 ug/mL, 17 ug/mL, and 8.5 ug/mL). To 15 µL of these samples was added 5 µL of 4× sample buffer. These samples were heated at 80° C. for 10 min and loaded onto a 4-12% Bis-Tris protein gel. The gel was run at 200 V for 30 min, then washed in fixing buffer (50% MeOH/10% AcOH/40% $H_2O$) for 1 h, followed by washing in 5% MeOH/7.5% AcOH/87.5% $H_2O$ overnight. The gel was equilibrated in PBS for 4 h, then visualized to determine the amount of fluorescence in each lane. A calibration curve was created plotting fluorescence intensity vs. amount of fluorescein, using FITC-conjugated NeutrAvidin as the standard, to determine the amount of fluorescein incorporated into the phage coat protein.

B. Gel to Determine the Number of Phage Particles per Sample

An 0.8% agarose DNA gel was run with the following samples: Lane 1=MW marker, Lanes 2-6=purified p8 Xeno single stranded DNA with 100 ng, 50 ng, 10 ng, 5 ng and 1 ng of DNA in lanes 2-6 respectively, Lane 10=MW marker, and Lanes 11-13=fluorescein-labeled phage with Lane 11 containing the sample analyzed in part II. A of this Example, and Lanes 12 and 13 containing 2× and 4× dilutions respectively. The purified DNA samples were prepared by adding 2 µL of 5× loading dye to 10 µL of sample prior to loading onto the gel. The fluorescein-labeled phage samples were prepared by adding 5 µL of 2% SDS to 5 µL of phage sample at the indicated dilution and incubating at 80° C. for 10 min. 2 µL of 5× loading dye was added and the sample loaded onto the gel. The gel was run at 110 V for 30 min in 1×TBE with 0.1 ug/mL ethidium bromide, then visualized using a 532 nm excitation line and 610 nm emission filter on a TYPHOON imager (Molecular Dynamics). A calibration curve plotting fluorescence intensity vs. amount of DNA was generated using the purified p8 Xeno DNA as a standard to determine the number of phage particles present in the sample. This calculation was combined with the above determined number of fluorescein molecules per phage sample to determine the number of fluorescein molecules per phage particle obtained upon treating phage with various concentrations of fluorescein-NHS ester.

III. Results

When treated with 300 μM fluorescein-NHS ester, an average of 280 fluorescein molecules per filamentous phage are attached. This corresponds to roughly one in every 10 copies of the p8 coat protein being conjugated with fluorescein. Treating phage with 3 μM fluorescein-NHS ester results in an average of 17 fluorescein molecules per Filamentous phage particle. The same experiment was carried out with T7 phage. These results were not conclusive as preparations of T7 phage contain a high level of the gene 10 capsid protein not incorporated into intact phage particles. Labeling of the unincorporated capsid protein complicates interpretation of the data.

EXAMPLE 16

ELISA Detection of Fluorescein-Conjugated T7 S-Tag Phage

I. General

Another set of experiments was conducted to determine if fluoresceinated T7 phage could be captured by immobilized anti-fluorescein antibody similar to the ability of biotinylated phage to be captured.

II. Methods

50 μL of a 0.1 mg/mL solution of mouse monoclonal anti-fluorescein antibody (Molecular Probes) was added to columns 1 and 2 of a 96-well microtiter plate and incubated at 37° C. for 1.5 h. The plate was washed with PBS, and 300 μL of 0.1% BSA/PBS was added to each well of columns 1-4 and incubated at 37° C. for 3 h. The plate was washed and 50 μL of 0.1% BSA/PBS was added to each well, followed by 50 μL of a 10× dilution of each of the phage solutions prepared in Example 14 II.A.2 reactions 1-5. The plate was incubated overnight at 4° C., and washed with PBS. 50 μL of S-protein-horseradish peroxidase conjugate (1:5000 dilution in 0.1% BSA/PBS) was added and incubated at room temperature for 2 h. The plate was washed, and 100 μL of substrate (9 μL of 30% $H_2O_2$ added to 5 mL of 1×ABTS) was added. The absorbance at 405 nm was measured in a microtiter plate reader.

III. Results

Figure 20:
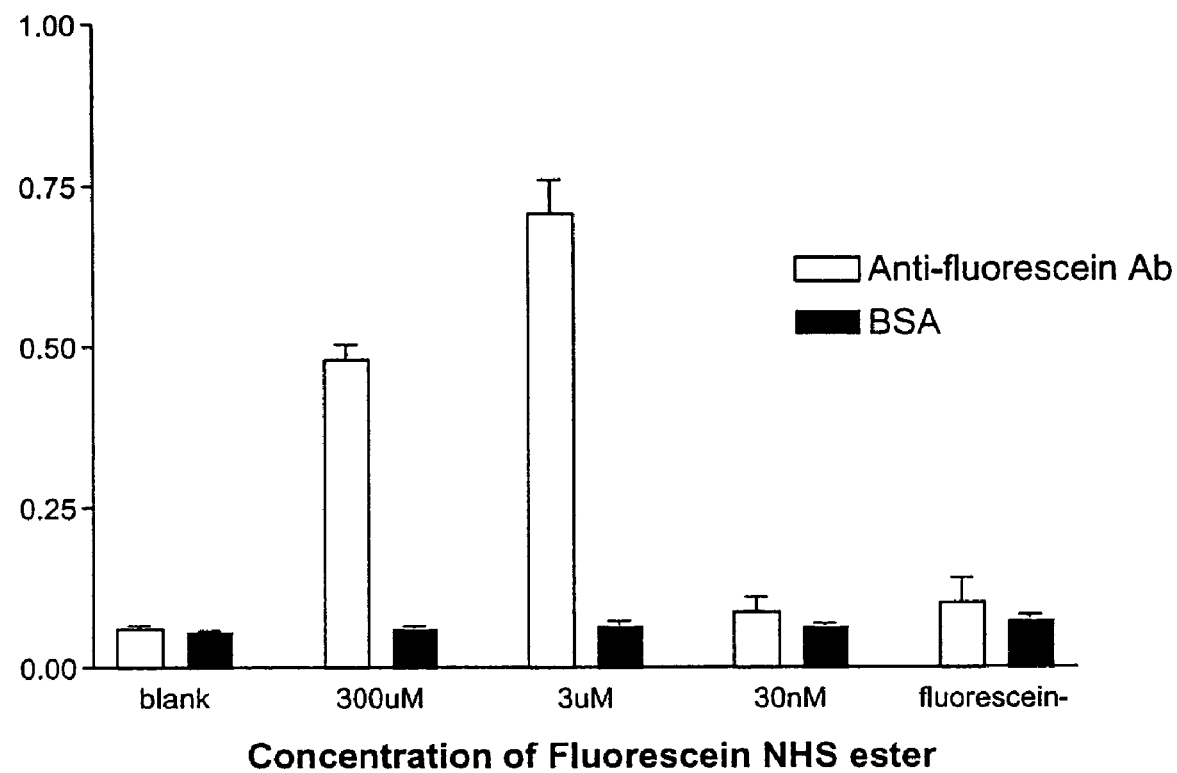
FIG. 20 depicts results of ELISA detection of fluorescein-conjugated T7 phage captured by immobilized anti-fluorescein antibody. The fluorescein was chemically conjugated to the phage using NHS ester attachment chemistry.

The ability of the immobilized anti-fluorescein antibodies to capture T7 phage reacted with varying concentrations of fluorescein are shown in FIG. 20. Phage reacted at 300 μM and 3 μM bound specifically to the immobilized anti-fluorescein antibody.

EXAMPLE 17

Selection of Fluorescein-Conjugated Phage from a Background of Unmodified Phage

I. General

Figure 21:
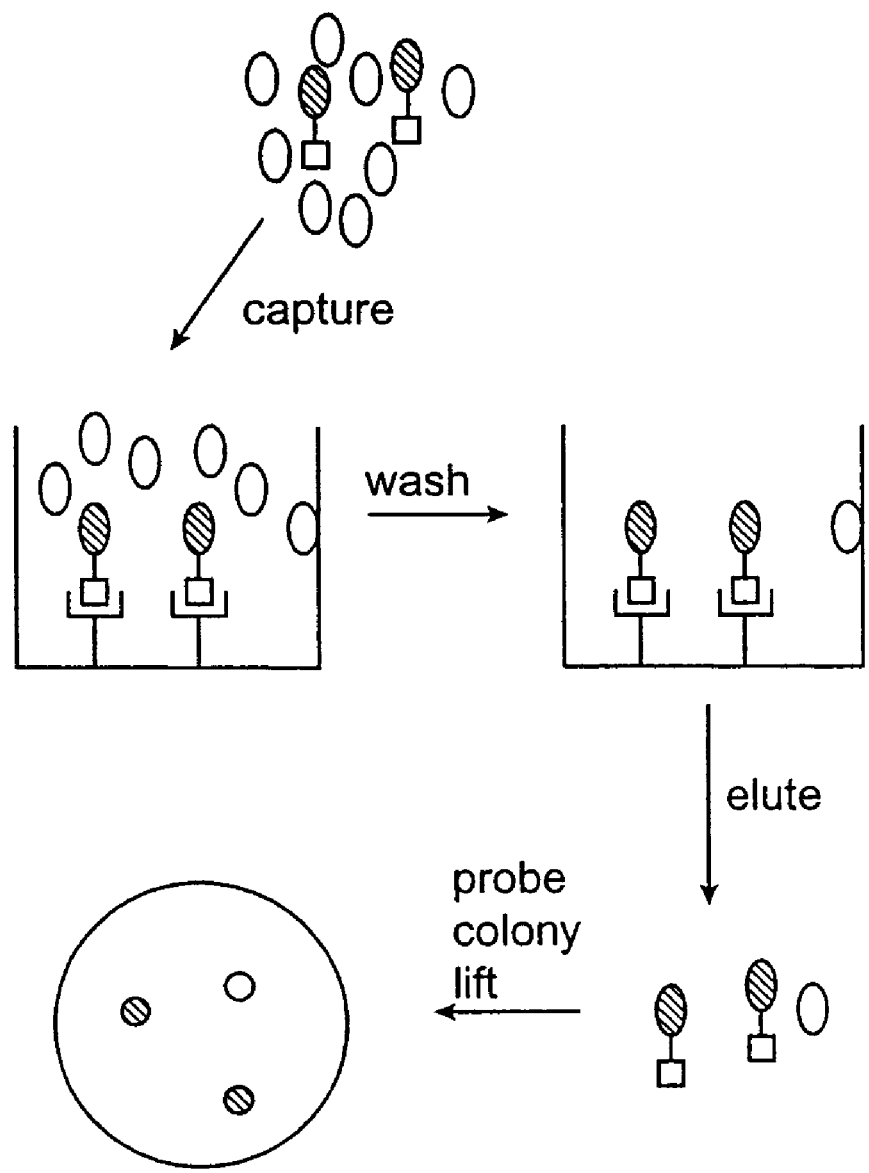
FIG. 21 illustrates the experimental design to select fluorescein-conjugated phage from a background of unmodified phage.

Fluoresceinated phage captured as described in the preceding example can be recovered by releasing them from immobilized anti-fluorescein with an acidic elution buffer. As a result, one can determine the fold enrichment achievable upon using immobilized anti-fluorescein to select fluoresceinated phage out of a background of unmodified phage. A schematic representation of this experiment is presented in FIG. 21. At the outset, a phage population is generated in which a known amount of a fluoresceinated phage clone is spiked into a background of unmodified phage. The fluoresceinated phage clone is identifiable by a unique DNA insert. This phage population is added to immobilized anti-fluorescein. After washing away unbound phage, the bound phage are eluted under acidic conditions. The percent of the eluted phage population comprised of the target fluoresceinated phage clone is ascertained by infecting host bacterial cells with the eluted phage and determining the fraction that have been infected with the target clone via hybridization of an oligonucleotide probe complementary to the unique DNA insert of the target clone.

II. Methods

A. Preparation of Additional Fluorescein Conjugated Filamentous Phage for Screening Experiment Two reactions were run in which 300 μL of a stock solution of a clone of filamentous phage that contains a unique sequence tag at the 5' end of gene VIII (clone=ON5/6-#4, titer=1×10$^{12}$ TU/mL) were treated with fluorescein-5-EX, succinimidyl ester (fluorescein-SE, available from Molecular Probes): 1) 30 μL of a 0.6 mM solution of fluorescein-SE in water added, and 2) 30 μL of a 60 μM solution of fluorescein-SE in water added. To both of these reactions was added 270 μL PBS buffer and incubated at 4° C. for 3 h. 60 μL of 1.0 N AcOH was added to each tube and spun at 16,000×g for 10 min. The supernatant was removed, and the phage pellet was gently washed with 600 μL of 10:1 PBS: 1.0 N AcOH. The phage were again precipitated by spinning at 16,000×g for 10 min, and the supernatant was discarded. The phage pellet was resuspended in 600 μL PBS buffer.

B. Selection of Fluorescein-Conjugated Phage

Three microtiter plates were prepared in which 50 μL of a 0.05 mg/mL solution of anti-fluorescein antibody was added to column 1 and incubated at 37° C. for 1.5 h. The plate was washed and 300 μL of 1% BSA/PBS was added to the first and last columns and incubated at 37° C. for 2 h. The plates were washed, then 50 μL of 0.1% PBS/BSA was added to the first and last columns. The following samples were added to the indicated plates: Plate #1: 50 μL of a solution of p8 Xeno (titer=10$^{11}$ TU/mL) was added to the first 2 wells of the first and last columns. Plate #2: 50 μL of a solution of p8 Xeno (titer=10$^{11}$ TU/mL) spiked with fluoresceinated phage prepared in reaction #1 of part A above such that the titer of the fluoresceinated phage was 10$^7$ TU/mL was added to the first 2 wells of the first and last column. 50 μL of a solution of p8 Xeno (titer=10$^{11}$ TU/mL) spiked with fluoresceinated phage prepared in reaction #2 of part A above such that the titer of the fluoresceinated phage was 10$^7$ TU/mL was added to the last 2 wells of the first and last column. Plate #3: 50 μL of a solution of p8 Xeno (titer=10$^{11}$ TU/mL) spiked with fluoresceinated phage prepared in reaction #1 of part A above such that the titer of the fluoresceinated phage was 10$^5$ TU/mL was added to the first 2 wells of the first and last column. 50 μL of a solution of p8 Xeno (titer=10$^{11}$ TU/mL) spiked with fluoresceinated phage prepared in reaction #2 of part A above such that the titer of the fluoresceinated phage was 10$^5$ TU/mL was added to the last 2 wells of the first and last column.

These three plates were incubated overnight at 4° C., then washed with PBS. 100 μL of acid elution buffer (0.1 N HCl, pH 2.2 with glycine, 0.1% BSA) was added to each well to which phage had been added and incubated at room temperature for 10 min. The eluant from the two duplicate wells were combined and neutralized with 15.6 μL of 1.5 M Tris. 10 μL of the neutralized eluant (except for both samples from the fist column of Plate #2, which were first diluted 100×, and the sample from the last wells of the first column of Plate #3, which was first diluted 10×) was added to 100 μL of K91 RecA cells at log phase, incubated at 37° C. for 20 min, then plated onto LB plates containing ampicillin and incubated overnight at 37° C.

The resultant colonies on these plates (as well as two control plates, one of which contained only the background phage p8 Xeno, the other containing only the fluorescein conjugated clone ON5/6-#4) were lifted onto nitrocellulose filters, then washed in denaturation buffer (0.5 N NaOH, 1.5 M NaCl) for 5 min, followed by neutralization buffer (1.5 M NaCl, 0.5 M Tris, pH=7.5) for 5 min and 2×SSPE for 5 min. The filters were dried in a gel dryer at 80° C. for 2 h and washed in 2×SSPE with 0.1% SDS for 15 min. The filters were added to a hybridization bag and incubated in 19 mL complete hybridization solution for 30 min at 62° C., at which point 100 μL of a radiolabeled probe ($1\times10^4$ cpm/μL) specific for the heterologous nucleotide tag in clone ON5/6-#4 was added and hybridized overnight at 62° C. The filters were washed in 2×SSPE with 0.1% SDS for 20 min, dried and exposed to a phosphor screen for 18 h. The screen was then scanned with the TYPHOON imager to reveal the colonies to which the probe had hybridized.

III. Results

This experiment was conducted with $\frac{1}{10}^4$ and $\frac{1}{10}^6$ dilutions of the target fluoresceinated phage clone into a background of unmodified phage. The data are presented in Tables 1. As control experiments, phage populations containing no target fluoresceinated clones were screened and produced no positive hybridization signals, as expected. The indicated dilutions were also screened with immobilized BSA, and no target clone was identified at either dilution when up to 300 colonies were probed, as expected. Screening the $\frac{1}{10}^6$ dilution of phage treated with 30 μM fluorescein-NHS ester with immobilized anti-fluorescein resulted in an eluant population of phage in which 72% were the target clone, or an enrichment of $7\times10^5$ fold. Further, 60% of the total number of input target phage was recovered.

EXAMPLE 18

Construction and Screening of a Collection of Uniquely-Tagged Phage Particles Displaying Covalently-Attached Small Molecules I. General Example 17 demonstrates that fluoresceinated phage can be selected from a background of unmodified phage via specific binding to immobilized anti-fluorescein antibody. To better emulate screening libraries of small molecules, a collection of phage clones conjugated to fluors other than fluorescein was prepared to determine whether each individual clone could be selected out of a background of similarly modified phage. The additional fluors chosen for this purpose were BODIPY, dansyl and Texas Red, each of which has a corresponding antibody that can be used during selection. Three distinct phage clones were modified with either 3 μM BODIPY, dansyl and Texas Red, producing a panel of four fluor-conjugated phage, including the fluorescein-conjugated phage, each of which can be selected by an immobilized antibody. Each fluor-conjugated phage was screened against each immobilized antibody and detected via an ELISA assay.

II. Methods

A. Covalent Attachment of Fluors to Unique Filamentous Phage Clones

1. Attachment of BODIPY

Two reactions were run in which 300 μL of a filamentous phage clone (ON5/6-#1, titer=$1\times10^{12}$ TU/mL) that contains a unique sequence tag at the 5' end of gene VIII was treated with 30 μL of 0.6 mM BODIPY-Fl-X succinimidyl ester (BODIPY-SE, available from Molecular Probes) in reaction #1 and 30 μL of 60 μM BODIPY-SE in reaction #2. 270 μL PBS buffer were added to each reaction and incubated at 0° C. for 3 h. 60 μL of 1.0 N AcOH was added and centrifuged at 16,000×g for 10 min. The supernatant was removed, and the pellet resuspended in 600 μL PBS. 60 μL 1.0 N AcOH was added, and the sample was cooled to 0° C. and centrifuged at 16,000×g for 10 min. The supernatant was removed, and the phage pellet resuspended in 600 μL PBS.

2. Attachment of Dansyl

The same procedure was used as in A above, except that phage clone ON5/6-#2 (titer=$2.2\times10^{12}$ TU/mL) was treated with Dansyl-X, succinimidyl ester (Dansyl-SE, available from Molecular Probes).

3. Attachment of Texas Red

The same procedure was used as in A above, except that phage clone ON5/6-#3 (titer=$1\times10^{12}$ TU/mL) was treated with Texas Red-X, succinimidyl ester (Texas Red-SE, available from Molecular Probes).

B. ELISA Detection

Figure 22:
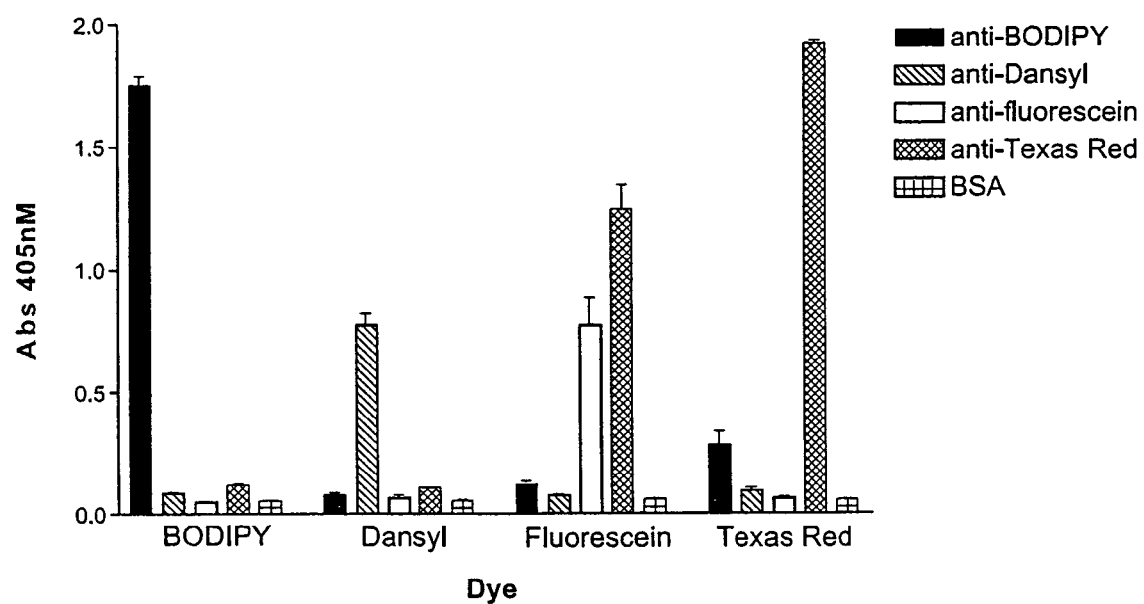
FIG. 22 shows ELISA detection of four fluor-conjugated phage captured with the indicated immobilized antibody. The fluors (BODIPY, Dansyl, Fluorescein or Texas Red) were conjugated to the phage using NHS ester conjugation chemistry.

50 μL of a 0.05 mg/mL solution of anti-fluor antibody were added to the indicated column of a microtiter plate according to the following scheme: Column 1: anti-BODIPY, Column 2: Anti-Dansyl, Column 3: anti-Fluorescein and Column 4: Anti-Texas Red (all done in duplicate). The plate was incubated at 37° C. for 1.5 h and washed. 300 μL of 1% BSA/PBS added to columns 1-5, incubated at 37° C. for 3 h and washed. 50 μL of 0.1% BSA/PBS was added across the plate, then 50 μL of the following phage samples were added to the indicated rows: Reaction #1 of BODIPY-conjugated clone to row 1, Reaction #2 of BODIPY-conjugated clone to row 2, Reaction #1 of Dansyl-conjugated clone to row 3, Reaction #2 of Dansyl-conjugated clone to row 4, Reaction #1 of Texas Red-conjugated clone to row 5, Reaction #2 of Texas Red-conjugated clone to row 6, Reaction #1 of Fluorescein-conjugated clone (from part VIII of Example X) to row 7 and Reaction #2 of Fluorescein-conjugated clone (from part VIII of Example X) to row 8. The plate was incubated overnight at 4° C. and washed. 100 μL of anti-phage/HRP conjugate (1:5000 dilution in 0.1% BSA/PBS) was added, incubated for 2 h at room temperature and washed. 100 μL substrate solution (18 μL 30% $H_2O_2$ added to 10 mL 1×ABTS) was added and the absorbance at 405 nm was measured in a microtiter plate reader (FIG. 22).

C. Screening Library of Four Fluors Attached to Phage Clones that Contain Unique Sequence Tags Two microtiter plates were prepared according to the following procedure: 50 μL of 0.05 mg/mL anti-fluor antibody were added according to the following scheme: Column 1: anti-BODIPY, Column 2: Anti-Dansyl, Column 3: anti-Fluorescein and Column 4: Anti-Texas Red (all done in duplicate). The plates were incubated at 37° C. and washed. 300 μL of 1% BSA/PBS was added to each well, incubated at 37° C. for 2 h and washed. To Plate #1 was added 50 μL of 0.1% BSA/PBS and 50 μL of p8 Xeno (titer=$10^{11}$ TU/mL). To Plate #2 was added 50 μL of 0.1% BSA/PBS, followed by 50 μL of a mixture of all four fluor-conjugated phage in a background of unmodified phage (this phage mixture contained p8 Xeno at $10^{11}$ TU/mL and each of the four fluor-conjugated phage at $10^7$ TU/mL).

The plates were incubated at 4° C. overnight and washed. The wells were filled with PBS and allowed to stand at room temperature for 3 h, then washed again. 100 μL of acidic elution buffer (0.1 N H Cl, pH 2.2 with glycine, 0.1% BSA) were added to each well and let stand at room temperature 10 min. The eluant from the two duplicate wells were combined and neutralized with 15.6 μL of 1.5 M Tris base. From Plate

2, four plates were generated from each eluant by adding 10 μL of the neutralized eluant to 100 μL of K91RecA cells at log phase, incubating at 37° C. for 20 min, plating onto LB plates containing ampicillin and incubating overnight at 37° C. In addition, control plates were generated from only p8 Xeno and each of the four clones conjugated to the four fluors.

The resultant colonies on these plates were lifted onto nitrocellulose filters, then washed in denaturation buffer (0.5 N NaOH, 1.5 M NaCl) for 5 min, followed by neutralization buffer (1.5 M NaCl, 0.5 M Tris, pH=7.5) for 5 min and 2×SSPE for 5 min. The filters were dried in a gel dryer at 80° C. for 2 h and washed in 2×SSPE with 0.1% SDS for 15 min. The filters were added to a hybridization bag such that each bag contained a p8 Xeno filter (negative control), a filter generated from one of the four clones (positive control) and a filter from each well of the capture plate. A total of four such bags were generated. The filters were first incubated in 19 mL complete hybridization solution for 30 min at 62° C. At this point, to each bag was added 200 μL of the radiolabeled probe specific for the clone included as the positive control (all probes contained between 20,000 and 30,000 cpm/μL).

The hybridization bags were incubated overnight at 62° C. The filters were washed in 2×SSPE with 0.1% SDS for 20 min, dried and exposed to a phosphor screen over 18 h. The screen was then imaged to reveal the colonies to which the probe had hybridized. Similarly, from Plate #1, one such filter lift was generated from each well and included in a hybridization bag with a p8 Xeno filter lift. To this bag was added a mixture of 200 μL of each radiolabeled probe, hybridized overnight and developed as above. The results from all these experiments are shown in Tables 2-5.

The examples and embodiments described are for illustrative purposes only and that various modifications or changes in light thereof will be suggested to persons skilled in the art and are to be included within the spirit and purview of this application and scope of the appended claims. All publications, patents, and patent applications cited herein are hereby expressly incorporated by reference in their entirety for all purposes to the same extent as if each individual publication, patent or patent application were specifically and individually indicated to be so incorporated by reference.

TABLE 1

| Phage Population[1] | Screen Target | Total Colonies | % Positive | Enrichment | % Recovery |
|---|---|---|---|---|---|
| Unlabeled background phage (p8Xeno) | Anti-Fluorescein | 32 | 0 | | |
| Unlabeled background phage (p8Xeno) | None | 60 | 0 | | |
| Unlabeled background phage (p8Xeno) | BSA | 100 | 0 | | |
| 1/10[4] | Anti-Fluorescein | 62 | 92 | $9 \times 10^3$ | 57 |
| 1/10[6] | Anti-Fluorescein | 83 | 72 | $7 \times 10^5$ | 60 |
| Fluorescein-labeled clone | None | 19 | 100 | | |
| 1/10[4] | BSA | 164 | 0 | | |
| 1/10[6] | BSA | 15 | 0 | | |

[1]A filamentous phage clone, identifiable by a unique DNA insert, was conjugated with fluorescein and diluted into a background of unlabeled phage (p8Xeno). Entries shown as 1/10[n] refer to the amount of fluorescein-conjugated clone diluted into a background of unconjugated phage (p8Xeno).

TABLE 2

Hybridization with Probe Specific for BODIPY-labeled Clone

| Phage Population[1] | Type of Antibody | Total Colonies | % Positive | Enrichment | % Recovery |
|---|---|---|---|---|---|
| BODIPY-labeled clone | Anti-BODIPY | 46 | 100 | | |
| Unlabeled background phage (p8Xeno) | Anti-BODIPY | 60 | 0 | | |
| 1/10[4] Dilution | Anti-BODIPY | 620 | 16 | 1600 | 0.2 |
| 1/10[4] Dilution | Anti-Fluorescein | 367 | 0 | | |
| 1/10[4] Dilution | Anti-Dansyl | 140 | 0 | | |
| 1/10[4] Dilution | Anti-Texas Red | 350 | 0 | | |

[1]Entries shown as 1/10[4] refer to the amount by which each of the four fluor-labeled clones was diluted into a background of unlabeled phage (p8Xeno).

TABLE 3

Hybridization with Probe Specific for Dansyl-labeled Clone

| Phage Population[1] | Type of Antibody | Total Colonies | % Positive | Enrichment | % Recovery |
|---|---|---|---|---|---|
| Dansyl-labeled Clone | Anti-Dansyl | 81 | 94 | | |
| Unlabeled background phage (p8Xeno) | Anti-Dansyl | 61 | 0 | | |
| 1/10[4] Dilution | Anti-BODIPY | 600 | 0 | | |
| 1/10[4] Dilution | Anti-Fluorescein | 331 | 3 | 300 | 0.02 |
| 1/10[4] Dilution | Anti-Dansyl | 131 | 12 | 1200 | 0.03 |
| 1/10[4] Dilution | Anti-Texas Red | 350 | 0 | | |

[1]Entries shown as 1/10[4] refer to the amount by which each of the four fluor-labeled clones was diluted into a background of unlabeled phage (p8Xeno).

TABLE 4

Hybridization with Probe Specific for Fluorescein-labeled Clone

| Phage Population[1] | Type of Antibody | Total Colonies | % Positive | Enrichment | % Recovery |
|---|---|---|---|---|---|
| Fluorescein-labeled Clone | Anti-Fluorescein | 19 | 84 | | |
| Unlabeled background phage (p8Xeno) | Anti-Fluorescein | 170 | 0 | | |
| 1/10[4] Dilution | Anti-BODIPY | 760 | 0 | | |
| 1/10[4] Dilution | Anti-Fluorescein | 191 | 42 | 4200 | 0.02 |
| 1/10[4] Dilution | Anti-Dansyl | 105 | 0 | | |
| 1/10[4] Dilution | Anti-Texas Red | 480 | <1 | | |

[1]Entries shown as 1/10[4] refer to the amount by which each of the four fluor-labeled clones was diluted into a background of unlabeled phage (p8Xeno).

TABLE 5

Hybridization with Probe Specific for Texas Red-labeled Clone

| Phage Population[1] | Type of Antibody | Total Colonies | % Positive | Enrichment | % Recovery |
|---|---|---|---|---|---|
| Texas Red-labeled Clone | Anti-Texas Red | 48 | 100 | | |
| Unlabeled background phage (p8Xeno) | Anti-Texas Red | 28 | 0 | | |
| 1/10⁴ Dilution | Anti-BODIPY | 560 | <1 | | |
| 1/10⁴ Dilution | Anti-Fluorescein | 275 | 0 | | |
| 1/10⁴ Dilution | Anti-Dansyl | 95 | 8 | 800 | 0.02 |
| 1/10⁴ Dilution | Anti-Texas Red | 470 | 17 | 1700 | 0.2 |

[1]Entries shown as 1/10⁴ refer to the amount by which each of the four fluor-labeled clones was diluted into a background of unlabeled phage (p8Xeno).

What is claimed is:

1. A method of screening a library of compounds, comprising:

(a) providing a plurality of bacteriophage, each of the bacteriophage displaying a compound other than a polypeptide expressed by the bacteriophage, different bacteriophage displaying different compounds and harboring different heterologous nucleic acid tags, wherein:

each of the heterologous nucleic acid tags is inserted into the genome of the bacteriophage;

each of the heterologous nucleic acid tags is a nucleic acid segment other than a segment that encodes for a polypeptide displayed on the bacteriophage; and each of the compounds is associated with a specific heterologous nucleic acid tag;

(b) assaying the plurality of bacteriophage to identify at least one bacteriophage displaying at least one compound with a desired property; and (c) decoding the heterologous nucleic acid tag of the at least one bacteriophage to identify a characteristic of the at least one compound with the desired property.

2. The method of claim 1, further comprising generating a correspondence regime indicating which compound is attached to which bacteriophage.

3. The method of claim 2, wherein the correspondence regime is a correspondence regime between the compounds and the heterologous nucleic acid tags harbored by the bacteriophage, and the characteristic of the at least one compound is determined by matching the sequence of the heterologous nucleic acid tag of the at least one bacteriophage and a sequence of the heterologous nucleic acid tag in the correspondence regime.

4. The method of claim 1, wherein each compound is contacted with one or more bacteriophage that each harbor the same heterologous nucleic acid tag, whereby each of the one or more bacteriophage contacted bears the same compound; wherein:
bacteriophage harboring the same heterologous nucleic acid tags display the same compound; and
bacteriophage harboring different heterologous nucleic acid tags display different compounds.

5. The method of claim 1, wherein
(a) the library of compounds to be screened are separated into a plurality of pools, each pool comprising a plurality of compounds from the library; contacting each pool of compounds with one or more bacteriophage that harbor the same heterologous nucleic acid tag, whereby each of the one or more bacteriophage that harbors the same heterologous nucleic acid tag displays a plurality of different compounds; and combining the one or more bacteriophage from the plurality of pools to provide the plurality of bacteriophage; and
(b) assaying comprises
(i) assaying the plurality of bacteriophage to identify an initial bacteriophage displaying a compound wherein at least one of the plurality of compounds has the desired property; and
(ii) repeating the assay with a set of bacteriophage, wherein each member of the set displays one of the compounds borne by the initial bacteriophage to identify the at least one bacteriophage.

6. The method of claim 1, wherein the decoding step is performed by sequencing the heterologous nucleic acid tag of the at least one bacteriophage.

7. The method of claim 1, wherein the decoding step comprises:
(a) generating a nucleic acid probe from the at least one bacteriophage, the nucleic acid probe comprising or being complementary to the heterologous nucleic acid tag of the at least one bacteriophage; and
(b) contacting the probe to the heterologous nucleic acid tag from the plurality of bacteriophage to identify the bacteriophage displaying the at least one compound.

8. The method of claim 7, further comprising determining the identity of the at least one compound from a correspondence regime between different bacteriophage and different compounds.

9. The method of claim 7, wherein the bacteriophage are arranged in an array for the contacting step.

10. The method of claim 1, wherein the desired property is selected from the group consisting of the capacity to bind to a receptor, the capacity to be transported into or through a cell, the capacity to be a substrate or inhibitor for an enzyme, the capacity to kill bacteria fungi or other microorganisms, and the capacity to agonize or antagonize a receptor.

11. The method of claim 10, wherein the desired property is the capacity to bind to a receptor and the assaying step comprises contacting the plurality of bacteriophage displaying different compounds with the receptor and identifying at least one bacteriophage displaying a compound that binds to the receptor.

12. The method of claim 10, wherein the desired property is the capacity to be transported into or through a cell and the assaying step comprises contacting the plurality of bacteriophage displaying different compounds with the cell and identifying at least one bacteriophage displaying a compound that is transported into or through the cell.

13. The method of claim 10, wherein the desired property is the capacity to be a substrate or inhibitor of an enzyme and the assaying step comprises contacting the plurality of bacteriophage with the enzyme and identifying at least one bacteriophage displaying a compound that is a substrate or an inhibitor of the enzyme.

14. A method of screening a library of compounds, comprising:
(a) providing a plurality of bacteriophage each of the bacteriophage displaying a compound other than a polypeptide expressed by the bacteriophage, and harboring a heterologous nucleic acid tag, wherein:
the heterologous nucleic acid tag is inserted into the genome of the bacteriophage;
the heterologous nucleic acid tag is a nucleic acid segment other than a segment that encodes for a polypeptide displayed on the bacteriophage; and
each compound is associated with a specific heterologous nucleic acid tag;
(b) assaying the plurality of bacteriophage to identify at least one bacteriophage displaying at least one compound with a desired property; and
(c) decoding the heterologous nucleic acid tag of the at least one bacteriophage to identify a characteristic of the at least one compound with the desired property.

15. The method of claim 14, wherein the plurality of bacteriophage are combined into a pool and the pool is contacted with a compound of the library, the harboring different heterologous nucleic acid tags, whereby bacteriophage harboring different heterologous nucleic acid tags bear the same compound.

16. The method of claim 14, wherein the library of compounds to be screened are combined into a pool and the plurality of bacteriophage harboring different heterologous nucleic acid tags are combined into a pool, and the pool of bacteriophage is contacted with the pool of compounds, whereby bacteriophage harboring different tags bear the same plurality of compounds.

17. A method of screening a library of compounds, comprising:
(a) for each compound to be screened, contacting each compound with a bacteriophage to form a plurality of bacteriophage displaying different compounds and harboring different heterologous nucleic acid tags; wherein:
each of the heterologous nucleic acid tags is inserted into the genome of the bacteriophage; and
each of the heterologous nucleic acid tags is a nucleic acid segment other than a segment that encodes for a polypeptide displayed on the bacteriophage; and
(b) assaying the bacteriophage displaying different compounds to identify at least one bacteriophage displaying at least one compound with a desired property.

18. The method of claim 17, wherein the method further comprises decoding the heterologous nucleic acid tag of the at least one bacteriophage to identify a characteristic of the at least one compound with the desired property.

* * * * *

SEQUENCE LISTING

<160> NUMBER OF SEQ ID NOS: 7

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:genetic
      element inserted into phagemid (gene VIII)

<400> SEQUENCE: 1
gcggccgcws sswwswwsws wwwswwsssg aattccctat agtgagtcgt attaaagctt        60

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence:BirA
      biotinylation substrate sequence
<220> FEATURE:
<221> NAME/KEY: MOD_RES
<222> LOCATION: (11)
<223> OTHER INFORMATION: Xaa = Lys modified by biotin

<400> SEQUENCE: 2

Gly Gly Leu Asn Asp Ile Phe Glu Ala Gln Xaa Ile Glu Trp His Glu
 1               5                  10                  15

Gly Gly Gly Gly Ser
            20

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence:5' end of
      gene for filamentous phage coat protein pVIII

<400> SEQUENCE: 3
ggcgggctta atgatatttt tgaggctcag aagattgagt ggcatgaggg aggcggggt         60 agc                                                                     63

<210> SEQ ID NO 4
<211> LENGTH: 20
<212> TYPE: PRT
<213> ORGANISM: Artificial Sequence
<220> FEATURE:

-continued

```
<223> OTHER INFORMATION: Description of Artificial Sequence:BirA
      biotinylation substrate sequence
<220> FEATURE:
<221> NAME/KEY: MOD_RES
<222> LOCATION: (15)
<223> OTHER INFORMATION: Xaa = Lys modified by biotin

<400> SEQUENCE: 4

Asn Ser Gly Gly Gly Gly Leu Asn Asp Ile Phe Glu Ala Gln Xaa Ile
  1               5                  10                  15

Glu Trp His Glu
            20

<210> SEQ ID NO 5
<211> LENGTH: 71
<212> TYPE: DNA
<213> ORGANISM: Artificial Sequence
<220> FEATURE:
<223> OTHER INFORMATION: Description of Artificial Sequence:3' end of
      gene 10B major coat protein of T7 phage

<400> SEQUENCE: 5
aattctggag gcgggggtct taatgatatt tttgaggctc agaagattga gtggcatgag      60
taagtaacta a                                                           71

<210> SEQ ID NO 6
<211> LENGTH: 58
<212> TYPE: DNA
<213> ORGANISM: Artificial Sequence
<220> FEATURE:
<223> OTHER INFORMATION: Description of Artificial Sequence:genetic
      element inserted into T7 phage vector

<400> SEQUENCE: 6
gcggccgcws sswwswwsws wwwswwsssg tattctatag tgtcacctaa atctcgag        58

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:mAb 3E7
      epitope peptide

<400> SEQUENCE: 7

Tyr Gly Gly Phe Leu
  1               5
```